United States Patent [19]

Kathawala

[11] Patent Number: 4,739,073

[45] Date of Patent: Apr. 19, 1988

[54] INTERMEDIATES IN THE SYNTHESIS OF INDOLE ANALOGS OF MEVALONOLACTONE AND DERIVATIVES THEREOF

[75] Inventor: Faizulla G. Kathawala, Mountain Lakes, N.J.

[73] Assignee: Sandoz Pharmaceuticals Corp., E. Hanover, N.J.

[21] Appl. No.: 707,854

[22] Filed: Mar. 4, 1985

Related U.S. Application Data

[63] Continuation of Ser. No. 548,850, Nov. 4, 1983, which is a continuation-in-part of Ser. No. 443,668, Nov. 22, 1982.

[51] Int. Cl.[4] .................. C07D 405/06; C07D 209/12
[52] U.S. Cl. .................................... 548/406; 548/414; 548/494
[58] Field of Search ............... 548/465, 467, 494, 468, 548/414, 406

[56] References Cited

U.S. PATENT DOCUMENTS

| | | | |
|---|---|---|---|
| 3,259,633 | 7/1966 | Metlesics et al. | 548/493 |
| 4,248,889 | 2/1981 | Oka et al. | 514/532 |
| 4,255,444 | 3/1981 | Oka et al. | 514/460 |
| 4,272,533 | 6/1981 | Gradient et al. | 514/212 |
| 4,375,475 | 3/1983 | Willard et al. | 514/460 |
| 4,474,971 | 10/1984 | Wareing | 549/214 |

Primary Examiner—Donald G. Daus
Assistant Examiner—William A. Teoli, Jr.
Attorney, Agent, or Firm—Gerald D. Sharkin; Richard E. Vila; Melvyn M. Kassenoff

[57] ABSTRACT

Compounds of the formula

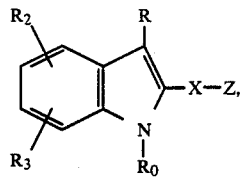

wherein one of R and $R_0$ is

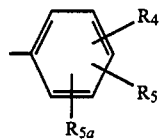

and the other is primary or secondary $C_{1-6}$alkyl not containing an asymmetric carbon atom, $C_{3-6}$cycloalkyl or phenyl$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, X is —$(CH_2)_n$— or —CH=CH—, wherein n is 0, 1, 2 or 3, and Z is

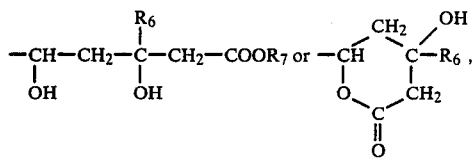

wherein $R_6$ is hydrogen or $C_{1-3}$alkyl, and $R_7$ is hydrogen, $C_{1-3}$alkyl, n-butyl, i-butyl, t-butyl, benzyl or M, wherein M is a pharmaceutically acceptable cation, the use thereof for inhibiting cholesterol biosynthesis and lowering the blood cholesterol level, and, therefore, in the treatment of hyperlipoproteinemia and atherosclerosis, pharmaceutical compositions comprising such compounds and processes for and intermediates in the synthesis of such compounds.

20 Claims, No Drawings

INTERMEDIATES IN THE SYNTHESIS OF INDOLE ANALOGS OF MEVALONOLACTONE AND DERIVATIVES THEREOF

This application is a division of application Ser. No. 06/548,850, filed Nov. 4, 1983 and now abandoned, which in turn is a continuation-in-part of application Ser. No. 06/443,668, filed Nov. 22, 1982 and now abandoned.

This invention relates to compounds of the formula

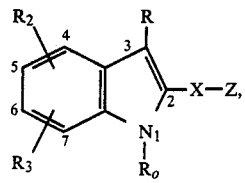

wherein one of
R and $R_o$ is

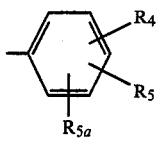

and the other is primary or secondary $C_{1-6}$alkyl not containing an asymmetric carbon atom, $C_{3-6}$cycloalkyl or phenyl-$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, X is —$(CH_2)_n$— or —CH=CH—, wherein n is 0, 1, 2 or 3, and Z is

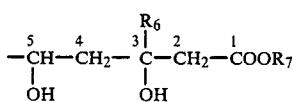

or

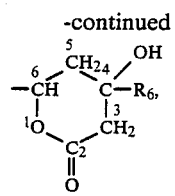

wherein
$R_6$ is hydrogen or $C_{1-3}$alkyl, and
$R_7$ is hydrogen, $C_{1-3}$alkyl, n-butyl, i-butyl, t-butyl, benzyl or M, wherein M is a pharmaceutically acceptable cation, processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

The compounds of Formula I may be divided into two groups, the compounds of Formula IA and those of Formula IB:

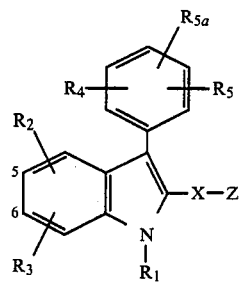

and

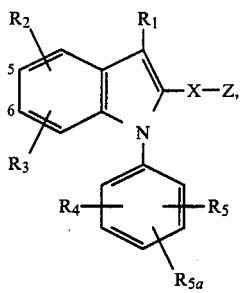

wherein
$R_1$ is primary or secondary $C_{1-6}$alkyl not containing an asymmetric carbon atom (e.g., methyl, ethyl, n-propyl, i-propyl, n-butyl, i-butyl, 1-ethylpropyl, neopentyl and n-hexyl), $C_{3-6}$cycloalkyl or phenyl-$(CH_2)_m$—, and
$R_2$-$R_{5a}$, X, Z and m are as defined above.

The compounds of Formula IA may be divided into two subgroups, the compounds wherein Z is a group of Formula II (Group IAa) and those wherein Z is a group of Formula III (Group IAb). Likewise, the compounds of Formula IB may be divided into two subgroups, the compounds wherein Z is a group of Formula II (Group IBa) and those wherein Z is a group of Formula III (Group IBb).

As is self-evident to those in the art, each compound of Formula I (and every subscope and species thereof) has two centers of asymmetry (the two carbon atoms bearing the hydroxy groups in the group of Formula II and the carbon atom bearing the hydroxy group and the carbon atom having the free valence in the group of Fromula III) and, therefore, there are four stereoisomeric forms (enantiomers) of each compound (two racemates or pairs of diastereoisomers), provided that M does not contain any center of asymmetry. The four stereoisomers may be designated as the R,R; R,S; S,R and S,S enantiomers, all four stereoisomers being within the scope of this invention.

$R_1$ is preferably $R_1'$, where $R_1'$ is primary or secondary $C_{1-6}$alkyl not containing an asymmetric carbon atom, more preferably $C_{1-3}$alkyl and most preferably methyl, ethyl or i-propyl, especially i-propyl.

$R_2$ is preferably $R_2'$, where $R_2'$ is hydrogen, $C_{1-3}$alkyl, $C_{1-3}$alkoxy, trifluoromethyl, fluoro, chloro, phenoxy or benzyloxy, more preferably $R_2''$, where $R_2''$ is hydrogen, $C_{1-3}$alkyl, methoxy, fluoro, chloro or 4-, 5- or 6-benzyloxy, and most preferably $R_2'''$, where $R_2'''$ is hydrogen, $C_{1-3}$alkyl or 4- or 6-benzyloxy, especially hydrogen or methyl and most especially hydrogen.

$R_3$ is preferably $R_3'$, where $R_3'$ is hydrogen, $C_{1-3}$alkyl, $C_{1-2}$alkoxy, fluoro or chloro, more preferably $R_3''$, where $R_3''$ is hydrogen or $C_{1-3}$alkyl, and most preferably $R_3'''$, where $R_3'''$ is hydrogen or methyl, especially hydrogen. $R_3$ ($R_3'$, etc.) must be hydrogen when $R_2$ ($R_2'$, etc.) is hydrogen.

Preferably, when $R_2$ ($R_2'$, $R_2''$, etc.) is other than hydrogen and $R_3$ ($R_3'$, $R_3''$, etc.) is hydrogen, $R_2$ ($R_2'$, etc.) is in the 4-, 5- or 6-position.

Preferably, when both $R_2$ ($R_2'$, $R_2''$, etc.) and $R_3$ ($R_3'$, $R_3''$, etc.) are other than hydrogen, at least one of them is in the 5- or 6-position, neither of them is in the 7-position, and not more than one of them is a member of the group consisting of t-butyl, $C_{3-6}$cycloalkyl, trifluoromethyl, phenoxy and benzyloxy; more preferably, they are not ortho to each other when neither of them is a member of the group consisting of methyl, methoxy, fluoro and chloro. Most preferably, one is in the 4-position and the other is in the 6-position.

Except where otherwise indicated: (a) Any $C_{1-3}$alkyl, n-butyl, i-butyl, t-butyl or $C_{3-6}$cycloalkyl group as $R_2$, $R_2'$, $R_3$, $R_3'$, etc. is more preferably in the 4- or 6-position. (b) Any $C_{1-3}$alkoxy, n-butoxy, i-butoxy, fluoro or chloro substituent as $R_2$, $R_2'$, $R_3$, $R_3'$, etc. is more preferably in the 5-position. (c) Any benzyloxy as $R_2$, $R_2'$, $R_3$, $R_3'$, etc. is more preferably in the 4-, 5- or 6-position and most preferably in the 4- or 6-position, especially the 6-position.

$R_4$ is preferably $R_4'$, where $R_4'$ is hydrogen, $C_{1-3}$alkyl, $C_{1-3}$alkoxy, trifluoromethyl, fluoro, chloro, phenoxy or benzyloxy, more preferably $R_4''$, where $R_4''$ is hydrogen, methyl, methoxy, fluoro or chloro, and most preferably $R_4'''$, where $R_4'''$ is hydrogen, methyl or fluoro, especially $R_4''''$, where $R_4''''$ is hydrogen, 3- or 4-methyl or 4-fluoro and most especially 4-fluoro.

$R_5$ is preferably $R_5'$, where $R_5'$ is hydrogen, $C_{1-2}$alkyl, $C_{1-2}$alkoxy, fluoro or chloro, more preferably $R_5''$, where $R_5''$ is hydrogen, methyl, methoxy, fluoro or chloro, and most preferably $R_5'''$, where $R_5'''$ is hydrogen or methyl, especially hydrogen. $R_5$ ($R_5'$, $R_5''$, etc.) must be hydrogen when $R_4$ ($R_4'$, $R_4''$, etc.) is hydrogen.

$R_{5a}$ is preferably $R_{5a}'$, where $R_{5a}'$ is hydrogen or methyl, and most preferably hydrogen. $R_{5a}$ ($R_{5a}'$, etc.) must be hydrogen when at least one of $R_4$ ($R_4'$, $R_4''$, etc.) and $R_5$ ($R_5'$, $R_5''$, etc.) is hydrogen.

Preferably, when $R_4$ ($R_4'$, $R_4''$, etc.) is other than hydrogen and $R_5$ ($R_5'$, $R_5''$, etc.) and $R_{5a}$ ($R_{5a}'$, etc.) are both hydrogen, $R_4$ ($R_4'$, etc.) is in a meta or para position, more preferably the para position. The most preferred monosubstituted phenyl group is 4-fluorophenyl.

Preferably, when both $R_4$ ($R_4'$, $R_4''$, etc.) and $R_5$ ($R_5'$, $R_5''$, etc.) are other than hydrogen and $R_{5a}$ ($R_{5a}'$, etc.) is hydrogen, at least one of $R_4$ ($R_4'$, etc.) and $R_5$ ($R_5'$, etc.) is in a meta or para position (more preferably both are), and not more than one of them is a member of the group consisting of t-butyl, trifluoromethyl, phenoxy and benzyloxy; more preferably, $R_4$ ($R_4'$, etc.) and $R_5$ ($R_5'$, etc.) are not ortho to each other when neither of them is a member of the group consisting of methyl, methoxy, fluoro and chloro. The most preferred disubstituted phenyl groups are 3,4- and 3,5-dimethylphenyl and 4-fluoro-3-methylphenyl, especially 3,5-dimethylphenyl and 4-fluoro-3-methylphenyl.

Preferably, when each of $R_4$ ($R_4'$, etc.), $R_5$ ($R_5'$, etc.) and $R_{5a}$ ($R_{5a}'$, etc.) is other than hydrogen, at least two of them (more preferably all three) are in meta or para positions, and not more than one of them is a member of the group consisting of t-butyl trifluoromethyl, phenoxy and benzyloxy; more preferably, no two of them are ortho to each other unless at least one member of the or each pair of substituents that are ortho to each other is a member of the group consisting of methyl, methoxy, fluoro and chloro. The most preferred trisubstituted phenyl group is 3,5-dimethyl-4-fluorophenyl.

$R_6$ is preferably $R_6'$, where $R_6'$ is hydrogen or $C_{1-2}$alkyl, more preferably $R_6''$, where $R_6''$ is hydrogen or methyl, and most preferably hydrogen.

$R_7$ is preferably $R_7'$, where $R_7'$ is hydrogen, $C_{1-3}$alkyl or M, more preferably $R_7''$, where $R_7''$ is hydrogen, $C_{1-2}$alkyl or M, and most preferably M, especially sodium. M is preferably M' and more preferably sodium.

X is preferably X', where X' is $-(CH_2)_m-$ or

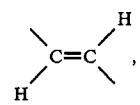

more preferably X", where X" is $-CH_2CH_2-$ or

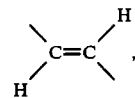

especially

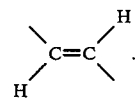

Z is preferably a group of Formula II wherein $R_6$ is $R_6'$ and $R_7$ is $R_7'$ or a group of Formula III wherein $R_6$ is $R_6'$; more preferably a group of Formula II wherein $R_6$ is $R_6''$ and $R_7$ is $R_7''$ or a group of Formula III wherein $R_6$ is $R_6''$ and most preferably a group of Formula II wherein $R_6$ is hydrogen and $R_7$ is $R_7''$ or a group of Formula III wherein $R_6$ is hydrogen, especially a group of Formula II wherein $R_6$ is hydrogen and $R_7$ is M, especially M' and most especially sodium, or a group of Formula III wherein $R_6$ is hydrogen.

n is preferably m, where m is 1, 2 or 3, preferably 2 or 3 and most preferably 2.

M is usually free from centers of asymmetry and is preferably M', i.e., sodium, potassium or ammonium, and most preferably sodium. For simplicity, all of the formulae in which M appears have been written as if M were monovalent and, preferably, it is. However, it may also be divalent or trivalent and, when it is, it balances the charge of two or three carboxy groups, respectively.

Insofar as the compounds of Groups IAa and IBa are concerned, the erythro isomers are generally preferred over the threo isomers, erythro and threo referring to the relative positions of the hydroxy groups in the 3- and 5-positions (of the group of Formula II).

As between compounds of Formula I having identical R, $R_o$, $R_2$, $R_3$, $R_6$ and X groups, those wherein Z is a group of Formula II are generally preferred over those wherein Z is a group of Formula III.

The preferred stereoisomers of the compounds of Formula I wherein X is a direct bond or —CH=CH—, and Z is a group of Formula II are the 3R,5S and 3R,5R isomers and the racemate of which each is a constituent, i.e., the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of Formula I wherein X is —$(CH_2)_m$—, and Z is a group of Formula II are the 3R,5R and 3R,5S isomers and the racemate of which each is a constituent, i.e., the 3R,5R-3S,5S (erythro) and 3R,5S-3S,5R (threo) racemates, with the 3R,5R isomer and the racemate of which it is a constituent being more preferred and the 3R,5R isomer being most preferred.

The preferred stereoisomers of the compounds of Formula I wherein X is a direct bond or —CH=CH—, and Z is a group of Formula III are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I wherein X is —$(CH_2)_m$—, and Z is a group of Formula III are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

Each of the preferences set forth above applies, not only to the compounds of Formula I, but also to the compounds of Formulae IA and IB and those of Groups IAa, IAb, IBa and IBb as well as to every other subgroup thereof set forth infra, e.g., Groups (i)-(cxiv), unless otherwise indicated. When any preference contains a variable, the preferred significances of that variable apply to the preference in question, unless otherwise indicated.

Representative groups of compounds of Formulae I, Ia and Ib and of Groups IAa, IAb, IBa and IBb include those of each of these seven groups wherein one of R and $R_o$ is

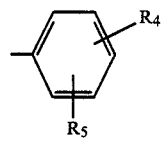

and the other is $C_{1-3}$alkyl, n-butyl or i-butyl,
$R_1$ is $C_{1-3}$alkyl, n-butyl or i-butyl, $R_2$ is hydrogen, $C_{1-3}$alkyl, n-butyl, i-butyl, $C_{1-3}$alkoxy, n-butoxy, i-butoxy, trifluoromethyl, fluoro, chloro, phenoxy or benzyloxy, $R_4$ is other than t-butyl, $R_{5a}$ is hydrogen, and X is —$(CH_2)_n$— or

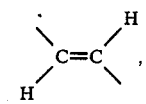

each of the other variables being as defined above.

Preferred groups of compounds of Formula I include the compounds (i) of Group IAa wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, $R_7$ is $R_7'$, and X is X', (ii) of (i) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (iii)-(iv) of (i) and (ii) wherein $R_6$ is $R_6''$, especially hydrogen, (v)-(vi) of (i) and (ii) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, $R_7$ is $R_7''$, and X is X'', (vii) of (i) wherein $R_1$ is $C_{1-3}$alkyl, $R_2$ is $R_2'''$, $R_3$ is $R_3'''$, $R_4$ is $R_4'''$, $R_5$ is $R_5'''$, $R_{5a}$ is hydrogen, $R_6$ is hydrogen, $R_7$ is $R_7''$, and X is $$\diagdown_H C=C \diagup^H_\diagdown ,$$

(viii)-(xiii) of (i)-(vi) wherein any M is M', (xiv) of Group IAb wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, and X is X', (xv) of (xiv) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (xvi)-(xvii) of (xiv) and (xv) wherein $R_6$ is $R_6''$, especially hydrogen, (xviii)-(xix) of (xiv) and (xv) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, and X is X'', (xx) of (xiv) wherein $R_1$ is $C_{1-3}$alkyl, $R_2$ is $R_2''$, '$R_3$ is $R_3'''$, $R_4$ is $R_4'''$, $R_5$ is $R_5'''$, $R_{5a}$ is hydrogen, $R_6$ is hydrogen, and X is

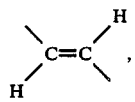

(xxi) of Group IBa wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, $R_7$ is $R_7'$, and X is X', (xxii) of (xxi) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (xxiii)-(xxiv) of (xxi) and (xxii) wherein $R_6$ is $R_6''$, especially hydrogen, (xxv)-(xxvi) of (xxi) and (xxii) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, $R_7$ is $R_7''$, and X is X'', (xxvii)-(xxxii) of (xxi)-(xxvi) wherein any M is M', (xxxiii) of Group IBb wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, and X is X', (xxxiv) of (xxxiii) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (xxxv)-(xxxxvi) of (xxxiii) and (xxxiv) wherein $R_6$ is $R_6'''$, especially hydrogen, (xxxvii)-(xxxviii) of (xxxiii) and (xxxiv) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, and X is X''', (xxxix)-(lxiii) of (i)-(xiii) and (xxi)-(xxxii) wherein the hydroxy groups in the 3- and 5-positions (of the group of Formula II) have the erythro configuration, (lxiv)-(lxxxviii) the 3R,5S enantiomers of the compounds of (xxxix)-(lxiii) wherein X is

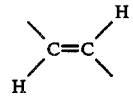

and the 3R,5R enantiomers of the compounds of these groups wherein X is —$(CH_2)_m$—, (lxxxix)-(ci) of (xiv)-(xx) and (xxxiii)-(xxxviii) wherein the hydroxy group on the lactone ring is trans to X (i.e., the trans lactones), and (cii)-(cxiv) the 4R,6S enantiomers of the compounds of (lxxxix)-(ci) wherein X is

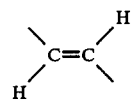

and the 4R,6R enantiomers of the compounds of these groups wherein X is —$(CH_2)_m$—.

Groups (xxxix)-(lxiii) embrace the 3R,5S-3S,5R racemate and the 3R,5S and 3S,5R enantiomers of the compounds wherein X is

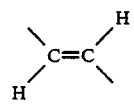

(the 3S,5R enantiomer being least preferred) and the 3R,5R-3S,5S racemate and the 3R,5R and 3S,5S enantiomers of the compounds wherein X is —$(CH_2)_m$— (the 3S,5S enantiomer being least preferred).

Groups (lxxxix)-(ci) embrace the 4R,6S-4S,6R racemate and the 4R,6S and 4S,6R enantiomers of the compounds wherein X is

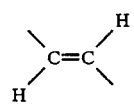

(the 4S,6R enantiomer being least preferred) and the 4R,6R-4S,6S racemate and the 4R,6R and 4S,6S enantiomers of the compounds wherein X is —$(CH_2)_m$— (the 4S,6S enantiomer being least preferred).

The compounds of Formula I may be synthesized as follows:

REACTION SCHEME I

The compounds of Formula I wherein $R_6$ is hydrogen may be synthesized by the following series of reactions:

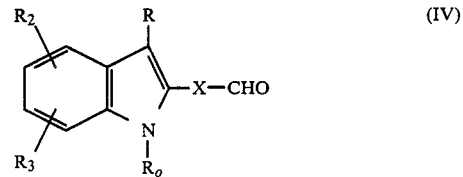

(IV)

A ↓ (1) Strong base +
  $CH_3$—CO—$CH_2$—COOR$_{7a}$ (IVA)
  (2) Aldehyde of Formula IV

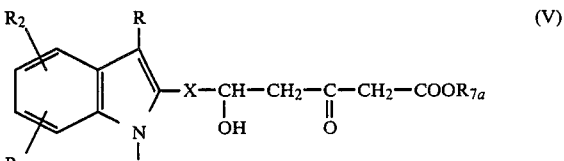

(V)

B ↓ Mild reducing agent

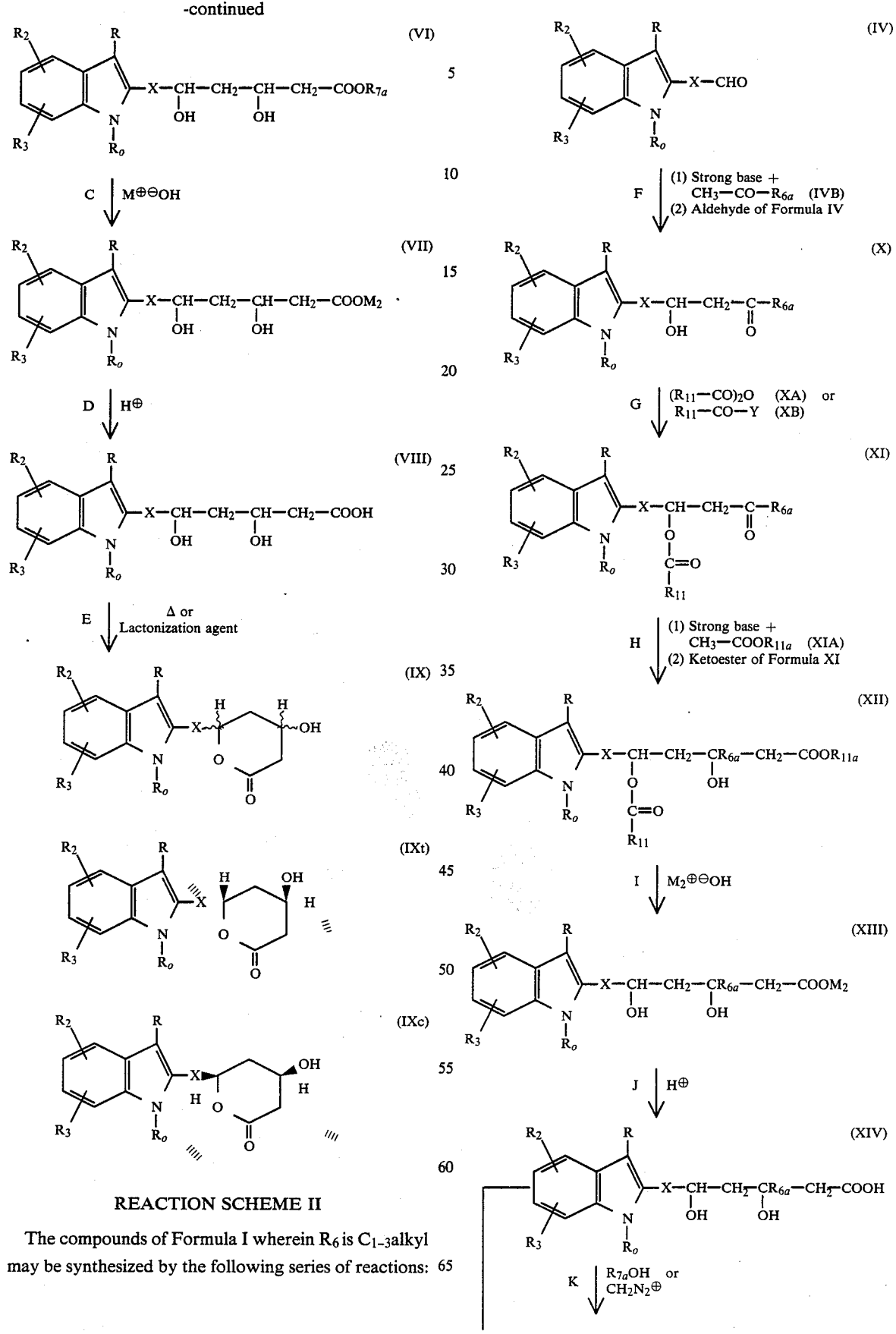
REACTION SCHEME II
The compounds of Formula I wherein $R_6$ is $C_{1-3}$alkyl may be synthesized by the following series of reactions:

-continued

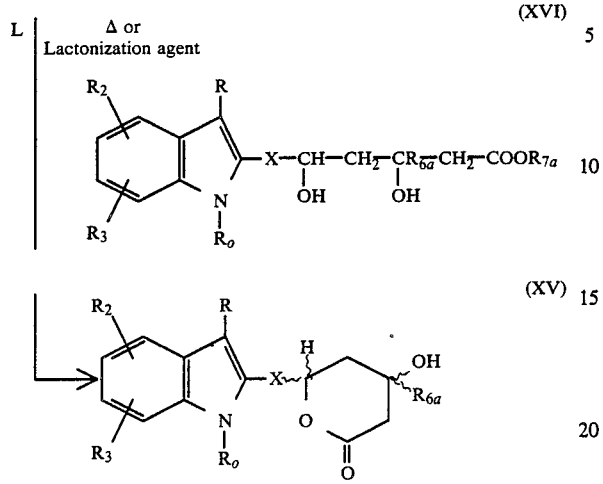

(XVI)

(XV)

REACTION SCHEME III

The compounds of Formula IV wherein X is a direct bond and those wherein X is

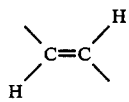

may be synthesized by the following series of reactions:

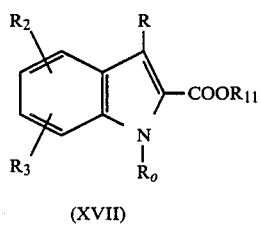

(XVII)

M ↓ Reducing agent

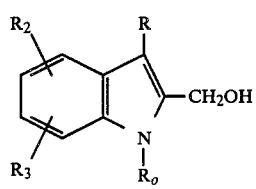

(XVIII)

N ↓ Mild oxidizing agent

-continued

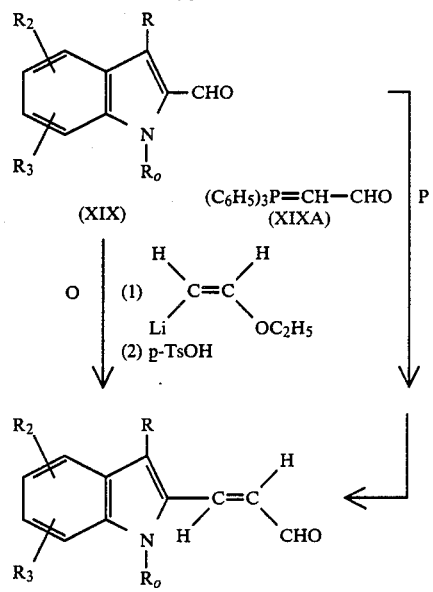

(XIX) → (XX)

REACTION SCHEME IV

The compounds of Formula XVII wherein $R_0$ is $R_1$ may be synthesized as follows:

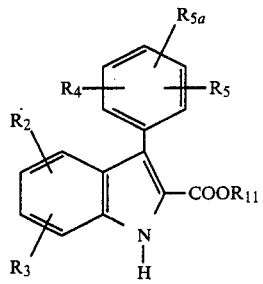

(XXI)

Q ↓ (1) Strong base
    (2) $R_1$—I

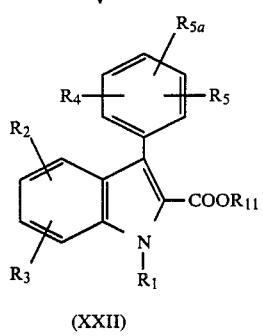

(XXII)

REACTION SCHEME V

The compounds of Formula IX wherein X is —CH═CH— may also be synthesized by the following series of reactions:

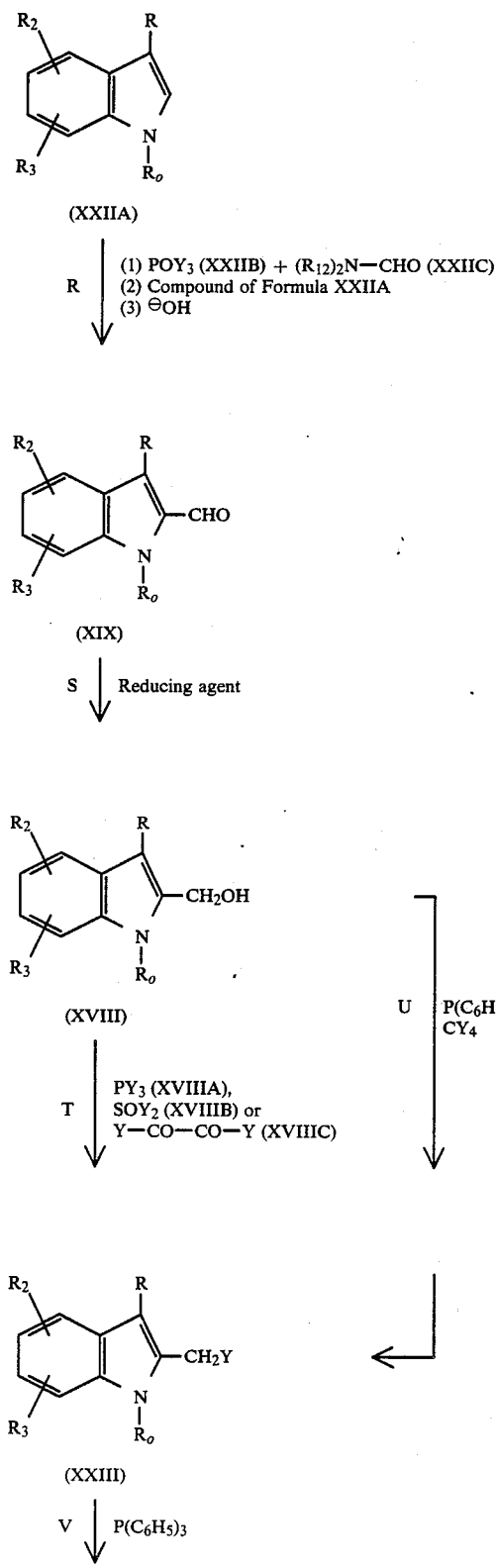
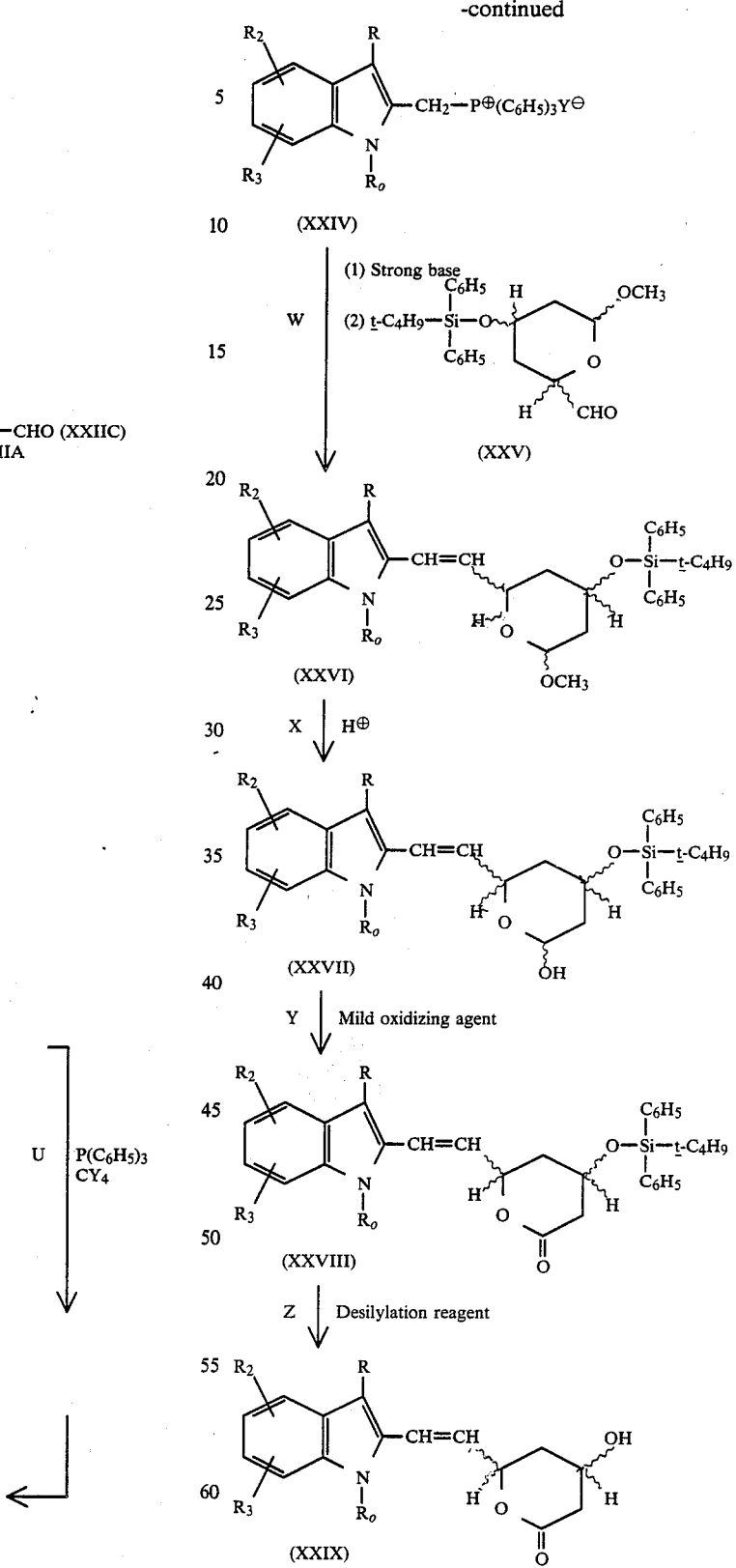
REACTION SCHEME VI
The compounds of Formula XX are preferably synthesized by the following reaction:

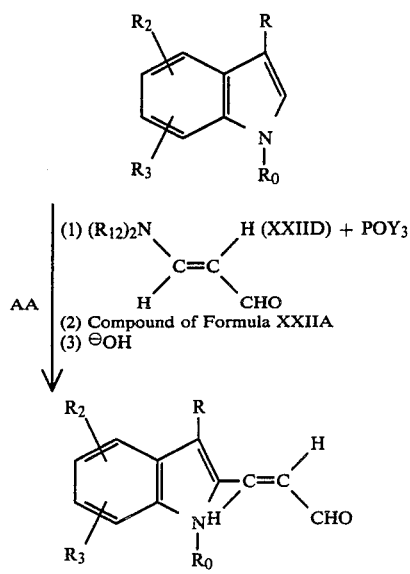

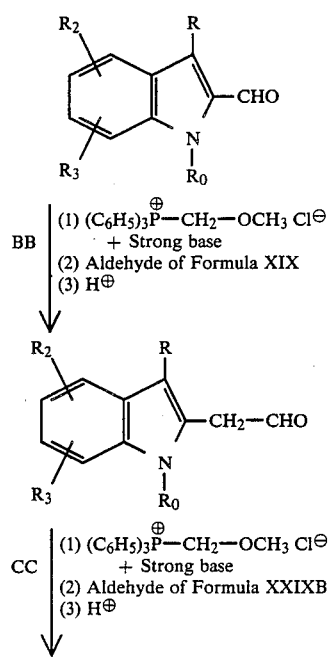

REACTION SCHEME VII

The compounds of Formula IV wherein X is —(CH$_2$)$_m$— may be synthesized by the following series of reactions:

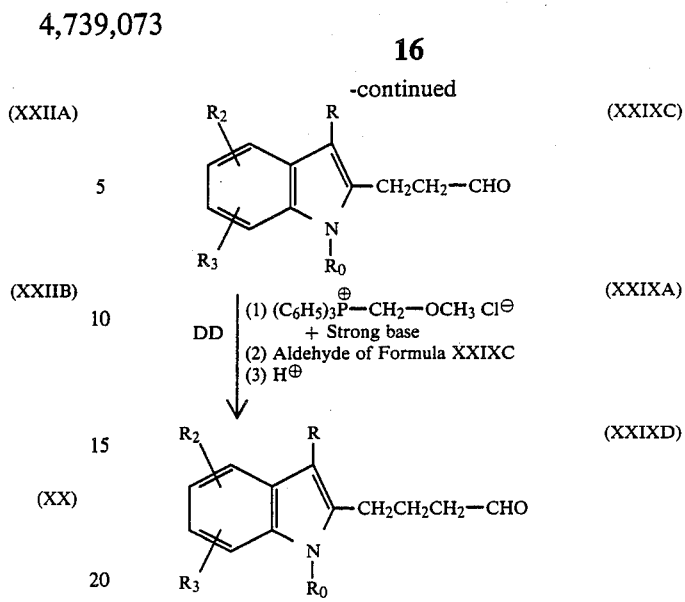

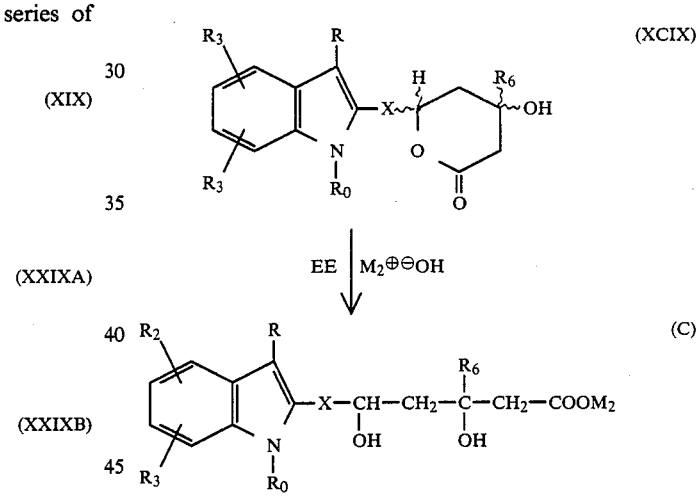

REACTION SCHEME VIII

The compounds of Formula I wherein Z is a group of Formula II wherein R$_7$ is M$_2$ may also be synthesized as follows:

REACTION SCHEME IX

Two isomers of the compound of Formula XXV may be synthesized by the following series of reactions:

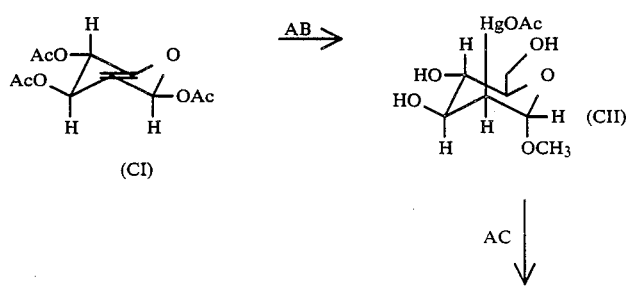

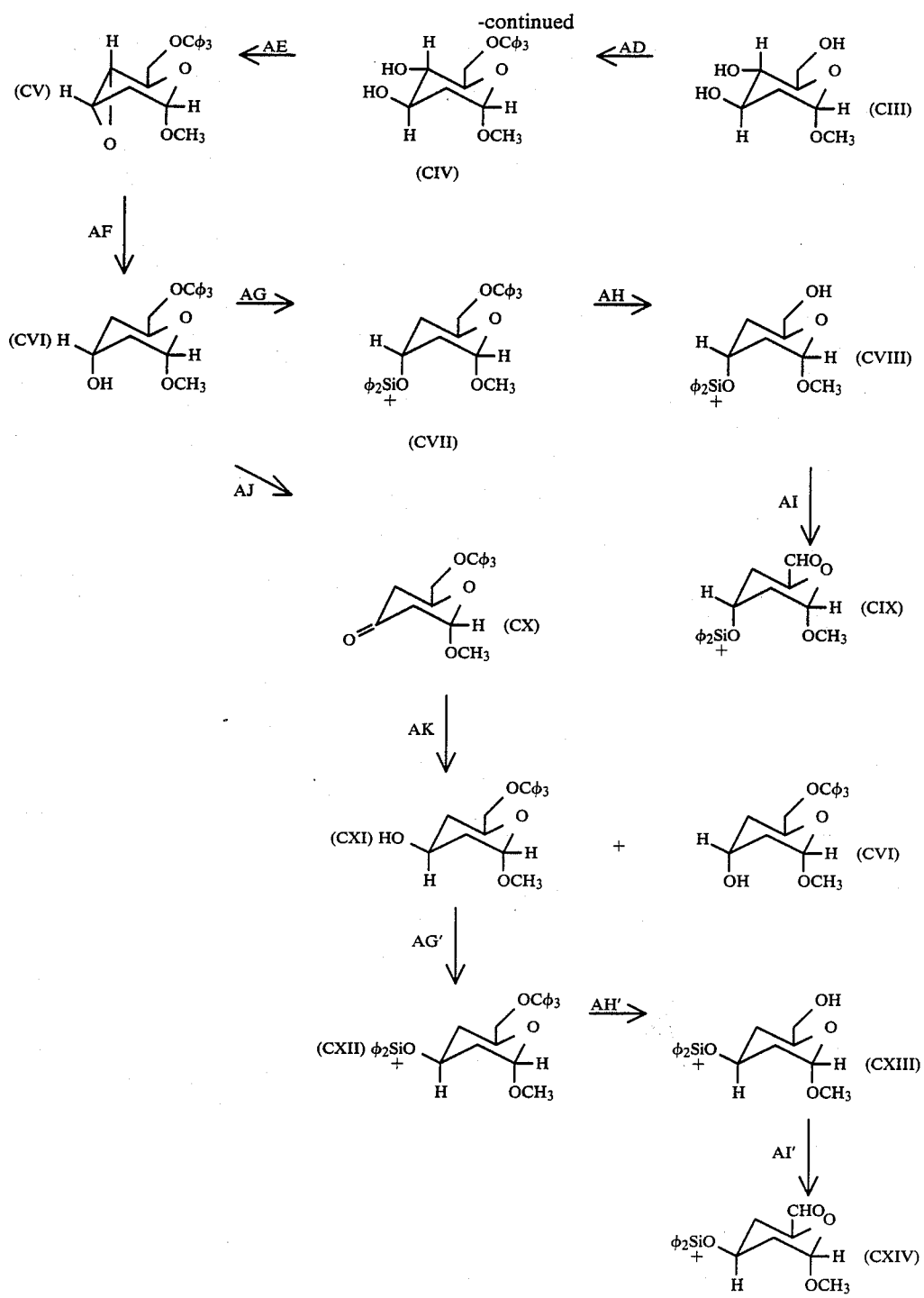

In the above formulae, $R_{6a}$ is $C_{1-3}$alkyl, preferably $C_{1-2}$alkyl and most preferably methyl, $R_{7a}$ is $C_{1-3}$alkyl, n-butyl, i-butyl, t-butyl or benzyl, preferably $C_{1-3}$alkyl and most preferably $C_{1-2}$alkyl, $R_{11}$ is $C_{1-2}$alkyl, preferably methyl, $R_{11a}$ is $C_{1-3}$alkyl, n-butyl or t-butyl, preferably ethyl or t-butyl, each $R_{12}$ is independently $C_{1-3}$alkyl, preferably $C_{1-2}$alkyl and more preferably methyl, each Y is chloro or bromo, preferably chloro, $M_2$ is M, preferably sodium or potassium, and each of the other variables is as set forth above.

In Reaction Scheme IX,

Ac is acetyl, $\phi$ is phenyl, and

+ is t-butyl.

As utilized herein, terms such as "solvent" and "solvent system" embrace mixtures of solvents and imply that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "an inert atmosphere", as utilized herein, means an atmosphere that does not react with any of the reactants, intermediates or end products or otherwise interfere with the reaction. While a carbon dioxide atmosphere is suitable for some reactions, the inert atmosphere is usually nitrogen, helium, neon, argon or krypton, or a mixture thereof, and preferably is nitrogen. Most reactions, including those where the use of an inert atmosphere is not specified, are carried out under such an atmosphere for convenience.

In reaction A, the dianion of the acetoacetic acid ester of Formula IVA is generated with 2–2.2 equivalents of a strong base per mole of said ester, and the resulting dianion is reacted with the compound of Formula IV. Among the strong bases that may be employed are n-butyllithium, lithium diisopropylamide and sodium hydride. However, sodium hydride can be used only to generate a monoanion; it cannot be used to generate a dianion. Consequently, when sodium hydride is used to generate the monoanion, 1–1.1 equivalents thereof are utilized and then 1–1.1 equivalents of n-butyllithium or lithium diisopropylamide are utilized to generate the dianion from the monoanion. The molar ratio of the acetoacetic acid ester of Formula IVA to the compound of Formula IV is preferably 1–2.1, more preferably 1.4–1.8:1. The temperature for both steps is conveniently $-80°-10°$ C., preferably $-20°-5°$ C. Both steps of the reaction are relatively rapid; the dianion is typically generated over the course of 20–90 minutes while the reaction of the dianion with the compound of Formula IV is generally run for 20–120 minutes. The reaction is carried out under an inert atmosphere in an anhydrous inert organic solvent, for example an ether solvent such as tetrahydrofuran, diethyl ether, 1,2-dimethoxyethane or 1,2-diethoxyethane, or a mixture thereof. The resulting compound of Formula V is a racemate.

The initial step of Reaction A is preferably carried out by generating the monoanion of the acetoacetic acid ester of Formula IVA with 1–1.05 equivalents of sodium hydride which is then treated with 1–1.05 equivalents of n-butyllithium, per mole of said acetoacetic acid ester in each case, at a temperature of about $-15°$ C.–$10°$ C.

In Reaction B, the keto group of the compound of Formula V is reduced to a hydroxy group with a mild reducing agent such as sodium borohydride or, preferably, a complex of t-butylamine and borane in an inert organic solvent such as a lower alkanol, preferably ethanol, conveniently at a temperature of $-10°-30°$ C., utilizing at least 1, for example 2–4, equivalents of transferable hydride per mole of compound of Formula V, under an inert atmosphere. The reaction time is suitably 1–8 hours. The compounds of Formula VI exist in four stereoisomeric forms; however, if an optically pure starting material of Formula V is utilized, only two optical isomers (diastereoisomers) of the resulting compound of Formula VI are obtained.

However, it is preferred to utilize a stereoselective reduction in order to maximize production of a mixture of the erythro stereoisomers (racemate) of which the preferred stereoisomer (as set forth above) is a constituent. Stereoselective Reaction B is preferably carried out in three steps. In the first step, the ketoester of Formula V is treated with a tri(primary or secondary $C_{2-4}$alkyl)borane, preferably triethylborane or tri-n-butylborane, and air to form a complex. The molar ratio of the trialkylborane to the ketoester of Formula V is preferably 1–1.25:1, more preferably 1.02–1.2:1, and 0.5–8 liters, preferably 0.75–6.5 liters, of air (at 25° C. and 760 mm. Hg) per mole of the ketoester of Formula V are typically used. The reaction temperature is suitably 0°–50° C., preferably 20°–30° C., and the reaction time is suitably 0.5–6 hours, preferably 0.5–3.5 hours. The first step is carried out in an anhydrous inert organic solvent, preferably an ether solvent such as tetrahydrofuran, diethyl ether, 1,2-dimethoxyethane or 1,2-diethoxyethane, with tetrahydrofuran being the most preferred solvent. In the second step, the complex is reduced with sodium borohydride, preferably in the same solvent as utilized for the first step, at $-100°--40°$ C., preferably $-90°--70°$ C., for 1–24 hours, preferably 2.5–18 hours. Preferably, 0.4–1.5, more preferably 1.0–1.5, moles of sodium borohydride per mole of the ketoester of Formula V are utilized. In the third step, the product of the second step is treated with, preferably, anhydrous methanol at 20°–40° C., preferably 20°–30° C., preferably for 0.7–5, more preferably 2–4, hours, to obtain the compound of Formula VI. The amount of methanol is not critical. However, a large excess, e.g., 50–500 moles per mole of ketoester of Formula V, is typically utilized.

Reactions C and I are conventional basic hydrolyses of esters. The ester of Formula VI or diester of Formula XII is treated with at least one equivalent of an inorganic hydroxide per mole of ester group to by hydrolyzed. Preferably, each mole of ester of Formula VI is treated with 1–1.2, preferably 1–1.1, and each mole of diester of Formula XII is treated with 2–2.3, preferably 2–2.2, equivalents of sodium hydroxide or potassium hydroxide in a mixture of water and a water-miscible organic solvent such as a lower alkanol, preferably a $C_{1-2}$alkanol, at a temperature of 20° C. to reflux, more preferably not in excess of 80° C. As is well-known, the reaction time is inversely related to the reaction temperature; however, a reaction time of 1–4 hours is generally acceptable. For example, a reaction time of 2–4 hours is particularly useful when the reaction is run at 20°–30° C. When it is desired to isolate the salt of Formula VII or XIII, it is preferable to utilize slightly less than one equivalent of the inorganic hydroxide, e.g., 0.95–0.98 equivalents per mole of ester group to be hydrolyzed.

Reactions D and J are conventional acidifications of a carboxylate salt to the corresponding carboxylic acid. The reactions are effected by treating the salt of Formula VII or XIII with a molar excess (e.g., 10–20%) of a dilute aqueous acid, e.g., 2N. hydrochloric acid, the pH of the reaction medium typically being 2–6.

In Reactions E and L the 3,5-dihydroxycarboxylic acid of Formula VIII or XIV is cyclized to form a lactone of Formula IX or XV, respectively. The reaction may be carried out by heating the 3,5-dihydroxycarboxylic acid in an anhydrous inert organic solvent, for example a hydrocarbon such as benzene, toluene or a xylene, or a mixture thereof, preferably at 75° C.-reflux, more preferably not in excess of 150° C., for 3–18 hours, optionally using a Dean-Stark apparatus if the solvent forms an azeotrope with water. The reaction is conveniently run by refluxing the 3,5-dihydroxycarboxylic acid of Formula VIII or XIV in benzene for 8 hours. Preferably, however, the dihydroxycarboxylic acid of Formula VIII or XIV is treated with a lactonization agent, e.g., a carbodiimide, preferably a water-soluble carbodiimide such as N-cyclohexyl-N'-[2-[N''-methylmorpholinium)ethyl]carbodiimide p-toluenesulfonate, in an anhydrous inert organic solvent, e.g., a halogenated lower alkane, preferably methylene chloride. When a carbodiimide, such as the aforementioned carbodiimide, is utilized, 1-1.2, preferably 1-1.1, moles thereof per mole of the dihydroxycarboxylic acid are conventionally utilized, the reaction temperature is typically 10°-35° C., preferably 20°-30° C., and the reaction time is conveniently 2-8 hours, preferably 3-4 hours, especially when the reaction temperature is 20°-30° C. The latter procedure often results in higher yields than the former. As is evident to those in the art, a racemic threo 3,5-dihydroxycarboxylic acid yields a racemic cis lactone and a racemic erythro 3,5-dihydroxycarboxylic acid yields a racemic trans lactone. Use of a mixture of threo and erythro 3,5-dihydroxycarboxylic acids yields a mixture of cis and trans lactones (all four possible diastereoisomers). Likewise if a single enantiomer of the 3,5-dihydroxycarboxylic acid is utilized, a single enantiomer of the lactone is obtained. For example, lactonization of a 3R,5S erythro dihydroxycarboxylic acid of Formula VIII yields a 4R,6S lactone of Formula IXt.

In Reaction F, a monoanion of the ketone of Formula IVB is generated by treating a solution of the ketone in an anhydrous inert organic solvent, such as those utilized for Reaction A, with 1-1.1 equivalents of a strong base such as lithium diisopropylamide per mole of said ketone followed by reaction of the monoanion with the aldehyde of Formula IV in the same solvent. The molar ratio of the ketone of Formula IVB to the aldehyde of Formula IV is preferably 3:1. The reaction is carried out under an inert atmosphere. The reaction temperature is suitably −80°−−40° C., preferably −80°−−75° C., and each of the two steps is generally carried out over a 15-90 minute period. If the product contains, in addition to the compound of Formula X, a compound not of said formula, the compound of Formula X is separated therefrom by conventional techniques, e.g., column chromatography or high pressure liquid chromatography.

In Reaction G the compound of Formula X is acylated with, for example, an acid anhydride of Formula XA or an acyl halide of Formula XB in the presence of a base such as pyridine or triethylamine. Conveniently, the compound of Formula X is treated with 1-3, preferably 2, moles of said acid anhydride or acyl halide per mole of the compound of Formula X in an excess of pyridine or preferably in an ether solvent such as tetrahydrofuran containing 1-4, preferably 2.5-3, moles of a tertiary amine base such as pyridine or, preferably, 4-dimethylaminopyridine per mole of the compound of Formula X at 10°-50° C., preferably 20°-30° C., for 2-18, preferably 4-12, hours.

Reaction H is also a two-step reaction. First, the ester of Formula XIA is treated with a strong base such as lithium diisopropylamide to form a monoanion, the molar ratio of the latter to the former being 1-1.1:1. The reaction is carried out in an anhydrous inert organic solvent, for example an ether such as diethyl ether, 1,2-dimethoxyethane, 1,2-diethoxyethane or, preferably, tetrahydrofuran, under an inert atmosphere. The reaction temperature is conveniently −80°-0° C., and the reaction time is usually 15-60 minutes. In the second step, said monoanion is reacted with the ester of Formula XI under an inert atmosphere in the same solvent system as utilized. for the first step, the molar ratio of the compound of Formula XIA to the compound of Formula XI preferably being 3:1. The reaction temperature is conveniently −80°−−40° C., preferably −80°−−70° C., and the reaction time is typically 15-90 minutes.

Reaction K is a conventional acid catalyzed esterification Conveniently, the compound of Formula XIV is treated with a large excess of an alcohol of the formula $R_{7a}$—OH at 20°-40° C. for 2-12 hours in the presence of a catalytic amount of an acid such as p-toluenesulfonic acid. The excess alcohol serves as the solvent. However, it is preferred to synthesize the compounds of Formula XVI wherein $R_{7a}$ is methyl by reacting the compound of Formula XIV with diazomethane in, preferably, an anhydrous inert ether solvent such as diethyl ether, tetrahydrofuran, 1,2-dimethoxyethane or 1,2-diethoxyethane, more preferably diethyl ether, at, for example, 0°-30° C., preferably 20°-25° C., for, typically, 10-30 minutes, preferably under an inert atomsphere. Generally, 1-4 moles, preferably 2-3 moles, of diazomethane per mole of the compound of Formula XIV are utilized.

Reaction M is a conventional reduction of a lower alkyl ester to the corresponding primary alcohol utilizing a metal hydride reducing agent such as lithium aluminum hydride or, preferably, diisobutylaluminum hydride in an anhydrous inert organic solvent, for example, an ether such as tetrahydrofuran, diethyl ether, 1,2-dimethoxyethane or 1,2-diethoxyethane, preferably tetrahydrofuran. The reaction is preferably carried out under an inert atmosphere. The reaction temperature is suitably −80° C.-reflux, preferably not in excess of 70° C., more preferably −80°-25° C., and the reaction time is suitably 3-12 hours. At least two equivalents of transferable hydride, preferably 4-4.4 equivalents, per mole of the compound of Formula XVII are used.

In Reaction N the alcohol of Formula XVIII is oxidized under mild conditions to the aldehyde of Formula XIX. Preferably, the alcohol of Formula XVIII is treated with a large molar excess, e.g., 10-30 moles, of manganese dioxide per mole of said alcohol in an inert anhydrous organic solvent, for example, an ether such as diethyl ether, tetrahydrofuran, 1,2-dimethoxyethane or 1,2-diethoxyethane, at a temperature of 20° C.-reflux (but not in excess of 80° C.). While the reaction time is inversely related to the reaction temperature, a reaction time of 4-24 hours, preferably 10-18 hours, when the reaction temperature is 20°-30° C., is generally suitable.

Reaction O is a three-step reaction. In the first step, cis-1-ethoxy-2-tri-n-butylstannylethylene (prepared by adding 1 equivalent of ethoxyacetylene to tri-n-butyltin hydride at 50° C. over a period of 1 hour and heating under an inert atmosphere at 50°-55° C. for 3 hours and at 60°-70° C. for 1 hour) is reacted for 1-3, preferably 2, hours with 1-1.05 equivalents of n-butyllithium per mole of the tin compound at −78° C. in anhydrous tetrahydrofuran under an inert atmosphere, the n-butyllithium/n-hexane solution being added dropwise, to form cis-1-lithium-2-ethoxyethylene. In the second step, said lithium compound is reacted with the compound of Formula XIX in the same solvent at −80°−−40° C., preferably at −80°−−70° C., under an inert atmosphere for 2-8, preferably 3-5, hours to form an intermediate compound. The molar ratio of the starting ethoxyethenyltin compound to the compound of Formula XIX is 1-1.15:1. In the third step, said intermediate compound is treated with a catalytic amount of p-toluenesulfonic acid (e.g., 0.5-2 g. of said acid per mole of the compound of Formula XIX) in an inert aqueous organic solvent, e.g., a mixture of water and tetrahydrofuran, for 1-5, preferably 1.5-2.5 hours at for example, room temperature.

Reaction P is a Wittig reaction and is carried out under conventional Wittig reaction conditions. The compound of Formula XIX is treated with 1-1.2 moles of the compound of Formula XIXA (per mole of the former) in an inert organic solvent, for example an anhydrous ether or hydrocarbon such as diethyl ether, 1,2-dimethoxyethane, 1,2-diethoxyethane, benzene or toluene, at 20° C.-reflux, preferably not in excess of 140° C., for 2-18 hours. It is preferable to carry out the reaction under an inert atmosphere.

In Reaction Q, the indole of Formula XXI is N-alkylated with an alkyl iodide of the formula $R_1$-I in a two-step reaction. In the first step, the indole of Formula XXI is treated with a strong base such as n-butyllithium or, preferably, sodium hydride, to generate an anion which, in the second step, is reacted with the alkyl iodide. Both steps are carried out in an anhydrous inert organic solvent such as tetrahydrofuran, diethyl ether, 1,2-dimethoxyethane, 1,2-diethoxyethane, diethylacetamide or, preferably, dimethylacetamide, the first step at $-20°-$ $-30°$ C. and the second step at $-15°$ C.-reflux, preferably not in excess of 80° C., most preferably 20°-30° C. The first step generally takes 15-60 minutes while the second step generally takes 1-5, usually 2-4, hours, 1-1.2 moles of the strong base per mole of the indole of Formula XXI are utilized in the first step, and 1-1.2 moles of the alkyl iodide per mole of said indole are utilized in the second step. An inert atmosphere is used for each step.

Reaction R is a three-step Vilsmeir-Haack reaction. In the exothermic initial step, the phosphorus oxyhalide of Formula XXIIB, preferably phosphorus oxychloride, and the N,N-dialkylformamide of Formula XXIIC, preferably dimethylformamide, are reacted to form an iminium salt. The reaction temperature is suitably 0°-35° C., preferably 0°-15° C., and the reaction time is suitably 5-30 minutes, preferably 10-20 minutes. Typically, 1-5 moles of the phosphorus oxyhalide and at least 1 mole of the N,N-dialkylformamide of Formula XXIIC, per mole of the indole of Formula XXIIA to be utilized in the second step, are used; preferably, however, 1.2-5 moles of the phosphorus oxyhalide and at least 1.5 moles of the N,N-dialkylformamide per mole of the indole of Formula XXIIA are used. If the N,N-dialkylformamide is a liquid, a large molar excess of it is utilized, the excess serving as the solvent. Alternatively, the reaction may be run in a liquid lower alkyl nitrile, such as acetonitrile, or a mixture thereof with the excess N,N-dialkylformamide. In the second step, the minimum salt is reacted with the indole of Formula XXIIA. The reaction temperature is suitably 60°-120° C., preferably 80°-105° C. (not in excess of reflux in each case) and while the reaction time is inversely related to the reaction temperature, it is suitably 3-18 hours, preferably 4-6 hours. The second step is carried out in the same solvent as the first step, both steps being carried out under anhydrous conditions and an inert atmosphere. In the third step, the adduct produced in the second step is decomposed with, for example, at least 4, preferably 4-6, more preferably 4, equivalents of an aqueous base, preferably aqueous sodium or potassium hydroxide, per mole of the phosphorus oxyhalide to liberate the aldehyde of Formula XIX. Preferably the exothermic third step is carried out at 10°-45° C. The third step is conveniently carried out by slowly adding 4-6 equivalents (per mole of the phosphorus oxyhalide) of, for example, 15% sodium hydroxide solution to the adduct of the second step stirred at 10°-25° C., the rate of the addition being such that the temperature of the reaction mixture does not exceed 45° C.

The aldehyde of Formula XIX is reduced to the alcohol of Formula XVIII in Reaction S with, preferably, a metal hydride reducing agent such as lithium aluminum hydride, diisobutylaluminum hydride or, preferably, sodium borohydride in an anhydrous inert organic solvent, e.g., an ether such as tetrahydrofuran, diethyl ether, 1,2-dimethoxyethane or 1,2-diethoxyethane or, when sodium borohydride is utilized, a mixture of such an ether and a lower alkanol, preferably a 9-15:1 mixture of tetrahydrofuran and methanol (by volume). The reaction temperature is suitably $-5°-35°$ C., preferably 0°-25° C. At least one equivalent of transferable hydride per mole of the aldehyde of Formula XIX is utilized. When sodium borohydride is the reducing agent, preferably 0.25-1, more preferably 0.35-0.5, moles thereof per mole of the aldehyde of Formula XIX is utilized. The reaction is preferably carried out under an inert atmosphere.

Reaction T is a conventional phosphorus trihalide, thionyl halide or oxalyl halide halogenation reaction. It is conveniently carried out by reacting the alcohol of Formula XVIII with an excess of a phosphorus trihalide of Formula XVIIIA (e.g., one mole of phosphorus trihalide), 1-2, preferably 1.2-2, more preferably 1.5-1.8, moles of a thionyl halide of Formula XVIIIB or 1-1.2, preferably 1.05-1.1, moles of an oxalyl halide of Formula XVIIIC (per mole of the alcohol of Formula XVIII in each case) in an anhydrous inert organic solvent, preferably an ether such as diethyl ether or tetrahydrofuran, optionally containing a trace of dimethylformamide, at a temperature of 20°-35° C. for 4-25 hours when a phosphorus trihalide is utilized or a temperature of $-10°-20°$ C., preferably $-10°-10°$ C., more preferably $-10°-5°$ C., for 2-4 hours when a thionyl halide or oxalyl halide is utilized.

In Reaction U the alcohol of Formula XVIII is reacted with 1-2, preferably 1-1.2, moles of triphenylphosphine and at least one mole of carbon tetrachloride or carbon tetrabromide (per mole of said alcohol in each case) at a temperature of $-10°$ C.-reflux, preferably no higher than 120° C., for 4-18 hours. The reaction may be run neat (i.e., using an excess of carbon tetrachloride or carbon tetrabromide as the solvent) or in an ether or hydrocarbon solvent, for example, diethyl ether, tetrahydrofuran, benzene or toluene. When the reaction is run neat, the preferred temperature range is 25° C.-reflux, more preferably no higher than 100° C.

In Reaction V, the halomethylindole of Formula XXIII is reacted in an anhydrous inert organic solvent, for example a hydrocarbon such as benzene, toluene or xylene, or a mixture thereof, with 1-1.25 moles of triphenylphosphine per mole of the halomethylindole. The reaction temperature is conveniently 60° C.-reflux, preferably not in excess of 150° C., more preferably 100°-110° C., and, while the reaction time is inversely related to the reaction temperature, it is conveniently 1-8 hours, preferably 3-6 hours. The reaction is run under an inert atmosphere.

Reaction W is a two-step reaction. First, the phosphonium compound of Formula XXIV is treated with 1-1.1 moles of a strong base such as sodium hydride or n-butyllithium per mole of phosphonium compound in an anhydrous inert organic solvent, for example an ether or hydrocarbon such as tetrahydrofuran, benzene or toluene, under an inert atmosphere at a temperature of 0°–25° C. for 5–60 minutes. The resulting intermediate is, in the second step, reacted with an aldehyde of Formula XXV. The reaction temperature for the second step is conveniently −10° C.-reflux, preferably no higher than 80° C., more preferably 20°–30° C., the initial reaction temperature preferably being −10°–0° C., e.g., 0° C., the reaction time conveniently being 2–24 hours. The reaction solvent is conveniently the same as that utilized in the first step. The molar ratio of the aldehyde of Formula XXV to the phosphonium compound of Formula XXIV is conveniently 1–1.1:1. The product is a mixture of the compound having a trans double bond (the (E) compound) and the compound having a cis double bond (the (Z) compound), of which the former predominates. The (E) and (Z) compounds may be separated by conventional means and separately employed in the succeeding reactions or the mixture may be carried through the remaining reactions of Reaction Scheme V to obtain a mixture of the (E) and (Z) compounds of Formula XXIX which may be separated by conventional means, e.g., column chromatography or high pressure liquid chromatography. Alternatively, the (E) and (Z) compounds may be separated after Reaction X or Reaction Y.

The methoxy group on the tetrahydropyran ring of the compound of Formula XXVI is hydrolyzed to a hydroxy group with acid in Reaction X. The hydrolysis is conveniently carried out in an aqueous inert organic solvent containing an organic or mineral acid. e.g., a mixture of 10% hydrochloric acid and tetrahydrofuran or, preferably, 3:2:1 (by volume) glacial acetic acid/tetrahydrofuran/water at a temperature of 10°–100° C., preferably 60° C. with the latter acid system. While the reaction time is inversely related to the reaction temperature, a reaction time of 8–24 hours is generally acceptable, for example 18–19 hours when the reaction temperature is 60° C. This reaction is accompanied by some epimerization at the 6-carbon atom of the lactone ring. The use of aqueous hydrochloric acid results in more epimerization than does the use of a mixture of acetic acid, tetrahydrofuran and water.

In Reaction Y the hydroxypyran of Formula XXVII is oxidized to the lactone of Formula XXVIII under very mild conditions as is known in the art. For example, the compound of Formula XXVII is treated with 1–6, preferably 2–6, especially 2–5, moles of anhydrous N-methylmorpholine-N-oxide per mole of the compound of Formula XXVII and a catalytic amount of dichlorotris(triphenylphosphine)ruthenium II (e.g., 0.01–0.1, preferably 0.05–0.07, moles per mole of the compound of Formula XXVII) at 0°–40° C., preferably 20°–30° C., in an anhydrous inert organic solvent, e.g., dimethylformamide or, preferably, acetone, for 5–60 minutes, preferably under an inert atmosphere. (See Sharpless et al., Tetrahedron Letters 1976, 2503–2506.) Alternatively, an excess of silver carbonate on Celite may be utilized. Suitable solvents include hydrocarbons such as benzene, toluene and the xylenes. The reaction temperature is conveniently 0° C.-reflux, preferably no higher than 150° C., more preferably 100° C.-reflux, and the reaction time is conveniently 1–18 hours.

In Reaction Z, the silyl group of the compound of Formula XXVIII is cleaved under mild conditions with, for example, a fluoride reagent such as tetra-n-butylammonium fluoride in an anhydrous inert organic medium containing glacial acetic acid, preferably tetrahydrofuran containing 1.2–1.8 moles of glacial acetic acid per mole of the fluoride compound. The reaction temperature is suitably 20°–60° C., preferably 20°–30° C., and the reaction time is suitably 2–24 hours, particularly when the reaction temperature is 20°–30° C. Conveniently, 1–4 moles of fluoride reagent per mole of compound of Formula XXVIII are utilized.

Reaction AA is also a three-step Vilsmeir-Haack reaction. In the exothermic initial step, the phosphorus oxyhalide of Formula XXIIB, preferably phosphorus oxychloride, is reacted with the 3-dialkylaminoacrolein of Formula XXIID, preferably 3-dimethylaminoacrolein, to form an iminium salt. The reaction temperature is suitably −10°–25° C., preferably −10°–5° C., and the reaction time is suitably 5–40 minutes, preferably 10–30 minutes. The reaction is carried out in a lower alkyl nitrile, preferably acetonitrile. Suitably, 1–5 moles, preferably 2–4 moles, of the phosphorus oxyhalide and the 3-dialkylaminoacrolein per mole of the indole of Formula XXIIA to be utilized in the second step are utilized. In the second step, the iminium salt of the first step is reacted with the indole of Formula XXIIA at, preferably, a temperature of 60°–100° C., more preferably 65°–85° C., for, preferably, 5–30 hours, more preferably 6–24 hours. The second step is carried out in the same solvent as the first step, both steps being carried out under anhydrous conditions and an inert atmosphere. In the third step, which is very exothermic, the adduct produced in the second step is decomposed with, for example, an aqueous base, preferably aqueous sodium or potassium hydroxide, preferably at 20°–45° C., more preferably 20°–30° C., in a manner similar to the third step of Reaction R. As in the case of Reaction R, it is preferable to employ at least 4, more preferably 4–6, and most preferably 4, equivalents of the base per mole of the phosphorus oxyhalide.

Reactions BB, CC and DD are three-step reactions for converting the aldehyde of Formula XIX, XXIXB or XXIXC to the aldehyde of Formula XXIXB, XXIXC or XXIXD, respectively. In the first step, the compound of Formula XXIXA is reacted with a strong base such as phenyllithium, n-butyllithium, sodium hydride or potassium t-butoxide to form $(C_6H_5)_3P=CH-OCH_3$ in an anhydrous inert organic solvent, for example, tetrahydrofuran, diethyl ether or bis(2-methoxyethyl) ether under an inert atmosphere for 1.5–4 hours. 1–1.03 moles of the strong base per mole of the compound of Formula XXIXA are conveniently utilized. The obtained $(C_6H_5)_3P=CH-OCH_3$ is reacted with the aldehyde of Formula XIX, XXIXB or XXIXC, as the case may be, in the second step (to obtain an enolether) in an anhydrous inert organic solvent, conveniently the solvent utilized in the first step at −50°–25° C., preferably −20°–10° C., for 10–24 hours. Conveniently, 1–1.05 moles of $(C_6H_5)_3P=CH-OCH_3$ per mole of the aldehyde of Formula XIX, XXIXB or XXIXC are utilized. The enolether product of the second step is hydrolyzed with an acid to obtain the aldehyde of the Formula XXIXB, XXIXC or XXIXD in the third step. Suitable acids include strong inorganic acids such as 70% aqueous perchloric acid or concentrated hydrochloric acid; a large molar excess of the acid is usually employed. The hydrolysis temperature is conveniently 0°–30° C., the hydrolysis time is conveniently 8–24 hours, and the solvent is conveniently a mixture of the excess aqueous acid and an inert organic solvent, e.g., diethyl ether or tetrahydrofuran.

In Reaction EE the lactone of Formula XCIX is hydrolyzed to the carboxylate salt of Formula C. It is convenient to react the lactone of Formula XCIX with 0.95–1, preferably 0.97–0.99, equivalent of an inorganic base of the formula $M_2^{\oplus}\ominus OH$, preferably sodium hydroxide or potassium hydroxide, per mole of the lactone in an inert aqueous organic solvent, preferably a mixture of water and a lower alkanol, e.g., methanol or, preferably, ethanol, at, preferably, 20°–75° C., more preferably 20°–70° C., for, preferably, 1–6 hours, more preferably 1–4 hours, to obtain the carboxylate salt. As is evident to those in the art, a racemic cis lactone of Formula XCIX yields a racemic threo carboxylate salt of Formula C and a racemic trans lactone of Formula XCIX yields a racemic erythro carboxylate salt of Formula C. Likewise, if a single enantiomer of the lactone of Formula XCIX is utilized, a single enantiomer of the carboxylate salt of Formula C is obtained. For example, if a 4R,6S lactone is utilized, the product is the 3R,5S carboxylate salt.

Reactions AB–AG are carried out essentially as described in detail in copending application Ser. No. 427,605, filed Sept. 29, 1982 by James R. Wareing and titled Preparation of Tetrahydropyranone Derivatives, and Reactions AH and AI may be carried out as described in detail in said application.

However, it is preferable to utilize 70% aqueous trifluoroacetic acid for Reaction AH, the cleavage of the trityl group. This reaction is preferably carried out in methylene chloride under an inert atmosphere utilizing 1–1.25, more preferably 1.1–1.2, moles of trifluoroacetic acid per mole of the compound of Formula CVII. The reaction is commenced at −80°––50° C., preferably −55° C., the temperature is allowed to rise to −10°-0° C. over a period of 1 hour, and the reaction mixture is stirred at 0°–10° C. for 3 hours. It is preferred to terminate the reaction when only about 80% of the compound of Formula CVII has reacted in order to minimize byproduct formation.

It is preferred to carry out Reaction AI, the oxidation of the hydroxymethyl group to the formyl group, with pyridinium chlorochromate or, especially, chromium trioxide. When pyridinium chlorochromate is utilized, it is preferable to utilize 1.5–2.5, more preferably 2, moles thereof per mole of the compound of Formula CVIII, and the reaction is preferably carried out in an anhydrous halogenated lower alkane such as methylene chloride under an inert atmosphere, a suitable reaction temperature being 20°–30° C. and a suitable reaction time being 2.5–3.5 hours. When chromium trioxide is utilized, the reaction is carried out under Collins oxidation conditions. It is preferable to utilize 5–10, more preferably 6, moles of chromium trioxide (preferably complexed with pyridine, more preferably 2 moles of pyridine is complexed with one mole of chromium trioxide) per mole of the compound of Formula CVIII, and the reaction is run in an anhydrous halogenated lower alkane, such as methylene chloride, optionally containing some (e.g., 1 mole per mole of chromium trioxide) pyridine. A suitable reaction time is 2.5–3.5 hours, preferably 3 hours, and a suitable reaction temperature is 20°–30° C.

The preferred reaction conditions for Reactions AB–AI are:
AB: (1) sodium, methanol, 20° C., 15 minutes; (2) mercuric acetate, 25° C., 4 hours.
AC: sodium chloride, sodium borohydride, methanol+isopropanol, 20° C., 4 hours.
AD: triphenylmethyl chloride, pyridine, 35° C., 30 hours.
AE: (1) sodium hydride, tetrahydrofuran, 20° C., 3 hours; (2) 1-(2',4',6'-triisopropylphenylsulfonyl)imidazole, −30°→20° C., 2 hours.
AF: lithium aluminum hydride, methyl t-butyl ether, −10° C., 16 hours.
AG: t-butyldiphenylchlorosilane, imidazole, N,N-dimethylformamide, 20° C., 18 hours.
AH: 70% aqueous trifluoroacetic acid, methylene chloride, −55°→0°-10° C., 4 hours.
AI: chromium trioxide/pyridine, pyridine, methylene chloride, 25° C., 3 hours.

The reaction conditions set forth above for Reactions AB–AG should be read in conjunction with Steps A–F of Example 1 of said application Ser. No. 427,605. Steps A–H of said Example 1 on pages 15–24 of said application are hereby incorporated by reference.

Reaction AJ is a conventional oxidation of an alcohol to a ketone. Suitable oxidants and reaction conditions include those set forth above for Reaction AI.

Reaction AK is a conventional reduction of a ketone to an alcohol. Suitable reducing agents and conditions include those set forth above for Reactions B (non-stereoselective) and S, sodium borohydride being a preferred reducing agent. A mixture of the alcohols of Formulae CVI and CXI is produced. The mixture may be separated by conventional means, e.g., high pressure liquid chromatography or column chromatography, or the mixture may be utilized in the succeeding reactions (Reactions AG/AG', AH/AH', AJ/AJ', W, X, etc.) to obtain a mixture of products, with the products separated by conventional techniques after any reaction, as may be desired or convenient.

Reactions AG'–AI' may be carried out as described above and in said application Ser. No. 427,605 for Reactions AG–AI, respectively.

The compounds of Formulae IVA, IVB, XA, XB, XIA, XVII, XVIIIA–XVIIIC, XIXA, XXI, XXIIA–XXIID, XXIXA and CI and the reagents not designated by a Roman numeral (e.g., 1-(2',4',6'-triisopropylphenylsulfonyl)imidazole) are known or, if unknown, may be synthesized by processes analogous to those described in the literature for similar known compounds. Compound CI is commercially available tri-O-acetyl-D-glucal. As for the compound of Formula XXV, one isomer is disclosed in Yang et al., Tetrahedron Letters 23, 4305–4308 (1982), another is disclosed in said application Ser. No. 427,605 and in Reaction Scheme IX and the synthesis of a third isomer is disclosed in Reaction Scheme IX. The isomer of Yang et al. and the isomer disclosed in application Ser. No. 427,605 (and in Reaction Scheme IX) yield compounds of Formula XXIX having the 4R,6S configuration and, as a result of epimerization in Reaction X, compounds of said formula having the 4R,6R configuration. Compounds of Formula XXIX having the 4S,6R and 4S,6S configuration may be obtained from the other isomer whose synthesis is disclosed in Reaction Scheme IX.

Since optically pure compounds of Formula XXV are available, Reaction Scheme V may be utilized to obtain optically pure compounds of Formula XXIX which may be converted into optically pure compounds of Formula VII by Reaction Scheme VIII. Reactions D and K may be utilized to convert the obtained optically pure compounds of Formula VII to the corresponding compounds having another $R_7$ group.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure liquid chromatography. Often, however, the crude product of one reaction may be employed in the following reaction without purification.

As is evident to those in the art, each of the compounds of Formulae V, X and XI has a single center of asymmetry and, therefore, may be resolved into two optically active isomers. When a compound of Formula V or XI is converted into a compound of Formula VI or XII, respectively, an additional center of asymmetry is generated. Consequently, when a racemic compound of Formula V or XI is utilized, four stereoisomers (two pairs of diastereoisomers) of the resulting compound of Formula VI or XII are formed, whereas when an optically pure compound of Formula V or XI is utilized, two diastereoisomers of the compound of Formula VI or XII are formed.

The compounds of Formulae I, VI–IX and XII–XVI have two centers of asymmetry and, therefore, exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) or four (if formed from a racemic compound having one center of asymmetry) stereoisomers.

The obtained mixtures of stereoisomers may be separated by conventional means. For example, diastereoisomers may be separated by fractional crystallization, column chromatography, preparative thin layer chromatography and high pressure liquid chromatography. Each compound of Formula IX may, for example, be separated by the high pressure liquid chromatography technique into its cis and trans components (Formulae IXc and IXt, respectively), each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts or amides that may be separated by fractional crystallization or it may be reacted with an optically pure alcohol having at least one center of asymmetry to form a mixture of diastereoisomeric esters which may be separated by conventional techniques such as those set forth above. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, preferably (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula IX, especially of Formula IXt, may be separated on a silica column (e.g., having an internal diameter of 1 cm. and a length of 25 cm.) having covalently bound L-phenylglycine utilizing, as the eluant, 1:1 (by volume) n-hexane/acetone. After separation, the optically pure salts, amides, esters or silyloxy compounds are reconverted to the corresponding carboxy group- or hydroxy group-containing compounds with retention of optical purity. For example, the process conditions disclosed for Reaction Z may be utilized to cleave (−)-α-naphthylphenylmethylsilyl and other silyl groups.

The compounds of Formula I (and each and every subscope thereof) wherein Z is a group of Formula II and $R_7$ is hydrogen may be converted into the corresponding compounds wherein $R_7$ is a cation, e.g., M, or $C_{1-3}$alkyl, n-butyl, i-butyl, t-butyl or benzyl by conventional means, e.g., Reaction K or by treatment with a base having M as its cation, e.g., a base of the formula $M^{+q}(OH)_q$, wherein q is 1, 2 or 3. Likewise, those wherein Z is a group of Formula II and $R_7$ is any cation, e.g., M, may be converted into the corresponding compounds wherein $R_7$ is hydrogen or any other cation, e.g., M, by conventional means, e.g., Reactions D and J and ion exchange.

Since any compound of Formula I wherein Z is a group of Formula II wherein $R_7$ is a cation other than M may be converted into the corresponding compound wherein $R_7$ is hydrogen, M, $C_{1-3}$-alkyl, n-butyl, i-butyl, t-butyl, or benzyl, the compounds of Formula I wherein Z is a group of Formula II and $R_7$ is a pharmaceutically unacceptable cation are also within the scope of this invention since they are useful as intermediates. However, such compounds are not compounds of Formula I as utilized in this application, except where indicated to the contrary.

Besides having the utility set forth below, every compound of Formula I is useful as an intermediate in the synthesis of one or more other compounds of Formula I utilizing the reactions set forth above. Reactions C–E and J–L may be utilized to convert compounds of Formula I wherein Z is a group of Formula II into the corresponding compounds wherein Z is a group of Formula III and, as set forth above, into the corresponding compounds wherein Z is a group of Formula II having a different $R_7$ group and Reaction EE may be utilized to convert compounds of Formula I wherein Z is a group of Formula III into corresponding compounds wherein Z is a group of Formula II.

Also within the scope of this invention are the intermediates of Formulae V, X, XI, XII, XX, XXIV, XXVI–XXVIII and XXIXB–XXIXD. The preferences for each variable are the same as those set forth for the compounds of Formula I, with the preferred groups of such compounds including those that correspond to Groups (i)–(xiii) and (xxxix)–(xxxviii) (for Formulae V, X–XII, XX, XXIV and XXIXB–XXIXD) and Groups (xiv)–(xx), (xxxiii)–(xxxviii) and (lxxxix)–(cxiv) (for Formulae XXVI–XXVIII) to the extent consistent therewith.

The entire specification of parent application Ser. No. 443,668 (particularly pages 1–29, 34–36 and 49–66, especially pages 1–7) is hereby incorporated by reference as if completely set forth herein.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and anti-atherosclerotic agents. The biological activity of the compounds of Formula I is demonstrated in the following three tests:

Test A: In Vitro Microsomal Assay of HMG-CoA Reductase Inhibition:

200 μl. aliquots (1.08-1.50 mg./ml.) of rat liver microsomal suspensions, freshly prepared from male Sprague-Dawley rats (150-225 g. body weight), in Buffer A with 10 mmol. dithiothreitol are incubated with 10 μl. test substance dissolved in dimethylacetamide and assayed for HMG-CoA reductase activity as described by Ackerman et al., J. Lipid Res. 18,408-413 (1977). In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reaction from the substrate, [$^{14}$C]HMG-CoA. [$^{3}$H]mevalonolactone is added as an internal reference. Inhibition of HMG-CoA reductase is calculated from the decrease in specific activity [$^{14}$C/$^{3}$H]mevalonate) of test groups compared to controls.

Test B: In Vitro Cell Culture Cholesterol Biosynthesis Screen:

The cell culture is prepared as follows:. Stock monolayer cultures of the Fu5AH rat hepatoma cell line (originally obtained from G. Rothblat; see Rothblat, Lipids 9, 526-535 (1974)) are routinely maintained in Eagle's Minimum Essential Medium (EMEM) supplemented with 10% fetal bovine serum (FBS) in 75 cm.$^2$ tissue culture flasks. For these studies, when the cultures reach confluence, they are removed by mild enzymatic treatment with 0.25% trypsin in Hanks' balanced salt solution (without calcium and magnesium). After centrifugation of the cell suspension and aspiration of the enzymatic solution, the cell pellet is resuspended in an appropriate volume of media for seeding into 60 mm. tissue culture dishes. The cultures are incubated at 37° C. in an atmosphere of high humidity and 5% carbon dioxide. When the cultures are confluent (approximately 5 days), they are ready for use. The culture media is aspirated from the dishes and replaced with 3 ml. of EMEM supplemented with 5 mg./ml. of delipidized serum protein (DLSP) prepared by the method of Rothblat et al., In Vitro 12, 554-557 (1976). Replacement of the FBS with DLSP has been shown to stimulate the incorporation of [$^{14}$C]acetate into sterol by removing the exogenous sterol supplied by the FBS, thereby requiring the cells to synthesize sterol. Enhanced 3-hydroxy-3-methylglutaryl Coenzyme A reductase (HMG-CoA reductase) activity is measurable in the cells in response to the lack of exogenous sterol. Following approximately 24 hours incubation at 37° C. in the DLSP supplemented media, the assay is initiated by the addition of 3 μCi of [$^{14}$C]acetate and the test substances solubilized in dimethylsulfoxide (DMSO) or distilled water. Solvent controls and compactin-treated controls are always prepared. Triplicate 60 mm. tissue culture dishes are run for each group. After 3 hours incubation at 37° C., the cultures are examined microscopically using an inverted phase contrast microscope. Notations are made of any morphological changes which may have occurred in the cultures. The media is aspirated and the cell layer is gently washed twice with 0.9% sodium chloride solution (saline). The cell layer is then harvested in 3 ml. of 0.9% saline by gentle scraping with a rubber policeman and transferred to a clean glass tube with Teflon lined cap. The dishes are rinsed with 3 ml. of 0.9% saline and rescraped, and the cells are combined with the first harvest. The tubes are centrifuged at 1500 r.p.m. for 10 minutes in an IEC PR-J centrifuge, and the supernatant is aspirated.

The cells are then extracted as follows: One ml. of 100% ethanol is added to the cell pellet followed by sonication for 10 seconds with a "LO" setting of 50 on a Bronwell Biosonik IV. One hundred μl. are taken for protein determination. One ml. of 15% potassium hydroxide (KOH) is added, and the samples are thoroughly vortexed. Saponification is accomplished by heating the ethanol-KOH treated samples at 60° C. for 60 minutes in a water bath. Following dilution of the samples with 2 ml. of distilled water, they are extracted three times with 7 ml. of petroleum ether. The petroleum ether extracts are then washed three times with 2 ml. of distilled water and finally taken to dryness under a stream of nitrogen.

The obtained samples are then analyzed by thin layer chromatography (TLC) as follows: Residues from the petroleum ether extraction are taken up in a small volume of hexane and spotted on silica gel 60 TLC plates (E. Merck). Development of the plates is carried out in a 150 parts by volume hexane: 50 parts by volume diethyl ether: 5 parts by volume glacial acetic acid solvent system using a three phase development procedure. Visualization is accomplished in an iodine vapor chamber. The plates are divided into five sections such that each section contains the molecules having the following approximate Rf values: section 1—0-0.4, section 2—0.4-0.55, section 3—0.55-0.7, section 4—0.7-0.9 and section 5—0.9-1.0. Section 2 contains the non-saponifiable sterols. The five sections of the TLC plates are scraped into scintillation vials. Blanks are also prepared from scrapings of chromatographed non-labelled standards. ACS TM scintillation cocktail is added, and the radioactivity is determined in a liquid scintillation spectrometer. [$^{14}$C]hexadecane standards are used to determine counting efficiencies. The total protein content of the samples is determined employing the Bio-Rad Protein Assay System.

The results are reported as disintegrations per minute per mg. protein (d.p.m./mg. protein) for each of the five TLC sections. Mean d.p.m./mg. protein±standard error of the mean are calculated, and drug treated means are compared for percentage change (%Δ) and statistical significance with solvent control means. TLC section 2 data is taken as a measure of HMG-CoA reductase activity inhibition.

Test C: In Vivo Cholesterol Biosynthesis Inhibition Test: In vivo studies utilize male Wistar Royal Hart rats weighing 150±20 g. which have been kept for 7-10 days on an altered light cycle (6:30 A.M.-6:30 P.M. dark) housed two per cage and fed powdered Purina Rat Chow and water ad libitum. Three hours before the diurnal maximum of cholesterol synthesis at mid-dar, the rats are administered the test substances dissolved or as a suspension in 0.5% carboxymethylcellulose in a volume of 1 ml./100 g. body weight. Controls receive vehicle alone. One hour after receiving the test substance, the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia and the serum separated by centrifugation.

Serum samples are saponified and neutralized, and the 3β-hydroxy sterols are precipitated with digitonin basically as described by Sperry et al., J. Biol. Chem. 187, 97 (1950). The [$^{14}$C]digitonides are then counted by liquid scintillation spectrometry. After correcting for efficiencies, the results are calculated in nCi (nanocuries) of sterol formed per 100 ml. of serum. Inhibition of sterol synthesis is calculated from the reduction in the nCi of sterols formed from test groups compared to controls.

The following results were obtained:

| | Test A: | |
|---|---|---|
| Example 1 | $IC_{50}$ = 1.7 | μmolar |
| Example 3 | $IC_{50}$ = 1.66 | μmolar |
| Example 4 (a) | $IC_{50}$ = 0.79 | μmolar |
| Example 8 | $IC_{50}$ = 9.6 | nanomolar |
| Example 9 | $IC_{50}$ = 0.12 | μmolar |
| Example 10 | $IC_{50}$ = 0.69 | μmolar |
| Example 12 | $IC_{50}$ = 9.1 | μmolar |
| Example 23 | $IC_{50}$ = 0.09 | μmolar |
| Example 43 | $IC_{50}$ = 9.6 | μmolar |
| Example 54 | $IC_{50}$ = 464 | μmolar |
| Example 60 | $IC_{50}$ = 0.12 | μmolar |
| Example 64 | $IC_{50}$ = 0.011 | μmolar |
| Example 75 | $IC_{50}$ = 5.4 | nanomolar |
| Example 89 | $IC_{50}$ = 9.3 | μmolar |
| Example 102 | $IC_{50}$ > 1000 | μmolar |
| Example 113 | $IC_{50}$ = 0.03 | μmolar |
| Example 132 | $IC_{50}$ = 1.62 | μmolar |
| Example 142 | $IC_{50}$ = 1.3 | μmolar |
| Compactin | $IC_{50}$ = 0.5 | μmolar |
| | Test B: | |
| Example 1 | $IC_{50}$ = 0.8 | μmolar |
| Example 3 | $IC_{50}$ = 0.8 | μmolar |
| Example 4 (a) | $IC_{50}$ = 0.62 | μmolar |
| Example 8 | $IC_{50}$ = 0.05 | μmolar |
| Example 9 | $IC_{50}$ = 0.22 | μmolar |
| Example 10 | $IC_{50}$ = 0.42 | μmolar |
| Example 12 | −16% at 1 | μmolar |
| Example 21 | $IC_{50}$ = 0.2 | μmolar |
| Example 23 | $IC_{50}$ = 0.6 | μmolar |
| Example 43 | $IC_{50}$ = 0.74 | μmolar |
| Example 64 | $IC_{50}$ = 0.03 | μmolar |
| Example 111 | $IC_{50}$ = 0.19 | μmolar |
| Example 132 | −71% at 10 | μmolar |
| Example 142 | $IC_{50}$ = 1.5 | μmolar |
| Compactin | $IC_{50}$ = 0.06 | μmolar |

$IC_{50}$ is the concentration of the test substance in the assay system calculated to produce a 50% inhibition of HMG-CoA reductase activity (Test A) or sterol biosynthesis (Test B).

| | Test C: | |
|---|---|---|
| Example 1 | $ED_{50}$ = 5.7 | mg./kg. |
| Example 3 | $ED_{50}$ > 10 | mg./kg. |
| Example 4 (a) | $ED_{50}$ = 5.2 | mg./kg. |
| Example 8 | $ED_{50}$ = 0.03 | mg./kg. |
| Example 9 | −63% at 2 | mg./kg. |
| Example 10 | −47% at 4 | mg./kg. |
| Example 21 | $ED_{50}$ = 10.4 | mg./kg. |
| Example 60 | −71% at 1 | mg./kg. |
| Example 64 | −57% at 1 | mg./kg. |
| Example 113 | −64% at 1 | mg./kg. |
| Example 132 | −35% at 10 | mg./kg. |
| Example 142 | −84% at 10 | mg./kg. |
| Compactin | $ED_{50}$ = 4.4 | mg./kg. |
| Mevinolin | $ED_{50}$ = 0.48 | mg./kg. |

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and anti-atherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means. The preferred pharmaceutical compositions from the standpoint of ease of preparation and administration are solid compositions, particularly tablets and capsules.

The precise dosage of the compound of Formula I to be employed for inhibiting cholesterol biosynthesis depends upon several factors including the host, the nature and the severity of the condition being treated, the mode of administration and the particular compound employed. However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 0.01–100, preferably 0.1–25, mg./kg. body weight or, for most larger primates, a daily dosage of 1–2000 mg., preferably 1.5–100 mg. For the compound of Example 8, the oral daily dosage is indicated to be 0.01–10 mg./kg. body weight, preferably 0.1–5 mg./kg. body weight, or, for most larger primates, it is indicated to be 0.1–140 mg. and preferably 1.5–10 mg.

The daily dosage is usually divided into two to four equal portions or administered in sustained release form. A typical oral dosage of the compound of Example 8 is indicated to be 1 mg. three times a day. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 0.5 to 500 mg. of a compound of Formula I. Preferred dosage units contain 0.5 to 50 mg., especially 0.5 to 25 mg., of a compound of Formula I.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

Representative formulations preparable by conventional techniques for encapsulation in a hard gelatin capsule are:

| A. | Compound of Formula I, e.g., the compound of | |
|---|---|---|
| | Example 4 (a) | 10 mg. |
| | Lactose (spray-dried) | 90 mg. |

-continued

| | | |
|---|---|---|
| B. | Compound of Formula I, e.g., the compound of | |
| | Example 1 | 25 mg. |
| | Peanut oil | to 0.25 ml. |
| C. | Compound of Formula I, e.g., the compound of | |
| | Example 8 | 1 mg. |
| | Corn stach | 248 mg. |
| | Magnesium stearate | 1 mg. |

Representative formulations suitable for preparing tablets by conventional means are:

| | | |
|---|---|---|
| A. | Compound of Formula I, e.g., the compound of | |
| | Example 3 | 25 mg. |
| | Gum tragacanth | 5 mg. |
| | Powdered lactose | 98.5 mg. |
| | Corn starch | 12.5 mg. |
| | Talc | 7.5 mg. |
| | Magnesium stearate | 1.5 mg. |
| B. | Compound of Formula I, e.g., the compound of | |
| | Example 8 | 2 mg. |
| | Polyvinylpyrrolidone USP | 5 mg. |
| | Powdered lactose | 82 mg. |
| | Corn starch | 10 mg. |
| | Magnesium stearate | 1 mg. |

The following examples show representative compounds encompassed by this invention and their synthesis. However, it should be understood that they are for purposes of illustration only.

EXAMPLE 1

Methyl (E)-3,5-dihydroxy-7-[3'-(4''-fluorophenyl)-1'-methylindol-2'-yl]hept-6-enoate (XXX)

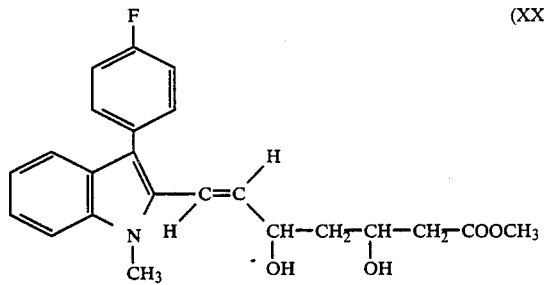

Step 1 (Reaction Q)
Ethyl 3-(4'-fluorophenyl)-1-methylindole-2-carboxylate

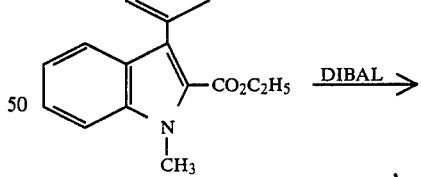

(XXXI)

(XXXII)

To a solution of 8.0 g. (28 mmol.) of ethyl 3-(4'-fluorophenyl)indole-2-carboxylate in 30 ml. of dry dimethylacetamide stirred under nitrogen at −10° C., 1.6 g. (33 mmol.) of sodium hydride is added. The reaction mixture is stirred at −10° C. under nitrogen for 45 min., 4.8 g. (32 mmol.) of methyl iodide is added at −10° C., and the reaction mixture is allowed to warm to room temperature and stirred under nitrogen at room temperature for 2 hrs. The reaction mixture is poured into 400 ml. of ice/water, neutralized with 4 ml. of 2N. hydrochloric acid and extracted several times with diethyl ether. The diethyl ether extracts are combined, washed with water, washed with saturated sodium chloride solution, dried over anhydrous magnesium sulfate, filtered and evaporated at reduced pressure. The residue is purified by column chromatography utilizing a silica gel column and chloroform as the eluant. The fractions containing the product are combined and evaporated at reduced pressure, and the residue is crystallized from n-hexane/petroleum ether to obtain the product (7.6 g. (91%)), m.p. 61°–62° C.

Step 2 (Reaction M)
3-(4'-Fluorophenyl)-2-hydroxymethyl-1-methylindole (XXXII)

(XXXIII)

To a solution of 20.0 g. (67 mmol.) of Compound XXXII in 500 ml. of dry tetrahydrofuran stirred at −78° C. under nitrogen, 80 ml. of 25% (by weight) diisobutylaluminum hydride/toluene is added, and the reaction mixture is stirred at −78° C. under nitrogen for 4 hrs. The reaction mixture is allowed to warm to −10° C., an additional 30 ml. of 25% (by weight) diisobutylaluminum hydride/toluene is added, the reaction mixture is stirred at 0° C. under nitrogen for an additional 3 hrs., a further 30 ml. of 25% (by weight) diisobutylaluminum hydride/toluene is added, and the reaction mixture is stirred at 0° C. under nitrogen for a further 1 hr. The reaction mixture is treated with saturated ammonium chloride solution and filtered, and the organic layer is separated, dried over anhydrous magnesium sulfate, filtered and evaporated at reduced pressure. The residue is triturated with n-hexane to obtain the product (17.0 g. (100%)), m.p. 99°–104° C.

Step 3 (Reaction N)

3-(4′-Fluorophenyl)-1-methylindole-2-carboxaldehyde

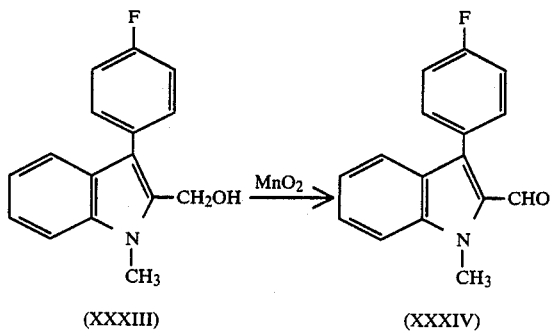

(XXXIII)    (XXXIV)

A mixture of 17.0 g. (67 mmol.) of Compound XXXIII, 90.0 g. (1.03 mol.) of manganese dioxide and 1.2 l. of anhydrous diethyl ether is stirred at room temperature under nitrogen for 14 hrs. The reaction mixture is filtered and the diethyl ether is evaporated at reduced pressure. The residue is flash chromatographed on a silica gel column using methylene chloride as the eluant, the fractions containing the product are combined and evaporated at reduced pressure, and the residue is triturated with n-pentane to obtain the product (12.2 g. (72%)), m.p. 75°–79° C.

Step 4 (Reaction O)

(E)-3-[3′-(4″-Fluorophenyl)-1′-methylindol-2′-yl]propenaldehyde

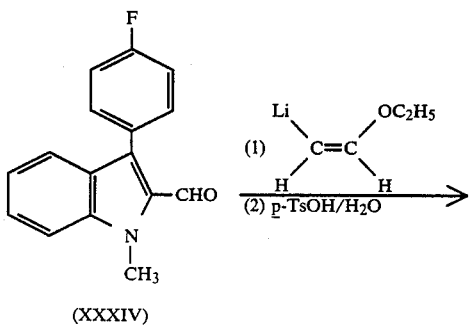

(XXXIV)

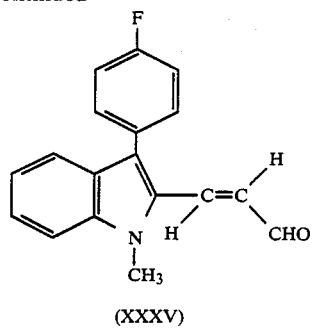

(XXXV)

25 ml. of 1.7M. n-butyllithium/n-hexane (42 mmol.) is added dropwise to a solution of 14.5 g. (40 mmol.) of tri-n-butylstannylvinylethoxide in 600 ml. of dry tetrahydrofuran stirred at −78° C. under nitrogen, stirring is maintained for 2 hrs. under the same conditions, and 9.0 g. (35.6 mmol.) of Compound XXXIV, dissolved in 60 ml. of dry tetrahydrofuran, is added rapidly dropwise. The reaction mixture is stirred at −78° C. under nitrogen for 3.5 hrs., quenched with 60 ml. of saturated ammonium chloride solution and extracted several times with diethyl ether. The diethyl ether extracts are combined, washed with water, washed with saturated sodium chloride solution, dried over anhydrous magnesium sulfate, filtered and evaporated at reduced pressure. The residue is partitioned between n-hexane and acetonitrile (to remove the organotin compounds), and the acetonitrile layer is evaporated at reduced pressure to obtain an oil. The oil is dissolved in 300 ml. of tetrahydrofuran, 50 ml. of water and 30 mg. of p-toluenesulfonic acid monohydrate are added, and the reaction mixture is stirred for 2 hrs. at room temperature and then extracted several times with diethyl ether. The diethyl ether extracts are combined, washed with water, washed with saturated sodium chloride solution, dried over anhydrous magnesium sulfate, filtered and evaporated to dryness at reduced pressure. The residue is triturated with n-hexane/diethyl ether to obtain the product (5.3 g.), m.p. 110°–112° C. A subsequent batch melted at 115°–118° C.

N.M.R. (CDCl$_3$, 3.97, (3H singlet); 90 MHz) 6.55, (1H doublet of a doublet); 7.10–7.70, (9H multiplet); 9.56, (1H doublet).

Step 5 (Reaction A)

Methyl (E)-7-[3′-(4″-fluorophenyl)-1′-methylindol-2′-yl]-5-hydroxy-3-oxohept-6-enoate

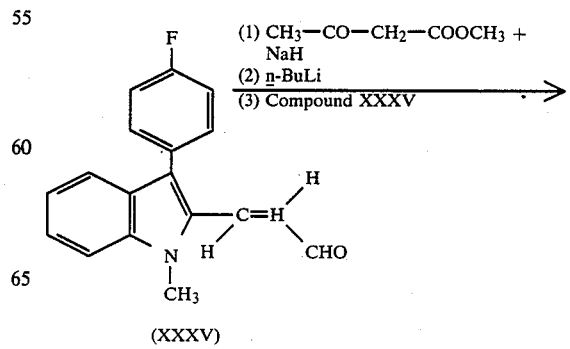

(XXXV)

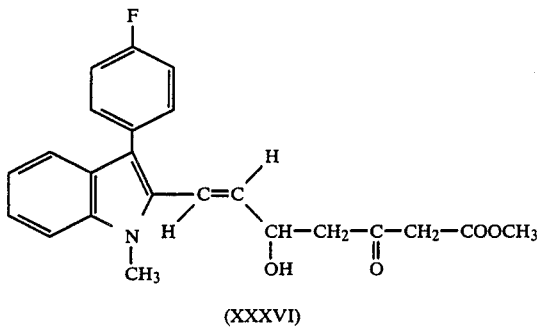

(XXXVI)

3.5 ml. (32.4 mmol.) of methyl acetoacetate is added dropwise to a suspension of 1.6 g. of 50% (by weight) sodium hydride (33.3 mmol.) in 400 ml. of dry tetrahydrofuran stirred at −15° C. under nitrogen. The reaction mixture is stirred at −15° C. under nitrogen for 20 min., 19 ml. of 1.7M. n-butyllithium/n-hexane (31.9 mmol.) is added, the reaction mixture is stirred at −15° C. under nitrogen for 20 minutes, a solution of 5.3 g. (19 mmol.) of Compound XXXV in 100 ml. of dry tetrahydrofuran is added, and the reaction mixture is stirred at −15° C. under nitrogen for 30 min. The reaction mixture is quenched with dilute hydrochloric acid and extracted several times with diethyl ether. The diethyl ether extracts are combined, washed with water, washed with saturated sodium chloride solution, dried over anhydrous magnesium sulfate, filtered and evaporated to dryness at reduced pressure. The residue is triturated with n-pentane (to remove excess methyl acetoacetate) to obtain the crude product as an oil.

The product is a racemate that may be resolved into its d and l components.

Step 6 (Reaction B)

Methyl (E)-3,5-dihydroxy-7-[3'-(4''-fluorophenyl)-1'-methylindol-2'-yl]hept-6-enoate

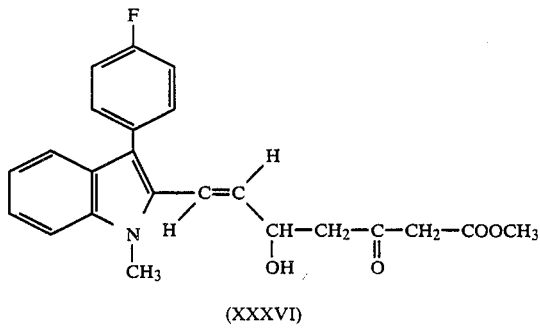

(XXXVI)

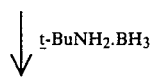

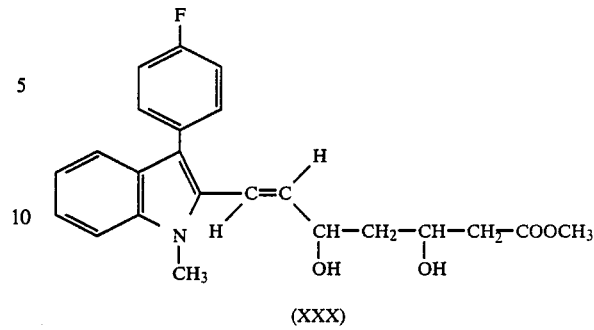

(XXX)

2.0 g. of borane-t-butylamine complex is added to a solution of 8.0 g. (20.2 mmol.?) of crude racemic Compound XXXVI in 200 ml. of absolute ethanol stirred at 0° C. under nitrogen. The reaction mixture is stirred at 0° C. under nitrogen for 3 hrs., and saturated sodium chloride solution is added. The reaction mixture is acidified with dilute hydrochloric acid and extracted several times with diethyl ether. The diethyl ether extracts are combined, washed with water, washed with saturated sodium chloride solution, dried over anhydrous magnesium sulfate, filtered and evaporated to dryness at reduced pressure. The obtained oil is purified by flash chromatography using a silica gel column and 1:1 ethyl acetate/chloroform as the eluant. The product, a mixture of four stereoisomers, is obtained as a yellow oil (6.1 g.).

N.M.R. (CDCl$_3$): 1.5–1.9, (2H multiplet); 2.4–2.6, (2H multiplet); 2.8–3.4, (2H broad peak, exchangeable); 3.7, (3H singlet); 3.8, (3H singlet); 4.26, (1H multiplet); 4.55, (1H multiplet); 5.85–6.1, (1H multiplet); 6.7, (1H two doublets); 7.05–7.55, (8H multiplet).

I.R. (CHCl$_3$): 1710 and 1210 cm.$^{-1}$ and others

The obtained mixture of stereoisomers may be separated by conventional means into two racemic mixtures each of which may be resolved into two optically pure enantiomers. The four isomers may be designated as the 3R,5R, 3S,5S, 3R,5S and 3S,5R isomers. Preferred are the 3R,5R and 3R,5S isomers and the racemate of which each is a constituent, viz., the 3R,5R-3S,5S and the 3R,5S-3S,5R racemate.

EXAMPLE 2

(E)-3,5-Dihydroxy-7-[3'-(4''-fluorophenyl)-1'-methylindol-2'-yl]hept-6-enoic acid (Reactions C and D)

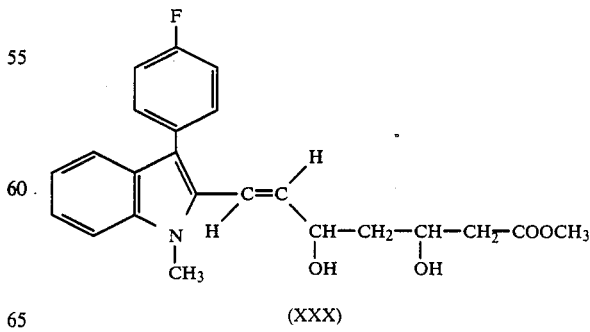

(XXX)

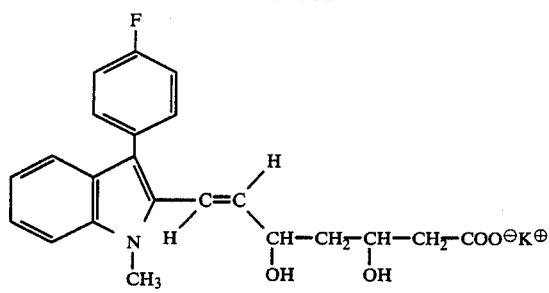

(XXXVII)

↓ H⊕

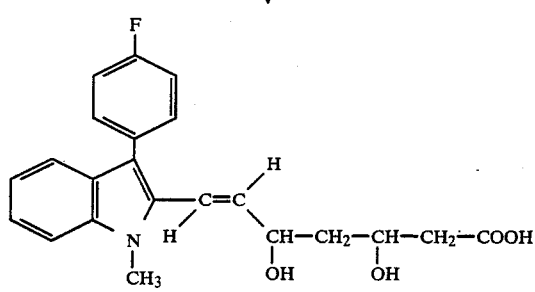

(XXXVIII)

2.8 ml. of 1N. aqueous potassium hydroxide (2.8 mmol.) is added to a solution of 1.1 g. (2.77 mmol.) of Compound XXX in 100 ml. of 95% aqueous methanol stirred at room temperature, and the reaction mixture is stirred at room temperature for 3 hrs. The solvent is evaporated at reduced pressure, the residue (crude Compound XXXVII, a mixture of four stereoisomers) is dissolved in water, and the aqueous solution is extracted with diethyl ether. The aqueous phase is acidified with dilute hydrochloric acid (pH 6.0) and extracted several times with diethyl ether. The diethyl ether extracts are combined, washed with water, washed with saturated sodium chloride solution, dried over anhydrous magnesium sulfate, filtered and evaporated at reduced pressure to give the crude product as a yellow oil. It is a mixture of four stereoisomers.

If desired, Compound XXXVII or Compound XXXVIII may be separated into two racemic mixtures each of which may be resolved into two optically pure enantiomers. The four stereoisomers may be designated as the 3R,5R, 3S,5S, 3R,5S and 3S,5R isomers. Preferred are the 3R,5R and 3R,5S isomers and the racemate of which each is a constituent, viz., the 3R,5R-3S,5S racemate and the 3R,5S-3S,5R racemate.

EXAMPLE 3

(E)-6-[2'-[3''-(4'''-Fluorophenyl)-1''-methylindol-2''-yl]ethenyl]-4-hydroxy-3,4,5,6-tetrahydro-2H-pyran-2-one (Reaction E)

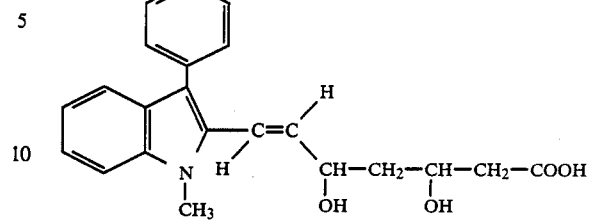

(XXXVIII)

↓ Δ

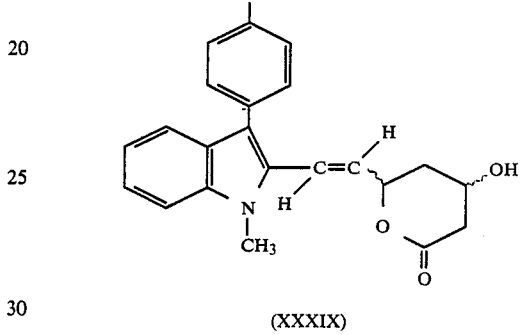

(XXXIX)

A solution of 1.1 g. (2.87 mmol.?) of crude Compound XXXVIII in 50 ml. of dry benzene is refluxed for 8 hrs. The solvent is evaporated at reduced pressure, and the residue is flash chromatographed on a silica gel column utilizing 19:1 chloroform/methanol as the eluant to obtain the product as a mixture of four diastereoisomers (two cis and two trans) (640 mg.).

N.M.R. (CDCl$_3$): 1.6–3.0, (5H multiplet); 3.82, (3H two singlets); 4.39, (1H multiplet); 4.78, (1H two singlets) (cis isomer, C-6 H); 5.30 (1H two signlets) (trans isomer, C-6 H); 5.82–6.0, (1H two overlapping doublets of a doublet); 6.69–6.81, (1H two doublets); 7.05–7.6, (8H multiplet).

I.R. (CHCl$_3$): 3600 (m), 3400 (broad), 3000 (s), 2960 (m), 2930 (m), 1736 (s) and 1220 (s) cm.$^{-1}$ and others

EXAMPLES 4(a) and 4(b)

(E)-Trans-6-[2'-[3''-(4'''-fluorophenyl)-1''-methylindol-2''-yl]ethenyl]-4-hydroxy-3,4,5,6-tetrahydro-2H-pyran-2-one and the corresponding cis lactone

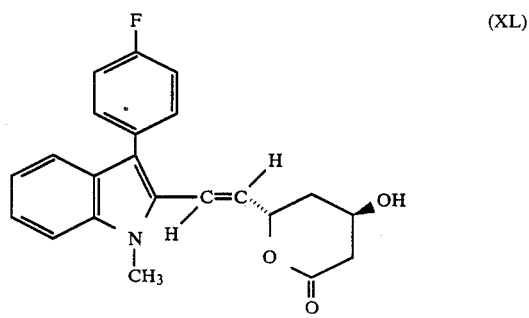

(XL)

and

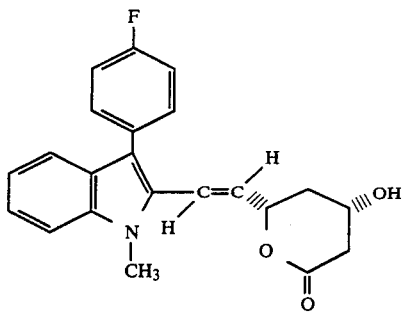

(a) The mixture of isomers obtained in Example 3 is separated by high pressure liquid chromatography using a silica gel column and, as the solvent, 7:2:1 methyl t-butyl ether/n-hexane/acetone to obtain the racemic trans lactone, m.p. 147°–150° C. A subsequent batch melted at 150°–154° C.

N.M.R. (CDCl$_3$): 1.7–2.1, (3H multiplet); 2.55–2.85, (2H multiplet); 3.8, (3H singlet); 4.38, (1H multiplet); 5.30, (1H multiplet); 5.9, (1H doublet of a doublet); 6.72, (1H doublet of a doublet); 7.05–7.6, (8H multiplet).

U.V.: $\lambda_{max}$=278 m$\mu$ 315 m$\mu$

I.R. (CHCl$_3$): 3600 (m), 3010 (s), 2910 (broad), 1710 (s) and 1220 (s) cm.$^{-1}$ and others.

The obtained racemate may be resolved by conventional means into two optically pure enantiomers, the 4R,6S and 4S,6R isomers by, for example, (i) reacting with (−)-α-naphthylphenylmethylchlorosilane, (ii) separating the obtained diastereoisomeric silyloxy compounds and (iii) cleaving the silyl groups with tetra-n-butylammonium fluoride in a mixture of acetic acid and tetrahydrofuran, as set forth above. The amorphous solid 4R,6S enantiomer has an $[\alpha]_D^{25}$= −18.5° (CHCl$_3$, c=0.2 g.). The 4S,6R enantiomer was also an amorphous solid.

(b) The racemic cis lactone may also be isolated from the silica gel column, m.p. 48°–62° C. (dec.). It too may be resolved by conventional means into two optically pure enantiomers. The two stereoisomers may be designated at the 4R,6R and 4S,6S isomers, the former being preferred.

N.M.R. (CDCl$_3$): 1.62–1.78, (1H multiplet); 1.94, (1H doublet); 2.35–2.4, (1H multiplet); 2.52, (1H doublet of a doublet); 2.98, (1H doublet of a doublet); 3.87, (3H singlet); 4.3, (1H multiplet); 4.8, (1H multiplet); 5.95, (1H doublet of a doublet); 6.77, (1H doublet); 7.1–7.6, (8H multiplet).

EXAMPLE 5

Methyl (±)-erythro-(E)-3,5-dihydroxy-7-[3′-(4″-fluorophenyl)-1′-(1″-methylethyl)indol-2′-yl]hept-6-enoate

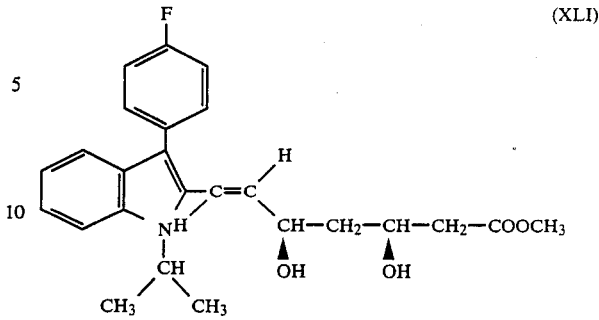

Step 1
4-Chloroacetyl-1-fluorobenzene

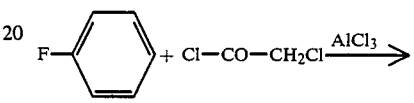

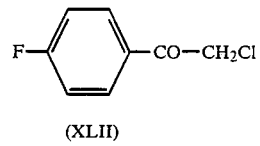

164 ml. (235.1 g., 2.04 moles) of chloroacetyl chloride is added over a 50 min. period to a mixture of 400 ml. (410 g., 4.22 moles) of fluorobenzene and 300 g. (2.25 moles) of anhydrous aluminum chloride stirred at 75° C. under nitrogen. The reaction mixture is stirred at 80° C. under nitrogen for 1 hour, cooled to 50° C., 500 ml. of fluorobenzene is added, and the reaction mixture is cooled to 0° C. and gradually (over a 30 min. period) siphoned into 1 l. of 6N. hydrochloric acid stirred at 0° C. (The temperature of the aqueous acid is maintained at or below 25° C. throughout the addition.) The quenched, acidified reaction mixture is stirred for 15 min., and the aqueous phase is separated and extracted with 350 ml. of fluorobenzene. The two organic phases are combined and washed twice with 500 ml. portions of 3N. hydrochloric acid and once with 500 ml. of water. The fluorobenzene is distilled at 30 mm. Hg. and 60° C. and, upon cooling, the obtained oily residue solidifies. The crude solid product need not be purified.

Step 2
N-(4-Fluorobenzoylmethyl)-N-(1-methylethyl)aniline

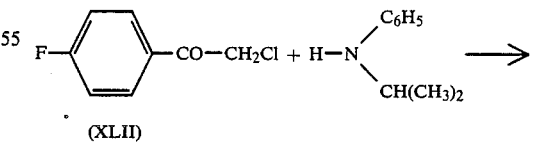

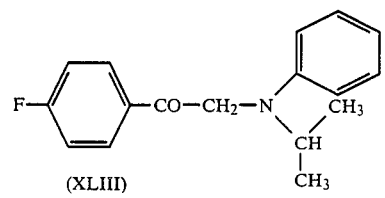

562.9 g. (4.08 moles) of N-isopropylaniline is rapidly added to a solution of the crude product of Step 1 in 500 ml. of dimethylformamide stirred at 50° C. under nitrogen. The reaction mixture is stirred at 100° C. under nitrogen for 10 hours and allowed to cool to room temperature overnight. The reaction mixture is heated to 60° C., 2 l. of water is added, and the mixture is cooled to 10° C. The obtained solids are collected, washed twice with 500 ml. portions of water and dissolved in 550 ml. of 95% ethanol at 75° C. The solution is cooled to 0° C., and the obtained solids are collected, washed three times with 100 ml. portions of 95% ethanol and vacuum dried at 35°-40° C. for 4 hours to obtain the 95.3% pure yellow product (466 g. (84.2% (two steps))), m.p. 78°-81° C.

Step 3

3-(4'-Fluorophenyl)-1-(1'-methylethyl)indole

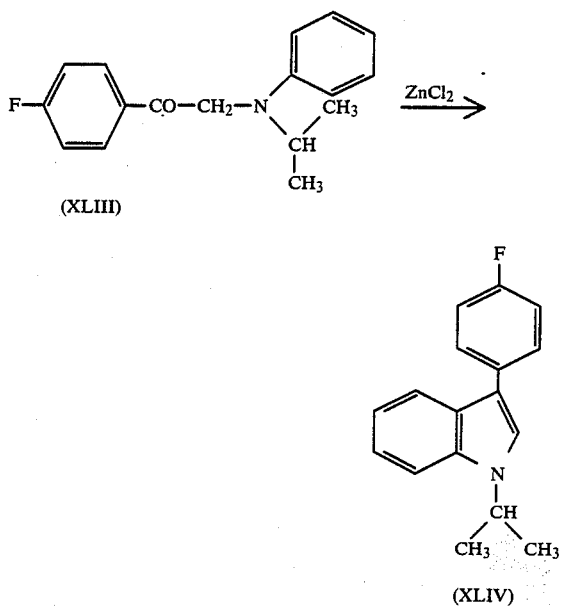

954 g. (7.0 moles) of anhydrous zinc chloride is added portionwise to 1.27 l. of absolute ethanol stirred at room temperature under nitrogen. The addition is exothermic. To the resulting hot (70° C.) solution, 271.3 g. (1.0 mole) of Compound XLIII is added, and the reaction mixture is stirred at 100°-103° C. under nitrogen for 3 hours and cooled to 25° C. 1.5 l. of 1N. hydrochloric acid is added, followed by 1 l. of methylene chloride. The resulting two-phase system is stirred for 5 min., the organic phase is separated, and the aqueous phase is washed twice with 250 ml. portions of methylene chloride. The three methylene chloride phases are combined, the volume is reduced by about 50% by partial evaporation of the methylene chloride at 140 mm. Hg. and 40° C., and 1 l. of 95% ethanol is added. The reaction mixture is distilled at atmospheric pressure until a vapor temperature of 75° C. (pot temperature of 77° C.) is reached and cooled to 0° C. The obtained solids are collected, washed three times with 100 ml. portions of cold ethanol and vacuum dried overnight at room temperature to obtain the 99.9% pure product as a white powder (195 g. (81% corrected for purity of starting material)), m.p. 94.5°-95° C.

Step 4 (Reaction AA)

(E)-3-[3'-(4''-Fluorophenyl)-1'-(1'''-methylethyl)indol-2'-yl]prop-2-enal

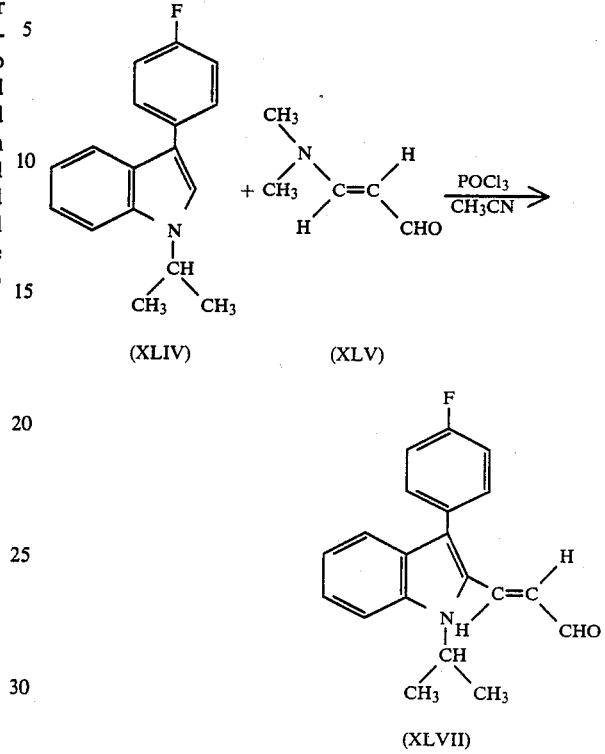

A solution of 50 ml. (49.6 g., 0.5 mole) of 3-N,N-dimethylaminoacrolein (Compound XLV) in 200 ml. of dry acetonitrile is slowly added over a 30 min. period to a solution of 50 ml. (82.5 g., 0.5392 mole) of phosphorus oxychloride in 200 ml. of dry acetonitrile stirred at −10°-0° C. under nitrogen. 45.3 g. (0.1788 mole) of Compound XLIV is added portionwise over a 2 min. period to the reaction mixture stirred at 0°-5° C. The reaction mixture is refluxed for 24 hours under nitrogen, cooled to room temperature and slowly poured (over a 20 min. period) into a cold (10° C.) stirred mixture of 2 l. of toluene and a solution of 130 g. of sodium hydroxide in 2 l. of water so that the temperature does not exceed 26° C. The reaction mixture is filtered to remove the insolubles, and the toluene layer is separated and washed twice with 1 l. portions of water. The additional insolubles are removed by filtration, and the toluene layer is evaporated at reduced pressure and 50°-60° C. The obtained viscous oil is chromatographed on 550 g. of silica gel (20-230 mesh A.S.T.M.) using methylene chloride as the eluant; twenty 100 ml. fractions are collected over a 2 hour period. The fractions containing the desired product (as determined by thin layer chromatography) are combined and evaporated to dryness at reduced pressure and 50°-60° C. to obtain the crude solid product (48.5 g.). The crude product is dissolved in 70 ml. of refluxing absolute ethanol, the obtained solution is cooled to 65° C., 70 ml. of n-heptane is added, and the resulting solution is cooled to −5°-0° C. for 15 min. The precipitated solids are collected by filtration, washed with 20 ml. of ice cold n-heptane and vacuum dried at 50°-55° C. to obtain the yellow product (32.1 g. (58.4%)), m.p. 122°-123° C. A second crop may be obtained. A subsequent batch melted at 129°-132° C.

Step 5 (Reaction A)

Methyl (±)-(E)-7-[3'-(4''-fluorophenyl)-1'-(1''-methylethyl)indol-2'-yl]-5-hydroxy-3-oxohept-6-enoate

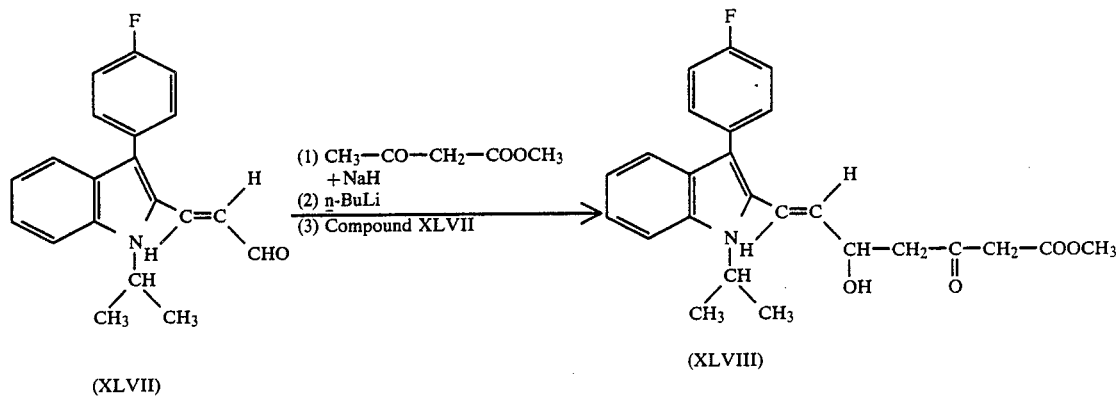

(XLVII)

4.6 ml. (43 mmol.) of methyl acetoacetate is added dropwise to 1.7 g. of n-pentane-washed 60% (by weight) sodium hydride/mineral oil (43 mmol.) in 500 ml. of dry tetrahydrofuran stirred at 0° C. under nitrogen. The reaction mixture is maintained for 20 min., 27.5 ml. of 1.6M. n-butyllithium/n-hexane (44 mmol.) is added dropwise, the reaction mixture is maintained for 20 min., a solution of 8.0 g. (26 mmol.) of Compound XLVII in 200 ml. of dry tetrahydrofuran is rapidly added dropwise, and the reaction mixture is maintained for 30 min., the reaction mixture being stirred at 0° C. under nitrogen throughout. The reaction mixture is quenched with 20 ml. of concentrated hydrochloric acid, poured into 500 ml. of ice cold water and extracted with about 600 ml. of diethyl ether. The diethyl ether extract is washed three times with saturated sodium chloride solution, dried over anhydrous magnesium sulfate and evaporated at reduced pressure to an orange oil. The oil is triturated with n-pentane, the n-pentane is decanted, and the oil is vacuum dried to obtain the crude product (12.2 g. (112%)). Yellow seed crystals of the product were obtained from the n-pentane used in the trituration, m.p. 95°-97° C.

The product is a racemate that may be resolved into its R and S components.

Step 6 (Reaction B)
Methyl (±)-erythro-(E)-3,5-dihydroxy-7-[3'-(4''-fluorophenyl)-1'-(1''-methylethyl)indol-2'-yl]hept-6-enoate

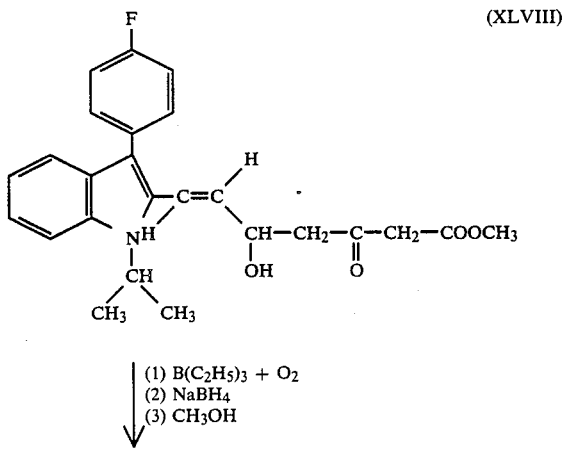

(XLI)

(a) 30 ml. of 1M. triethylborane/tetrahydrofuran (30 mmol.) is added dropwise to a solution of 12.2 g. (26 mmol. assuming 100% yield) of crude Compound XLVIII from Step 5 in 400 ml. of dry tetrahydrofuran (distilled over lithium aluminum hydride) stirred at room temperature, 55 ml. of air (at 760 mm. Hg. and 25° C.) is bubbled through over 5 min., and the reaction mixture is stirred at room temperature under nitrogen for 2 hours. The reaction mixture is cooled to −80° C., 1.3 g. (34 mmol.) of sodium borohydride is added, and the reaction mixture is stirred overnight at −80° C. under nitrogen. The reaction mixture is allowed to warm to −10°-0° C., quenched by the dropwise addition of sufficient 2N. hydrochloric acid to lower the pH to 2 and extracted with diethyl ether. The diethyl ether extract is washed twice with saturated sodium chloride solution, dried over anhydrous magnesium sulfate and evaporated at reduced pressure to a yellow oil, the crude ethylborate ester. 400 ml. of anhydrous methanol is added, and the reaction mixture is stirred at room temperature for 2.5 hours. The methanol is evaporated at reduced pressure and 40° C., and the residue is dissolved in 4:1 (by volume) chloroform/ethyl acetate and chromatographed on a silica gel column (3" diameter×8" height) using the same solvent as the eluant. The fractions containing the relatively pure product are combined and evaporated at reduced pressure to obtain the product as an oil (6.7 g. (61% overall yield from Steps 5 and 6)).

(b) An impure chromatography fraction (containing some product) is evaporated at reduced pressure, and the residue is triturated with diethyl ether and n-pentane and seeded with a crystal that formed upon addition of the methanol to the ethylborate ester to obtain the product as a white powder (0.7 g. (6%)), m.p. 122°-124° C.

The product is a racemate which may be resolved into two optically pure enantiomers, the 3R,5S and 3S,5R isomers, of which the former is preferred.

EXAMPLE 6

Erythro-(±)-(E)-3,5-dihydroxy-7-[3'-(4''-fluorophenyl)-1'-(1'''-methylethyl)indol-2'-yl]hept-6-enoic acid
(Reactions C and D)

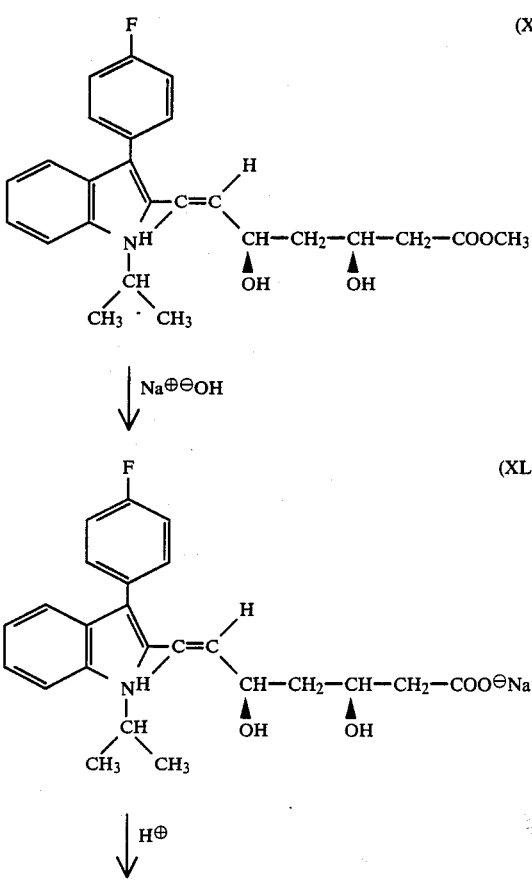

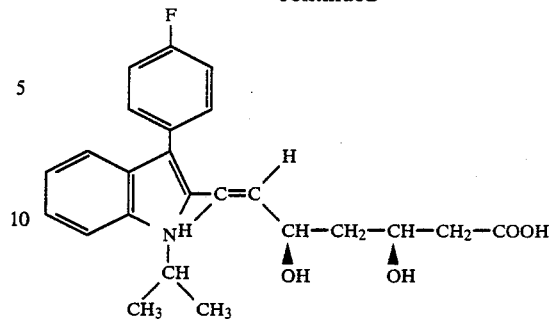

(a) 17.3 ml. of 1N. sodium hydroxide solution (17.3 mmol.) is added dropwise to a solution of 6.7 g. (15.7 mmol.) of Compound XLI (from Example 5) in 300 ml. of methanol, the reaction mixture is stirred at room temperature for 2 hours, and the methanol is evaporated at reduced pressure to obtain crude racemic Compound XLIX.

(b) 4.5 ml. of 1N. sodium hydroxide solution (4.5 mmol.) and 2.0 g. (4.7 mmol.) of Compound XLI (from Example 5) are stirred in 150 ml. of ethanol at room temperature for 2 hours, the solvent is evaporated at reduced pressure, and the residue is dissolved in 50 ml. of water. The aqueous solution is gently extracted with diethyl ether, the traces of ether in the aqueous layer are removed at reduced pressure, and the aqueous layer is freeze dried to obtain racemic Compound XLIX (1.8 g. (88%)), m.p. 194°–197° C.

(c) The crude Compound XLIX from Part (a) is dissolved in water, and the solution is acidified to pH 2 with 2N. hydrochloric acid and extracted with diethyl ether. The diethyl ether extract is washed three times with saturated sodium chloride solution, dried over anhydrous magnesium sulfate and evaporated at reduced pressure to obtain the crude solid racemic product (6.9 g.).

Compounds XLIX and L may both be resolved into two optically pure enantiomers, the 3 R,5S and 3S,5R isomers, of which the former is preferred.

EXAMPLES 7(a) and 7(b)

(E)-(±)-Trans-4-hydroxy-6-[2'-[3''-(4'''-fluorophenyl)-1''-(1'''-methylethyl)indol-2''-yl]ethenyl]-3,4,5,6-tetrahydro-2H-pyran-2-one and the corresponding cis lactone
(Reaction E)

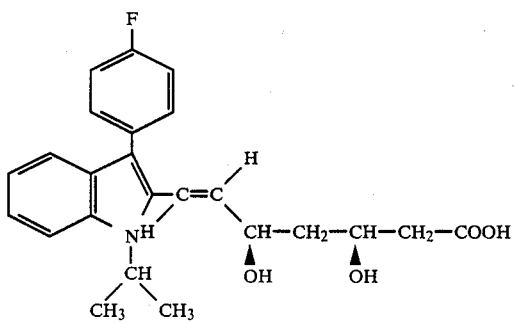

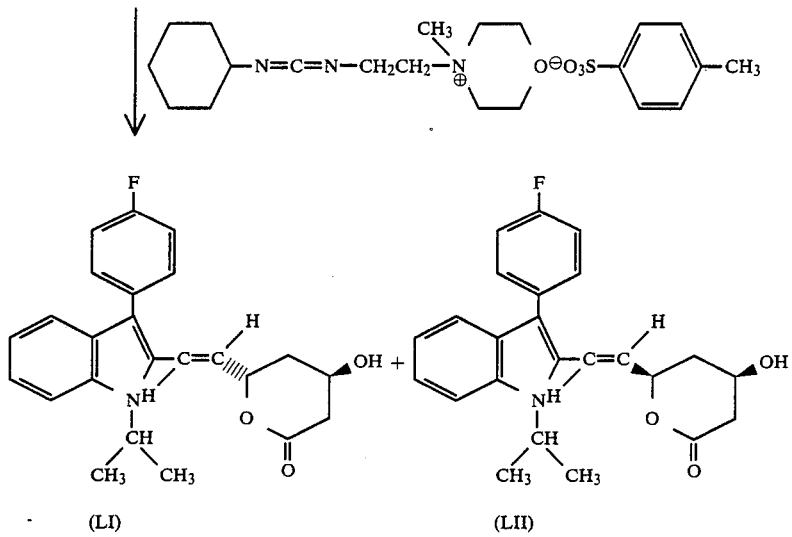

(a) 6.9 g. (15.7 mmol. assuming 100% yield) of crude Compound L (from Part (c) of Example 6) and 7 g. (16.5 mmol.) of N-cyclohexyl-N'-[2-(N''-methylmorpholinium)ethyl]carbodiimide p-toluenesulfonate are stirred in 300 ml. of methylene chloride at room temperature for 3 hours. The reaction mixture is extracted with water, dried over anhydrous magnesium sulfate and evaporated at reduced pressure. The residual oil is chromatographed on a silica gel column (3" diameter × 6" height) utilizing 7:2:1 (by volume) methyl-t-butyl ether/n-hexane/acetone as the eluant. The initial fractions, containing the racemic trans lactone, are combined and evaporated at reduced pressure to obtain the product as a foam (2.6 g.).

N.M.R. (CDCl$_3$): 1.68, (6H doublet) 1.75-2.05, (3H multiplet); 2.55-2.82, (2H multiplet); 4.38, (1H multiplet); 4.82, (1H quintet); 5.25, (1H multiplet); 5.72, (1H quartet); 6.75, (1H doublet); 7.05-7.6, (8H multiplet).

I.R. (CHCl$_3$): 3600 (m), 3480 (broad), 2980 (m), 2930 (m), 1720 (s) and 1225 (s) cm.$^{-1}$ and others.

The product is a racemate that may be resolved by, for example, the process set forth above into two optically pure enantiomers, the 4R,6S and 4S,6R isomers, of which the former is preferred.

(b) The chromatography fractions from Part (a) of this example containing the cis lactone are combined and evaporated at reduced pressure to obtain the solid product (0.22 g.), m.p. 170°-175° C. (dec.).

N.M.R. (CDCl$_3$): 1.58, (1H multiplet); 1.68, (6H doublet); 2.05, (1H doublet); 2.22 (1H multiplet); 2.52, (1H quartet); 2.95, (1H quartet); 4.3, (1H multiplet); 4.8, (2H multiplet); 5.72, (1H quartet); 6.78, (1H doublet); 7.1-7.6 (8H multiplet).

I.R. (CHCl$_3$): 3600 (m), 3480 (broad), 2980 (m), 2930 (m), 1720 (s) and 1225 (s) cm.$^{-1}$ and others.

The product is a racemate that may be separated into two optically pure enantiomers, the 4R,6R and 4S,6S isomers of which the former is preferred. The cis lactone results from a small amount of the threo isomer of Compound XLI formed in Step 6 of Example 5 and not separated therefrom which is carried through Reactions C and D (Parts (a) and (c) of Example 6) and Reaction E (Part (a) of this example).

EXAMPLE 8

Sodium erythro-($\pm$)-(E)-3,5-dihydroxy-7-[3'-(4''-fluorophenyl)-1'-(1''-methylethyl)indol-2'-yl]hept-6-enoate
(Reaction EE)

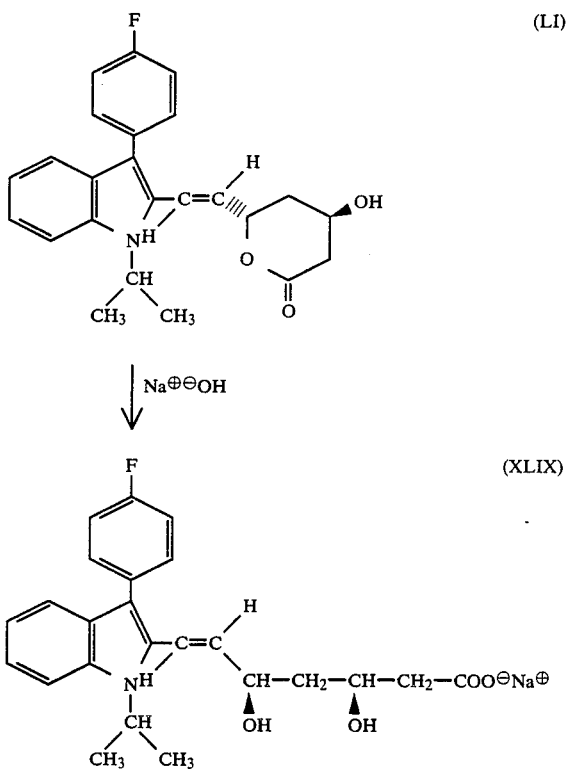

2.6 g. (6.6 mmol.) of Compound LI (from Part (a) of Example 7), 12.6 ml. of 0.5N. sodium hydroxide solution (6.3 mmol.) and 200 ml. of absolute ethanol are stirred for 2 hours at room temperature, the solvent is evaporated at reduced pressure, and the residue is dissolved in 150 ml. of water. The aqueous solution is gently washed with diethyl ether and freeze dried to obtain the solid racemic product (2.7 g.).

N.M.R. (CDCl$_3$+CD$_3$OD): 1.55, (1H multiplet); 1.6, (6H doublet); 2.2–2.45, (3H multiplet); 4.08, (1H multiplet); 4.42, (1H multiplet); 4.9, (1H quintet); 5.75, (1H doublet of a doublet); 6.68, (1H doublet); 7–7.2, (4H multiplet); 7.48–7.58, (4H multiplet).

I.R. (KBr): 3413 (broad s), 2978 (m), 2936 (m), 2936 (m), 1572 (s) and 1216 (s) cm.$^{-1}$ and others.

The racemic product may be resolved into two optically pure enantiomers, the 3R,5S and 3S,5R isomers, of which the former is preferred. See Example 14.

EXAMPLE 9

Sodium threo-(±)-(E)-3,5-dihydroxy-7-[3'-(4''-fluorophenyl)-1'-(1'''-methylethyl)indol-2'-yl]hept-6-enoate (Reaction EE)

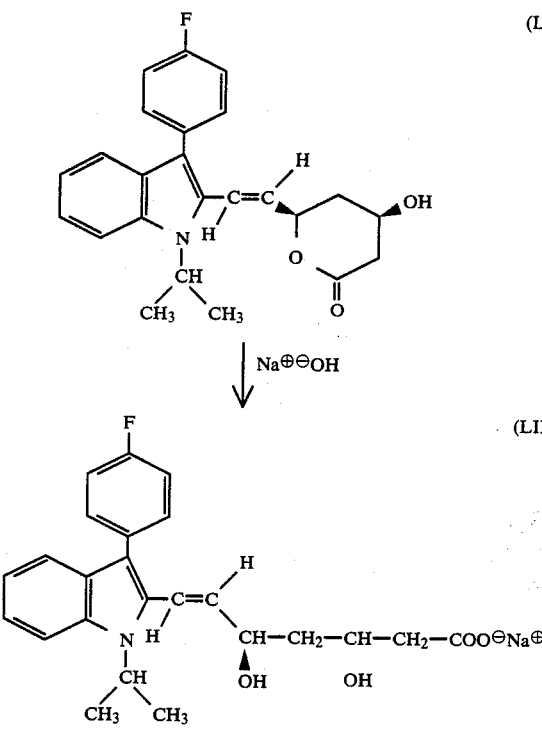

0.24 ml. of 1N. sodium hydroxide solution (0.24 mmol.) is added to a suspension of 100 mg. (0.25 mmol.) of Compound LII in 10 ml. of ethanol, the resulting solution is stirred for 1 hour at room temperature, and the solvent is evaporated at reduced pressure. The residue is dissolved in chloroform, and the solution is triturated with diethyl ether to obtain the solid product (83 mg. (73%)).

N.M.R. (D$_2$O): 1.05, (6H doublet); 1.28, (2H multiplet); 2.18, (2H doublet); 3.95, (1H multiplet); 4.2, (1H multiplet); 4.5, (1H multiplet); 5.4, (1H doublet of a doublet); 6.4, (1H doublet); 6.5–7.2 (8H multiplet).

The racemic threo compound may be resolved by conventional means into its 3R,5R and 3S,5S components.

EXAMPLE 10

(E)-Trans-6S-[2'-[3''-(4'''-fluorophenyl)-1''-methylindol-2''-yl]ethenyl]-4R-hydroxy-3,4,5,6-tetrahydro-2H-pyran-2-one

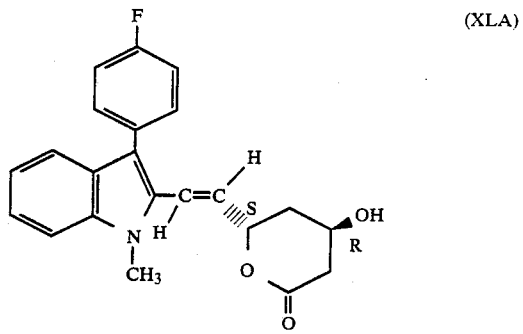

Step 1 (Reaction R)
3-(4'-Fluorophenyl)-1-methylindole-2-carboxaldehyde

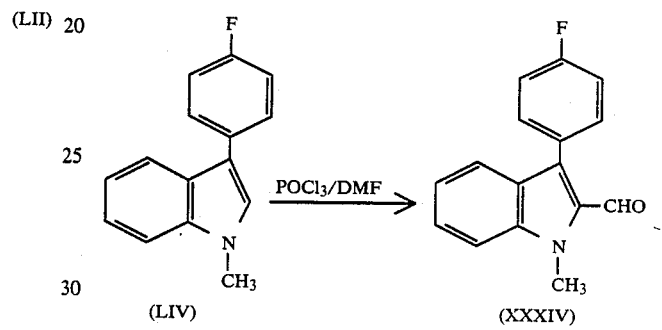

78.5 ml. (0.84 mole) of phosphorus oxychloride is added dropwise over a 20 min. period to 213 ml. of dimethylformamide stirred at 0° C. under nitrogen, the temperature of the reaction mixture not being allowed to exceed 10° C. The reaction mixture is heated to 80° C., a solution of 163.5 g. (0.727 mole) of 3-(4'-fluorophenyl)-1-methylindole in 270 ml. of dimethylformamide is added at a rate such that the temperature of the reaction mixture is maintained at 81°–83° C., the reaction mixture is maintained at 80°–81° C. for 5 hours and cooled to 10° C., and 1 l. of 15% sodium hydroxide solution is added dropwise at a rate such that the temperature of the reaction mixture is maintained at 35°–40° C., the reaction mixture being stirred under nitrogen throughout. The reaction mixture is cooled to 25° C., and the solids are collected by filtration, washed three times with 500 ml. portions of water and dissolved in 500 ml. of methylene chloride. The methylene chloride solution is filtered through 500 ml. of silica gel (70–230 mesh A.S.T.M.) and the silica gel is carefully washed with 2 l. of methylene chloride. The methylene chloride solutions are combined and concentrated to a volume of 300 ml. at reduced pressure, 300 ml. of absolute ethanol is added, and the reaction mixture is distilled until the internal temperature reaches 78° C. The reaction mixture is cooled to 0° C. and the precipitated bright yellow product is collected by filtration and vacuum dried at room temperature (153.9 g. (84%)), m.p. 80.5°–81.5° C. A slightly less pure second crop may be obtained from the mother liquor.

Step 2 (Reaction S)
3-(4'-Fluorophenyl)-2-hydroxymethyl-1-methylindole

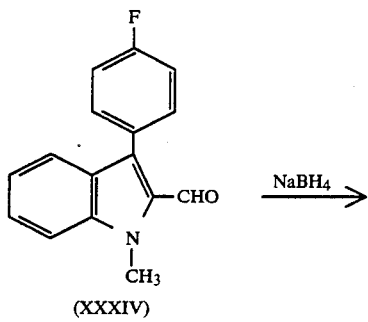

(XXXIV)

NaBH₄ →

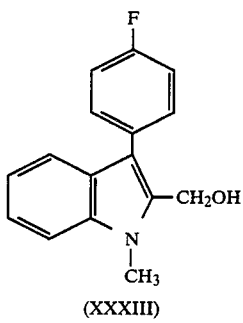

(XXXIII)

A solution of 160 g. (0.6324 mole) of Compound XXXIV in 650 ml. of tetrahydrofuran is added over a 20 min. period to a mixture of 9.6 g. (0.25 mole) of sodium borohydride, 650 ml. of tetrahydrofuran and 65 ml. of methanol stirred at 0° C. under nitrogen, the temperature of the reaction mixture not being allowed to exceed 14° C. The reaction mixture is stirred under nitrogen at 5°–10° C. for 30 min., and the tetrahydrofuran and methanol are distilled at atmospheric pressure. 1 l. of toluene is added to the oily residue (200–300 ml.) and the residual tetrahydrofuran is distilled at atmospheric pressure until the temperature reaches 108°–110° C. The toluene solution is cooled to 40° C., 1.3 l. of 0.5N. sodium hydroxide is rapidly added, and the two phases are mixed and separated. The organic phase is heated to 50°–55° C., 1.1 l. of n-hexane is added, the solution is cooled to 5° C., and the precipitated colorless product is collected by filtration and vacuum dried for 16 hours at room temperature (136 g. (84.3%)), m.p. 110°–111° C. A less pure second crop (20 g.) may also be obtained.

Step 3 (Reaction T)

2-Chloromethyl-3-(4'-fluorophenyl)-1-methylindole

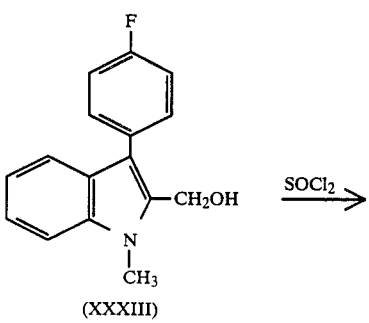

(XXXIII)

SOCl₂ →

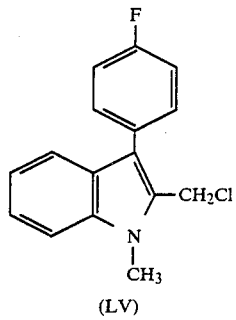

(LV)

29.5 ml. (0.404 mole) of thionyl chloride is added over a 10 min. period to a solution of 63.8 g. (0.25 mole) of Compound XXXIII in 650 ml. of dry tetrahydrofuran (dried over molecular sieves) stirred at −7° C. under nitrogen. The reaction mixture is stirred at −5°–0° C. under nitrogen for 2.5 hours, 350 ml. of toluene is added (with cooling to keep the temperature of the reaction mixture at or below 5° C.), tetrahydrofuran and excess thionyl chloride are distilled at 0.5–2 mm. Hg. and 0°–10° C. until the volume of the reaction mixture is about 400 ml., an additional 350 ml. of toluene is added and another 100 ml. of solvent is distilled at 0.5–1 mm. Hg. and 10°–20° C. to obtain a solution of the product in toluene.

Step 4 (Reaction V)

3-(4'-Fluorophenyl)-1-methyl-2-triphenylphosphoniummethylindole chloride

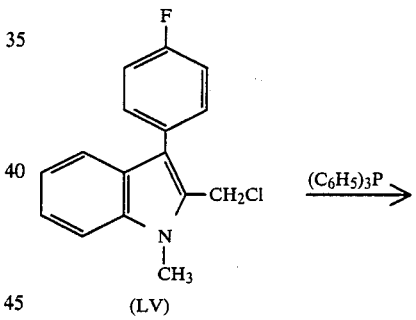

(LV)

(C₆H₅)₃P →

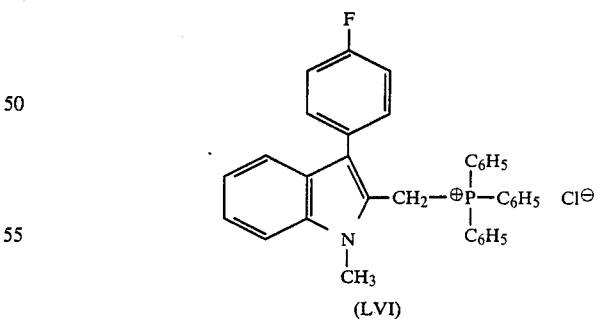

(LVI)

A solution of 66.2 g. (0.25 mole) of triphenylphosphine in 1 l. of toluene is added over a 3 min. period to the solution of Compound LV obtained in Step 3 stirred at 15°–20° C. under nitrogen, and the reaction mixture is stirred at 108°–110° C. under nitrogen for 5 hours and cooled to 25° C. The product is collected by filtration, washed twice with 50 ml. portions of toluene and once with 50 ml. of n-heptane and vacuum dried, 93 g. (70%), m.p. 270°–271° C. (dec.).

Step 5 (Reaction W)
(E)-4β R-(1',1'-dimethylethyl-diphenylsilyloxy)-6αS-[2'-[3''-(4'''-fluorophenyl)-1''-methylindol-2''-yl]ethenyl]-2β-methoxy-3,4,5,6-tetrahydro-2H-pyran and the corresponding (Z) compound

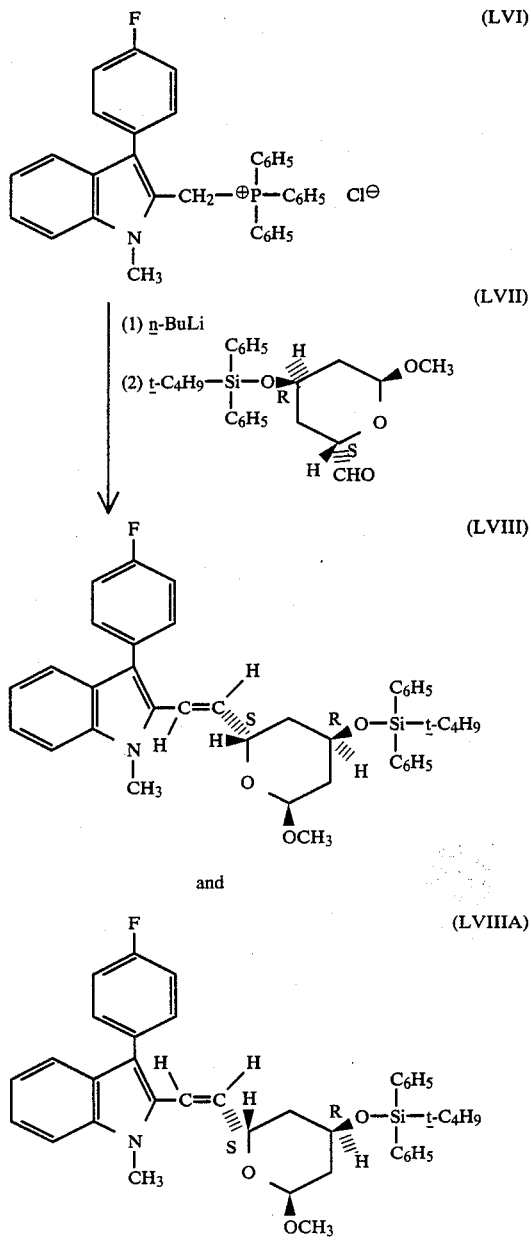

6.0 ml. of 1.3M. n-butyllithium/n-hexane (7.8 mmol.) is added dropwise over a 7 min. period to a slurry of 4.0 g. (7.47 mmol.) of Compound LVI (stripped from toluene at reduced pressure and dried under high vacuum prior to use) in 100 ml. of dry tetrahydrofuran (freshly distilled from sodium and benzophenone) stirred at room temperature under nitrogen. The reaction mixture is cooled to 0° C., and 2.98 g. (7.48 mmol.) of Compound LVII (stripped from toluene at reduced pressure and dried under high vacuum prior to use) in 20 ml. of dry tetrahydrofuran is added dropwise over a 5 min. period, an additional 10 ml. of dry tetrahydrofuran is added, and the reaction mixture is maintained at about 0° C. for 45 min., allowed to warm to room temperature and maintained at room temperature for 17 hours, the reaction mixture being stirred under nitrogen throughout. The reaction mixture is poured into 500 ml. of water and extracted four times with 250 ml. portions of diethyl ether. The diethyl ether extracts are combined and dried over anhydrous magnesium sulfate and then over anhydrous sodium sulfate and evaporated at reduced pressure. The last traces of diethyl ether are removed under high vacuum to obtain a semi-solid residue. The residue is subjected to medium pressure liquid chromatography utilizing a silica gel column and methylene chloride as the eluant, with those fractions containing one product and one or more contaminants or a mixture of the products (with or without one or more contaminants) as determined by thin layer chromatography being recycled, to obtain 1.83 g. (39.6%) of the (E) (i.e., trans) olefin (Compound LVIII) as an orange foam and 0.671 g. (14.5%) of the (Z) (i.e., cis) olefin (Compound LVIIIA) also as an orange foam.

Step 6 (Reaction X)
(E)-4β R-(1'1'-dimethylethyl-diphenylsilyloxy)-6αS-[2'-[3''-(4'''-fluorophenyl)-1''-methylindol-2''-yl]ethenyl]-2-hydroxy-3,4,5,6-tetrahydro-2H-pyran and the corresponding 6β R compound

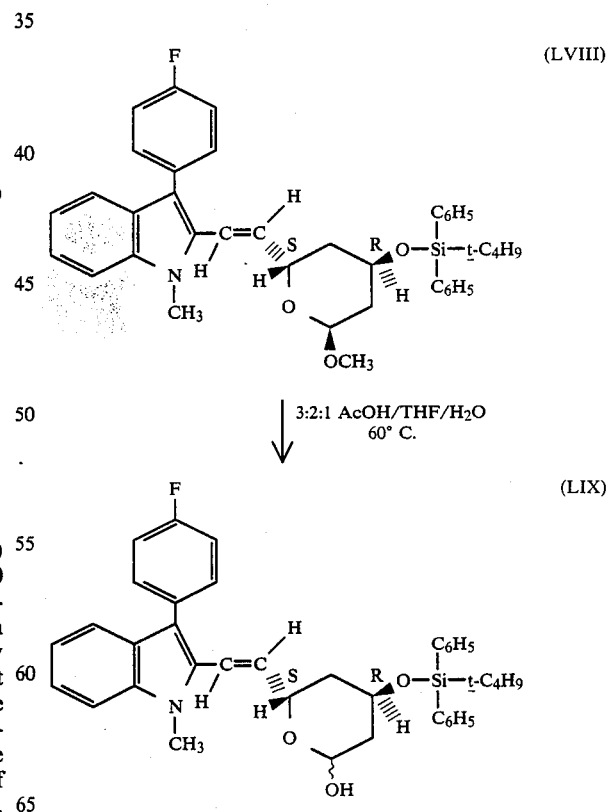

and

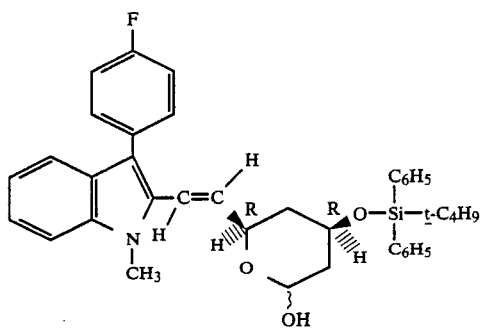 (LX)

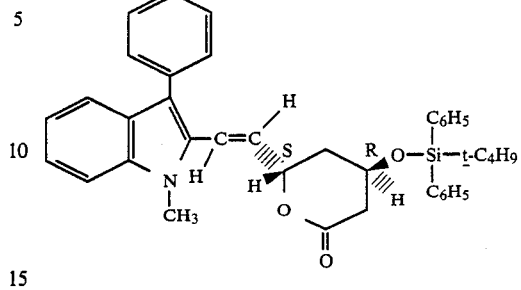 (LXI)

1.18 g. (1.9 mmol.) of Compound LVIII is dissolved in 56 ml. of glacial acetic acid, 37.2 ml. of tetrahydrofuran is added, and 18.6 ml. of distilled water is slowly added, the reaction mixture being stirred at room temperature throughout. The reaction mixture is stirred at 60° C. for 18.5 hours and allowed to cool. The tetrahydrofuran is evaporated at reduced pressure, and the reaction mixture is poured into 500 ml. of distilled water and extracted four times with 300 ml. portions of diethyl ether. The diethyl ether extracts are combined, washed with saturated sodium bicarbonate solution (until no gas is evolved upon shaking), dried over anhydrous magnesium sulfate and then over anhydrous sodium sulfate and evaporated to dryness at reduced pressure. The last traces of solvent are removed under high vacuum to obtain a yellow foam. Flash chromatography of the foam utilizing 250 g. of silica gel and 1:1 (by volume) diethyl ether/n-hexane as the eluant yielded 329.9 mg. (28.6%) of Compound LIX and 366.7 mg. (31.7%) of Compound LX.

Step 7 (Reaction Y)

(E)-4βR-(1',1'-dimethylethyl-diphenylsilyloxy)-6αS-[2'-[3''-(4'''-fluorophenyl)-1''-methylindol-2''-yl]ethenyl]-3,4,5,6-tetrahydro-2H-pyran-2-one A solution of 236.8 mg. (0.391 mmol.) of Compound LIX in 8 ml. of acetone (passed through a column of Activity I alumina immediately prior to use) is added to 137.5 mg. (1.174 mmol.) of N-methylmorpholine N-oxide (obtained by heating N-methylmorpholine N-oxide hydrate at 90° C. for 2–3 hours under high vacuum), the reaction mixture is stirred at room temperature under nitrogen until the solid dissolves, 23.5 mg. (0.025 mmol.) of dichlorotris(triphenylphosphine)ruthenium (II) is added, and the reaction mixture is stirred under nitrogen for 55 min. 10 ml. of diethyl ether is added, and the resulting solid is washed several times with diethyl ether. The diethyl ether washings are combined, the diethyl ether is evaporated at reduced pressure to near dryness, and the residue is dissolved in 100 ml. of diethyl ether. The diethyl ether solution is washed twice with 100 ml. portions of ice-cold 2.5% hydrochloric acid, twice with 100 ml. portions of saturated sodium bicarbonate solution and once with 100 ml. of saturated sodium chloride solution, dried over anhydrous sodium sulfate and evaporated to dryness at reduced pressure to obtain the crude product as a yellow oil (243.4 mg.).

Step 8 (Reaction Z)

(E)-Trans-6S-[2'-[3''-(4'''-fluorophenyl)-1''-methylindol-2''-yl]ethenyl]-4R-hydroxy-3,4,5,6-tetrahydro-2H-pyran-2-one

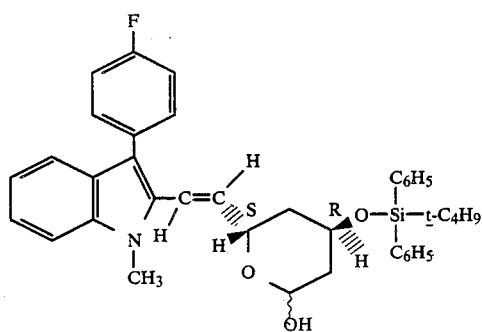 (LIX)

N—methylmorpholine-N—oxide + RuCl$_2$(P(C$_6$H$_5$)$_3$)$_3$/CH$_3$COCH$_3$

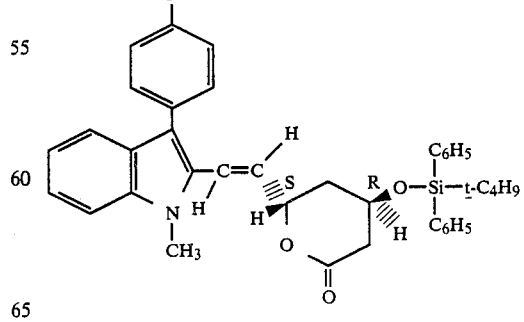 (LXI)

(n-C$_4$H$_9$)$_4$N$^{\oplus}$F$^{\ominus}$/AcOH + THF

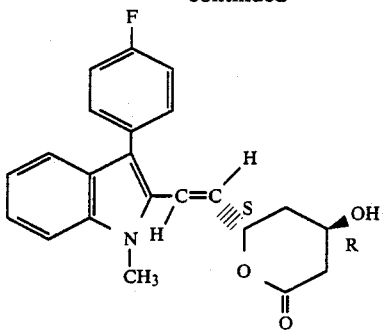

(XLA)

113 μl. of glacial acetic acid is added dropwise to a solution of 237.5 mg. (0.391 mmol.) of crude Compound LXI (from Step 7) in 18 ml. of dry tetrahydrofuran stirred at room temperature under nitrogen followed by the dropwise addition of 1.564 ml. of 1M. tetra-n-butylammonium fluoride/tetrahydrofuran. The reaction mixture is stirred at room temperature under nitrogen for 2 hours, poured into 200 ml. of ice-cold water and extracted four times with 75 ml. portions of diethyl ether. The organic phases are combined, washed once with 300 ml. of saturated sodium bicarbonate solution and once with 300 ml. of saturated sodium chloride solution and dried over anhydrous sodium sulfate. The solvent is evaporated at reduced pressure, with the last traces being evaporated under high vacuum to obtain a yellow oil which is triturated with diethyl ether to obtain the product as a pale yellow solid. Additional product is obtained from the mother liquor by repeating this procedure three times. A total of 83.5 mg. (58.5%), m.p. 139°–140° C., is obtained.

N.M.R. (CDCl$_3$): 1.7–2.1, (3H multiplet); 2.71, (2H multiplet); 3.87, (3H singlet); 4.42, (1H multiplet); 5.31, (1H multiplet); 5.93, (1H doublet of a doublet; $J_1=16$ Hz., $J_2=6$ Hz); 6.79, (1H doublet; $J=16$ Hz.); 7.1–7.6, (8H multiplet).

I.R. (CHCl$_3$): 3612, 3466, 3039, 3002, 2933, 1736, 1543, 1369 and 1256 cm.$^{-1}$ and others.

A second batch, obtained by resolution of the racemate by the procedure described above, had an $[\alpha]_D^{25} = -18.5°$ (CHCl$_3$, c=0.2 g.) See Example 4(a).

EXAMPLE 11

(E)-Cis-6R-[2'-[3''-(4'''-fluorophenyl)-1''-methylindol-2''-yl]ethenyl]-4R-hydroxy-3,4,5,6-tetrahydro-2H-pyran-2-one

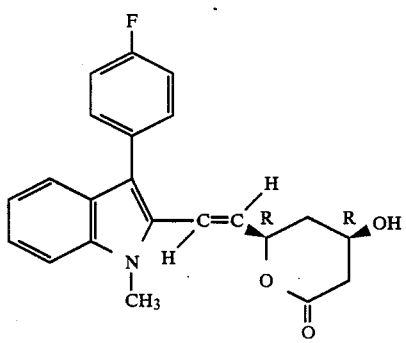

(LXII)

The product is obtained as an oil from Compound LX (Step 6 of Example 10) by the processes of Steps 7 and 8 of Example 10 and is purified by chromatography on silica gel utilizing 1:1 (by volume) ethyl acetate/methylene chloride as the eluant.

N.M.R. (CDCl$_3$): 1.71, (1H multiplet); 2.05, (1H multiplet); 2.31, (1H multiplet); 2.52, (1H doublet of a doublet, $J_1=17.5$ Hz., $J_2=8$ Hz.); 2.95, (1H doublet of a doublet), $J_1=17.5$ Hz., $J_2=5.5$ Hz.; 3.85, (3H singlet); 4.31, (1H multiplet); 4.81, (1H multiplet); 5.97, (1H doublet of a doublet, $J_1=16$ Hz., $J_2=6$ Hz.); 6.77, (1H doublet, $J=16$ Hz); 7.09–7.72 (8H multiplet).

I.R. (CH$_2$Cl$_2$): 3601, 3034, 3026, 2962, 1742, 1366 and 1230 cm.$^{-1}$ and others.

EXAMPLE 12

(Z)-Trans-6S-[2'-[3''-(4'''-fluorophenyl)-1''-methylindol-2''-yl]ethenyl]-4R-hydroxy-3,4,5,6-tetrahydro-2H-pyran-2-one

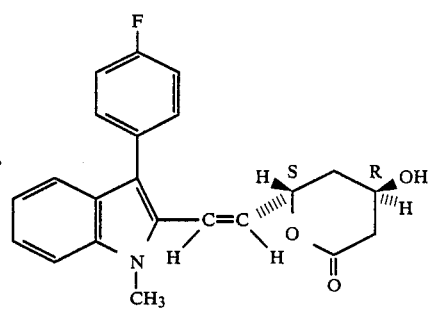

(LXIII)

The product is obtained as an oil from Compound LVIIIA (Step 5 of Example 10) by the processes of Steps 6–8 of Example 10. $[\alpha]_D^{25} = +136.935°$ (CH$_2$Cl$_2$, c=1.24 g.)

N.M.R. (CDCl$_3$): 0.75, (1H multiplet); 1.14, (1H multiplet); 1.49, (1H multiplet); 2.48, (2H multiplet); 3.76, (3H singlet); 4.1, (1H broad singlet); 5.1, (1H multiplet); 5.89, (1H doublet of a doublet, $J_1=10.5$ Hz. $J_2=10$ Hz.); 6.7, (1H doublet, $J=1.5$ Hz.); 7.09–7.73, (8H multiplet).

I.R. (CH$_2$Cl$_2$): 3604, 3084, 3026, 2930, 1739, 1364 and 1224 cm.$^{-1}$ and others.

EXAMPLE 13

(E)-Trans-6S-[2'-[3''-(4'''-fluorophenyl)-1''-(1'''-methylethyl)indol-2''-yl]ethenyl]-4R-hydroxy-3,4,5,6-tetrahydro-2H-pyran-2-one

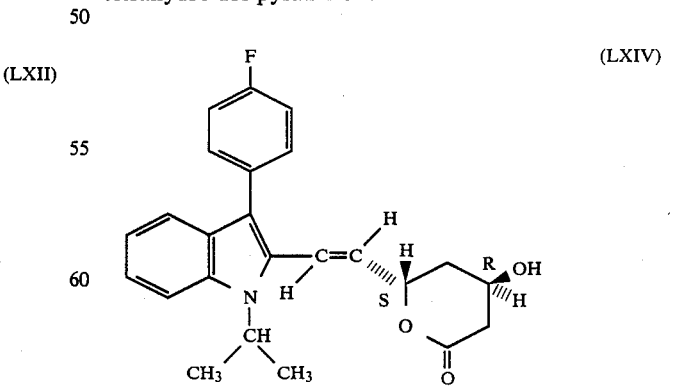

(LXIV)

The product may be obtained from Compounds XLIV and LVII by the processes of Steps 1–8 of Example 10. $[\alpha]_D^{25} = -15.84°$ (CHCl$_3$, c=1.3 g.)

EXAMPLE 14

Sodium erythro-(E)-3R,5S-dihydroxy-7-[3'-(4"-fluorophenyl)-1'-(1"-methylethyl)indol-2'-yl]hept-6-enoate

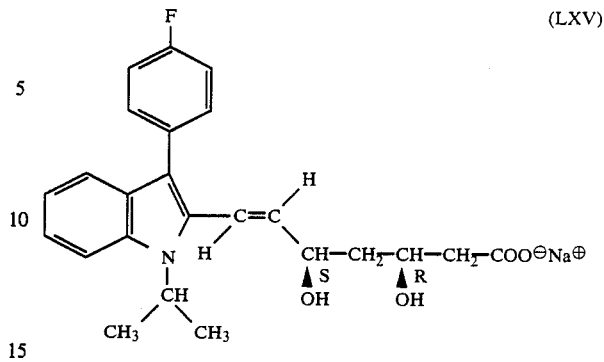
(LXV)

The product may be obtained from Compound LXIV by the process of Example 8 or Example 9.
$[\alpha]_D^{25} = -13.33°$ (CHCl$_3$, c=0.99 g.)

TABLE I

Examples 15-82
The following compounds of Group IAa may be synthesized by the processes set forth above:

| | R$_1$ | R$_2$ | R$_3$ | R$_4$ | R$_5$ | R$_{5a}$ | X | R$_6$ | R$_7$ | m.p. | Isomer(s) |
|---|---|---|---|---|---|---|---|---|---|---|---|
| Ex. 15 | CH$_3$ | H | H | H | H | H | \C=C/ (H,H) | H | CH$_3$ | | D |
| Ex. 16 | CH$_3$ | H | H | H | H | H | \C=C/ (H,H) | H | C$_2$H$_5$ | Viscous oil | D |
| Ex. 17 | CH$_3$ | H | H | H | H | H | \C=C/ (H,H) | H | Na | | D |
| Ex. 18 | CH$_3$ | H | H | H | H | H | \C=C/ (H,H) | H | H | | D |
| Ex. 19 | CH$_3$ | H | H | H | H | H | \C=C/ (H,H) | H | Na | Amorphous solid | E |
| Ex. 20 | CH$_3$ | H | H | H | H | H | \C=C/ (H,H) | H | Na | Amorphous solid | T |
| Ex. 21 | CH$_3$ | 6-OCH$_2$C$_6$H$_5$ | H | 4-F | H | H | \C=C/ (H,H) | H | C$_2$H$_5$ | Solid foam | D |
| Ex. 22 | CH$_3$ | 6-OCH$_2$C$_6$H$_5$ | H | 4-F | H | H | \C=C/ (H,H) | H | K | | D |
| Ex. 23 | CH$_3$ | 6-OCH$_2$C$_6$H$_5$ | H | 4-F | H | H | \C=C/ (H,H) | H | Na | Amorphous solid | D |
| Ex. 24 | CH$_3$ | 6-OCH$_2$C$_6$H$_5$ | H | 4-F | H | H | \C=C/ (H,H) | H | H | | D |

TABLE I-continued

Examples 15–82
The following compounds of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 25 | CH₃ | H | H | 4-F | H | H | DB | H | CH₃ | | D |
| Ex. 26 | CH₃ | H | H | 4-F | H | H | DB | H | Na | | D |
| Ex. 27 | CH₃ | H | H | 4-F | H | H | DB | H | H | | D |
| Ex. 28 | CH₃ | H | H | 3-CH₃ | 4-CH₃ | H | \C=C/ (H,H / H) | H | C₂H₅ | Oil | D |
| Ex. 29 | CH₃ | H | H | 3-CH₃ | 4-CH₃ | H | \C=C/ | H | K | | D |
| Ex. 30 | CH₃ | H | H | 3-CH₃ | 4-CH₃ | H | \C=C/ | H | H | | D |
| Ex. 31 | i-C₃H₇ | H | H | 4-F | H | H | \C=C/ | H | C₂H₅ | | D |
| Ex. 32 | i-C₃H₇ | H | H | 4-F | H | H | \C=C/ | H | CH₃ | Viscous oil | D |
| Ex. 33 | i-C₃H₇ | H | H | 4-F | H | H | \C=C/ | H | K | | D |
| Ex. 34 | i-C₃H₇ | H | H | 4-F | H | H | \C=C/ | H | H | | D |
| Ex. 35 | CH₃ | 4-OCH₂C₆H₅ | H | 4-F | H | H | \C=C/ | H | C₂H₅ | Viscous oil | D |
| Ex. 36 | CH₃ | 4-OCH₂C₆H₅ | H | 4-F | H | H | \C=C/ | H | K | | D |
| Ex. 37 | CH₃ | 4-OCH₂C₆H₅ | H | 4-F | H | H | \C=C/ | H | H | | D |
| Ex. 38 | CH₃ | H | H | 3-CH₃ | 5-CH₃ | H | \C=C/ | H | C₂H₅ | Viscous oil | D |
| Ex. 39 | CH₃ | H | H | 3-CH₃ | 5-CH₃ | H | \C=C/ | H | K | | D |
| Ex. 40 | CH₃ | H | H | 3-CH₃ | 5-CH₃ | H | \C=C/ | H | H | | D |

TABLE I-continued

Examples 15-82
The following compounds of Group IAa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 41 | $CH_3$ | H | H | 3-$CH_3$ | 5-$CH_3$ | H | -CH=CH- | H | Na | Amorphous solid | E |
| Ex. 42 | $CH_3$ | H | H | 3-$CH_3$ | 5-$CH_3$ | H | -CH=CH- | H | Na | Amorphous solid | T |
| Ex. 43 | $CH_3$ | 5-Cl | H | 4-F | H | H | -CH=CH- | H | $C_2H_5$ | 96°–105° C. | D |
| Ex. 44 | $CH_3$ | 5-Cl | H | 4-F | H | H | -CH=CH- | H | K | | D |
| Ex. 45 | $CH_3$ | 5-Cl | H | 4-F | H | H | -CH=CH- | H | H | | D |
| Ex. 46 | $CH_3$ | 5-$OCH_3$ | H | 4-F | H | H | -CH=CH- | H | $C_2H_5$ | Viscous oil | D |
| Ex. 47 | $CH_3$ | 5-$OCH_3$ | H | 4-F | H | H | -CH=CH- | H | Na | | D |
| Ex. 48 | $CH_3$ | 5-$OCH_3$ | H | 4-F | H | H | -CH=CH- | H | H | | D |
| Ex. 49 | $CH_3$ | H | H | 4-F | H | H | -CH=CH- | H | Na | 193°–196° C. (dec.) | E |
| Ex. 50 | $CH_3$ | 7-$OCH_2C_6H_5$ | H | 4-F | H | H | -CH=CH- | H | $C_2H_5$ | 78°–82° C. | D |
| Ex. 51 | $CH_3$ | 7-$OCH_2C_6H_5$ | H | 4-F | H | H | -CH=CH- | H | Na | | D |
| Ex. 52 | $CH_3$ | 7-$OCH_2C_6H_5$ | H | 4-F | H | H | -CH=CH- | H | H | | D |
| Ex. 53 | $CH_3$ | 7-$OCH_2C_6H_5$ | H | 4-F | H | H | -CH=CH- | H | Na | Amorphous solid | E |
| Ex. 54 | $CH_3$ | 7-$OCH_2C_6H_5$ | H | 4-F | H | H | -CH=CH- | H | Na | Amorphous solid | T |

TABLE I-continued

Examples 15-82
The following compounds of Group IAa may be synthesized by the processes set forth above:

| | R$_1$ | R$_2$ | R$_3$ | R$_4$ | R$_5$ | R$_{5a}$ | X | R$_6$ | R$_7$ | m.p. | Isomer(s) |
|---|---|---|---|---|---|---|---|---|---|---|---|
| Ex. 55 | CH$_3$ | 5-OCH$_2$C$_6$H$_5$ | H | 4-F | H | H | \C=C/ (H,H / H,H) | H | C$_2$H$_5$ | Viscous oil | D |
| Ex. 56 | CH$_3$ | 5-OCH$_2$C$_6$H$_5$ | H | 4-F | H | H | \C=C/ | H | Na | | D |
| Ex. 57 | CH$_3$ | 5-OCH$_2$C$_6$H$_5$ | H | 4-F | H | H | \C=C/ | H | H | | D |
| Ex. 58 | C$_6$H$_5$—CH$_2$CH$_2$— | H | H | 4-F | H | H | \C=C/ | H | CH$_3$ | Oil | D |
| Ex. 59 | C$_6$H$_5$—CH$_2$CH$_2$— | H | H | 4-F | H | H | \C=C/ | H | Na | Amorphous solid | E |
| Ex. 60 | C$_2$H$_5$ | H | H | 4-F | H | H | \C=C/ | H | C$_2$H$_5$ | Viscous oil | D |
| Ex. 61 | C$_2$H$_5$ | H | H | 4-F | H | H | \C=C/ | H | Na | Amorphous solid | E |
| Ex. 62 | C$_2$H$_5$ | H | H | 4-F | H | H | \C=C/ | H | Na | Amorphous solid | T |
| Ex. 63 | i-C$_3$H$_7$ | 4-CH$_3$ | 6-CH$_3$ | 4-F | H | H | \C=C/ | H | C$_2$H$_5$ | 107°–110° C. | D |
| Ex. 64 | i-C$_3$H$_7$ | 4-CH$_3$ | 6-CH$_3$ | 4-F | H | H | \C=C/ | H | Na | Solid foam | E |
| Ex. 65 | i-C$_3$H$_7$ | 4-CH$_3$ | 6-CH$_3$ | 4-F | H | H | \C=C/ | H | H | | E |
| Ex. 66 | i-C$_3$H$_7$ | 4-CH$_3$ | 6-CH$_3$ | 4-F | H | H | \C=C/ | H | Na | Solid foam | T |
| Ex. 67 | i-C$_3$H$_7$ | H | H | 3-CH$_3$ | 5-CH$_3$ | H | \C=C/ | H | CH$_3$ | Viscous oil | D |
| Ex. 68 | i-C$_3$H$_7$ | H | H | 3-CH$_3$ | 5-CH$_3$ | H | \C=C/ | H | Na | 183°–186° C. | E |

4,739,073

TABLE I-continued

Examples 15-82
The following compounds of Group IAa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 69 | i-$C_3H_7$ | 5-cyclohexyl | H | 4-F | H | H |  | H | $CH_3$ | Viscous oil | D |
| Ex. 70 | i-$C_3H_7$ | 5-cyclohexyl | H | 4-F | H | H |  | H | Na | Solid foam | E |
| Ex. 71 | i-$C_3H_7$ | 5-cyclohexyl | H | 4-F | H | H |  | H | Na | Solid foam | T |
| Ex. 72 | cyclohexyl | H | H | 4-F | H | H |  | H | $CH_3$ | Solid foam | D |
| Ex. 73 | cyclohexyl | H | H | 4-F | H | H |  | H | Na | Amorphous solid | E |
| Ex. 74 | cyclohexyl | H | H | 4-F | H | H |  | H | Na | Amorphous solid | T |
| Ex. 75 | i-$C_3H_7$ | 6-$OCH_2C_6H_5$ | H | 4-F | H | H |  | H | $C_2H_5$ | Solid foam | D |
| Ex. 76 | i-$C_3H_7$ | H | H | 3-$CH_3$ | 4-F | 5-$CH_3$ |  | H | $C_2H_5$ | Viscous oil | D |
| Ex. 77 | i-$C_3H_7$ | H | H | 2-$CH_3$ | H | H |  | H | Na | Amorphous solid | E |
| Ex. 78 | i-$C_3H_7$ | H | H | 2-$CH_3$ | H | H |  | H | Na | Amorphous solid | T |
| Ex. 79 | i-$C_3H_7$ | H | H | 3-$CH_3$ | 4-F | H |  | H | Na | Amorphous solid | E |
| Ex. 80 | i-$C_3H_7$ | H | H | 3-$CH_3$ | 4-F | H |  | H | Na | Amorphous solid | T |
| Ex. 81 | i-$C_3H_7$ | H | H | 3-$CH_3$ | 4-F | 5-$CH_3$ |  | H | Na | Amorphous solid | E |
| Ex. 82 | i-$C_3H_7$ | 6-$OCH_2C_6H_5$ | H | 4-F | H | H |  | H | Na | 180°-182° C. (dec.) | E |

TABLE II

Examples 83-122A
The following compounds of Group IAb may be synthesized by the processes set forth above:

| | R₁ | R₂ | R₃ | R₄ | R₅ | R₅ₐ | X | R₆ | m.p. | Isomer(s) |
|---|---|---|---|---|---|---|---|---|---|---|
| Ex. 83 | $CH_3$ | H | H | H | H | H | $\begin{array}{c}\diagdown\phantom{C=C}/H\\C=C\\/\phantom{C=C}\diagdown\\H\end{array}$ | H | Solid foam | cis |
| Ex. 84 | $CH_3$ | H | H | H | H | H | $\begin{array}{c}\diagdown\phantom{C=C}/H\\C=C\\/\phantom{C=C}\diagdown\\H\end{array}$ | H | 119.5°–121° C. | trans |
| Ex. 85 | $CH_3$ | 6-$OCH_2C_6H_5$ | H | 4-F | H | H | $\begin{array}{c}\diagdown\phantom{C=C}/H\\C=C\\/\phantom{C=C}\diagdown\\H\end{array}$ | H | 145°–146° C. | mixture ~75% trans ~25% cis |
| Ex. 86 | $CH_3$ | 6-$OCH_2C_6H_5$ | H | 4-F | H | H | $\begin{array}{c}\diagdown\phantom{C=C}/H\\C=C\\/\phantom{C=C}\diagdown\\H\end{array}$ | H | | cis |
| Ex. 87 | $CH_3$ | 6-$OCH_2C_6H_5$ | H | 4-F | H | H | $\begin{array}{c}\diagdown\phantom{C=C}/H\\C=C\\/\phantom{C=C}\diagdown\\H\end{array}$ | H | | trans |
| Ex. 88 | $CH_3$ | H | H | 4-F | H | H | —$CH_2CH_2$— | H | | cis |
| Ex. 89 | $CH_3$ | H | H | 4-F | H | H | —$CH_2CH_2$— | H | 164°–169° C. (dec.) | trans |
| Ex. 90 | $CH_3$ | H | H | 3-$CH_3$ | 4-$CH_3$ | H | $\begin{array}{c}\diagdown\phantom{C=C}/H\\C=C\\/\phantom{C=C}\diagdown\\H\end{array}$ | H | Solid foam | cis |
| Ex. 91 | $CH_3$ | H | H | 3-$CH_3$ | 4-$CH_3$ | H | $\begin{array}{c}\diagdown\phantom{C=C}/H\\C=C\\/\phantom{C=C}\diagdown\\H\end{array}$ | H | Solid foam | trans |
| Ex. 92 | i-$C_3H_7$ | 4-$CH_3$ | 6-$CH_3$ | 4-F | H | H | $\begin{array}{c}\diagdown\phantom{C=C}/H\\C=C\\/\phantom{C=C}\diagdown\\H\end{array}$ | H | 150.5°–151° C. | ≧95% cis |
| Ex. 93 | i-$C_3H_7$ | 4-$CH_3$ | 6-$CH_3$ | 4-F | H | H | $\begin{array}{c}\diagdown\phantom{C=C}/H\\C=C\\/\phantom{C=C}\diagdown\\H\end{array}$ | H | 146°–147° C. | trans |
| Ex. 94 | $CH_3$ | 4-$OCH_2C_6H_5$ | H | 4-F | H | H | $\begin{array}{c}\diagdown\phantom{C=C}/H\\C=C\\/\phantom{C=C}\diagdown\\H\end{array}$ | H | | cis |
| Ex. 95 | $CH_3$ | 4-$OCH_2C_6H_5$ | H | 4-F | H | H | $\begin{array}{c}\diagdown\phantom{C=C}/H\\C=C\\/\phantom{C=C}\diagdown\\H\end{array}$ | H | | trans |
| Ex. 96 | $CH_3$ | H | H | 3-$CH_3$ | 5-$CH_3$ | H | $\begin{array}{c}\diagdown\phantom{C=C}/H\\C=C\\/\phantom{C=C}\diagdown\\H\end{array}$ | H | Solid foam | cis |
| Ex. 97 | $CH_3$ | H | H | 3-$CH_3$ | 5-$CH_3$ | H | $\begin{array}{c}\diagdown\phantom{C=C}/H\\C=C\\/\phantom{C=C}\diagdown\\H\end{array}$ | H | Solid foam | trans |

TABLE II-continued

Examples 83-122A
The following compounds of Group IAb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 98 | $CH_3$ | 5-Cl | H | 4-F | H | H | $\overset{H}{\underset{H}{>}}C=C\overset{H}{\underset{}{<}}$ | H | 165.5°-166° C. (dec.) | cis |
| Ex. 99 | $CH_3$ | 5-Cl | H | 4-F | H | H | $\overset{H}{\underset{H}{>}}C=C\overset{H}{\underset{}{<}}$ | H | 157.5°-159° C. | trans |
| Ex. 100 | $CH_3$ | 5-$OCH_3$ | H | 4-F | H | H | $\overset{H}{\underset{H}{>}}C=C\overset{H}{\underset{}{<}}$ | H | Solid foam | cis |
| Ex. 101 | $CH_3$ | 5-$OCH_3$ | H | 4-F | H | H | $\overset{H}{\underset{H}{>}}C=C\overset{H}{\underset{}{<}}$ | H | 102°-105° C. | trans |
| Ex. 102 | $CH_3$ | 7-$OCH_2C_6H_5$ | H | 4-F | H | H | $\overset{H}{\underset{H}{>}}C=C\overset{H}{\underset{}{<}}$ | H | 127°-128.5° C. | cis |
| Ex. 103 | $CH_3$ | 7-$OCH_2C_6H_5$ | H | 4-F | H | H | $\overset{H}{\underset{H}{>}}C=C\overset{H}{\underset{}{<}}$ | H | 140.5°-141.5° C. | trans |
| Ex. 104 | $CH_3$ | 5-$OCH_2C_6H_5$ | H | 4-F | H | H | $\overset{H}{\underset{H}{>}}C=C\overset{H}{\underset{}{<}}$ | H | 118°-119° C. | mixture ~80% cis ~20% trans |
| Ex. 105 | $CH_3$ | 5-$OCH_2C_6H_5$ | H | 4-F | H | H | $\overset{H}{\underset{H}{>}}C=C\overset{H}{\underset{}{<}}$ | H | | cis |
| Ex. 106 | $CH_3$ | 5-$OCH_2C_6H_5$ | H | 4-F | H | H | $\overset{H}{\underset{H}{>}}C=C\overset{H}{\underset{}{<}}$ | H | 118°-119° C. | trans |
| Ex. 107 | $C_6H_5CH_2CH_2-$ | H | H | 4-F | H | H | $\overset{H}{\underset{H}{>}}C=C\overset{H}{\underset{}{<}}$ | H | Solid foam | cis |
| Ex. 108 | $C_6H_5CH_2CH_2-$ | H | H | 4-F | H | H | $\overset{H}{\underset{H}{>}}C=C\overset{H}{\underset{}{<}}$ | H | Solid foam | trans |
| Ex. 109 | i-$C_3H_7$ | H | H | 3-$CH_3$ | 5-$CH_3$ | H | $\overset{H}{\underset{H}{>}}C=C\overset{H}{\underset{}{<}}$ | H | 108°-110° C. | cis |
| Ex. 110 | i-$C_3H_7$ | H | H | 3-$CH_3$ | 5-$CH_3$ | H | $\overset{H}{\underset{H}{>}}C=C\overset{H}{\underset{}{<}}$ | H | 145°-147° C. | trans |
| Ex. 111 | $C_2H_5$ | H | H | 4-F | H | H | $\overset{H}{\underset{H}{>}}C=C\overset{H}{\underset{}{<}}$ | H | 133.5°-135° C. | cis |

TABLE II-continued
Examples 83-122A
The following compounds of Group IAb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 112 | $C_2H_5$ | H | H | 4-F | H | H | \C=C/ with H's | H | 136°–137° C. | trans |
| Ex. 113 | i-$C_3H_7$ | H | H | 3-$CH_3$ | 4-F | H | \C=C/ with H's | H | 120°–123° C. | cis |
| Ex. 114 | i-$C_3H_7$ | H | H | 3-$CH_3$ | 4-F | H | \C=C/ with H's | H | 140.5°–141.5° C. | trans |
| Ex. 115 | i-$C_3H_7$ | 5-cyclohexyl | H | 4-F | H | H | \C=C/ with H's | H | Solid foam | cis |
| Ex. 116 | i-$C_3H_7$ | 5-cyclohexyl | H | 4-F | H | H | \C=C/ with H's | H | 162°–166° C. | trans |
| Ex. 117 | cyclohexyl | H | H | 4-F | H | H | \C=C/ with H's | H | Solid foam | cis |
| Ex. 118 | cyclohexyl | H | H | 4-F | H | H | \C=C/ with H's | H | Solid foam | trans |
| Ex. 119 | i-$C_3H_7$ | H | H | 2-$CH_3$ | H | H | \C=C/ with H's | H | Solid foam | cis |
| Ex. 120 | i-$C_3H_7$ | H | H | 2-$CH_3$ | H | H | \C=C/ with H's | H | Solid foam | trans |
| Ex. 121 | i-$C_3H_7$ | H | H | 3-$CH_3$ | 4-F | 5-$CH_3$ | \C=C/ with H's | H | 107°–113° C. | mixture ~88% cis ~12% trans |
| Ex. 122 | i-$C_3H_7$ | H | H | 3-$CH_3$ | 4-F | 5-$CH_3$ | \C=C/ with H's | H | 166.5°–167.5° C. | trans |
| Ex. 122A | i-$C_3H_7$ | 6-$OCH_2C_6H_5$ | H | 4-F | H | H | \C=C/ with H's | H | 152°–153° C. (dec.) | trans |

TABLE III
Examples 123-134
The following compounds of Group IBa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 123 | $CH_3$ | H | H | 4-F | H | H | \C=C/ with H's | H | $C_2H_5$ | | D |

TABLE III-continued

Examples 123-134
The following compounds of Group IBa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 124 | $CH_3$ | H | H | 4-F | H | H | −CH=CH− | H | K | | D |
| Ex. 125 | $CH_3$ | H | H | 4-F | H | H | −CH=CH− | H | H | | D |
| Ex. 126 | $C_2H_5$ | 5-$OCH_2$ | H | 3-$CH_3$ | H | H | −$CH_2CH_2$− | $CH_3$ | $CH_3$ | | D |
| Ex. 127 | $C_2H_5$ | 5-$OCH_3$ | H | 3-$CH_3$ | H | H | −$CH_2CH_2$− | $CH_3$ | K | | D |
| Ex. 128 | $C_2H_5$ | 5-$OCH_3$ | H | 3-$CH_3$ | H | H | −$CH_2CH_2$− | $CH_3$ | H | | D |
| Ex. 129 | i-$C_3H_7$ | H | H | 4-F | H | H | −CH=CH− | H | $C_2H_5$ | | D |
| Ex. 130 | i-$C_3H_7$ | H | H | 4-F | H | H | −CH=CH− | H | K | | D |
| Ex. 131 | i-$C_3H_7$ | H | H | 4-F | H | H | −CH=CH− | H | H | | D |
| Ex. 132 | $CH_3$ | H | H | H | H | H | −CH=CH− | H | $C_2H_5$ | Viscous oil | D |
| Ex. 133 | $CH_3$ | H | H | H | H | H | −CH=CH− | H | Na | | D |
| Ex. 134 | $CH_3$ | H | H | H | H | H | −CH=CH− | H | H | | D |

TABLE IV

Examples 135-142
The following compounds of Group IBb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 135 | $CH_3$ | H | H | 4-F | H | H | −CH=CH− | H | | cis |
| Ex. 136 | $CH_3$ | H | H | 4-F | H | H | −CH=CH− | H | | trans |
| Ex. 137 | $C_2H_5$ | 5-$OCH_3$ | H | 3-$CH_3$ | H | H | −$CH_2CH_2$− | $CH_3$ | | cis |
| Ex. 138 | $C_2H_5$ | 5-$OCH_3$ | H | 3-$CH_3$ | H | H | −$CH_2CH_2$− | $CH_3$ | | trans |
| Ex. 139 | i-$C_3H_7$ | H | H | 4-F | H | H | −CH=CH− | H | | cis |

TABLE IV-continued

Examples 135-142
The following compounds of Group IBb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 140 | i-$C_3H_7$ | H | H | 4-F | H | H | \C=C/ with H | H | | trans |
| Ex. 141 | $CH_3$ | H | H | H | H | H | \C=C/ with H | H | Solid foam | cis |
| Ex. 142 | $CH_3$ | H | H | H | H | H | \C=C/ with H | H | Viscous oil | trans |

In Tables I-IV,
DB = direct bond
D = mixture of diastereoisomers (four stereoisomers)
E = erythro racemate (two stereoisomers)
T = threo racemate (two stereoisomers)

Each of the compounds of Tables I and III denoted by a D in the Isomer(s) column is a mixture of four stereoisomers which may be separated. The four optically pure enantiomers that may be obtained may be designated as the 3R,5R,3S,5S,3R,5S and 3S,5R isomers. Except in the case of Examples 126-128, preferred are the 3R,5R and 3R,5S isomers and the racemate of which each is a constituent, viz., the 3R,5R-3S,5S (threo) racemate and the 3R,5S-3S,5R (erythro) racemate, of which the latter is preferred. The preferred isomers of Examples 126-128 are the 3R,5R and 3R,5S isomers and the racemate of which is a constituent, viz., the 3R,5R-3S,5S (erythro) racemate and the 3R,5S-3S,5R (threo) racemate, of which the former is preferred. Each of the compounds of Tables I and III denoted by an E in the Isomer(s) column is the erythro racemate which may be resolved to obtain the 3R,5S and 3S,5R enantiomers by, for example, (i) lactonization, (ii) conversion to a mixture of two diastereoisomeric silyloxy compounds, (iii) chromatographic separation of the diastereoisomeric silyloxy compounds, (iv) cleavage of the silyl group and (v) hydrolysis of the obtained optically pure lactone, as set forth in more detail above. Each of the compounds of Tables I and III denoted by a T in the Isomer(s) column is the threo racemate which may be resolved by, for example, the same procedure to obtain the 3R,5R and 3S,5S enantiomers.

Each of the compounds of Tables II and IV denoted by cis in the Isomer(s) column is the cis racemate and each of the compounds of these tables denoted by trans in the Isomer(s) column is the trans racemate, cis and trans referring to the relative positions of the hydrogen atoms in the 4- and 6-positions of the lactone ring. The cis racemates of Examples 88 and 137 may be resolved to obtain the 4R,6S and 4S,6R enantiomers and each of the other cis racemates of Tables II and IV may be resolved to obtain the 4R,6R and 4S,6S enantiomers, of which the 4R,6S and 4R,6R enantiomers are preferred. The trans racemates of Examples 89 and 138 may be resolved to obtain the 4R,6R and 4S,6S enantiomers, and each of the other trans racemates of Tables II and IV may be resolved to obtain the 4R,6S and 4S,6R enantiomers, of which the 4R,6R and 4R,6S enantiomers are preferred. The cis and trans racemates may be resolved by Steps (ii)-(iv) of the procedure outlined in the preceding paragraph.

Each of the compounds of Examples 2, 6, 8, 9 and 14 and the examples of Tables I and III wherein $R_7$ is a cation may be converted into the corresponding free acid and into the corresponding compounds wherein $R_7$ is a different M by conventional means.

Each of the compounds of Examples 1-142 (including each of the possible optical isomers) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

TABLE V

The following compounds of Formula XX may be obtained by the process set forth above.

| | R | $R_o$ | $R_2$ | $R_3$ | m.p. |
|---|---|---|---|---|---|
| Ex. Va | 3,4-di-$CH_3$—$C_6H_3$— | $CH_3$ | H | H | 97°-99° C. |
| Ex. Vb | 4-F—$C_6H_4$— | $C_6H_5CH_2CH_2$— | H | H | 86°-88° C. |
| Ex. Vc | 4-F—$C_6H_4$— | i-$C_3H_7$ | 5-cyclohexyl | H | 162°-167° C. |
| Ex. Vd | 2-$CH_3$—$C_6H_4$— | i-$C_3H_7$ | H | H | 190°-193° C. |
| Ex. Ve | 3,5-di-$CH_3$—$C_6H_3$— | $CH_3$ | H | H | 117°-118.5° C. |
| Ex. Vf | 4-F—$C_6H_4$— | $CH_3$ | 5-$OCH_3$ | H | 137°-138.5° C. |
| Ex. Vg | 4-F—$C_6H_4$— | $CH_3$ | 6-$OCH_2C_6H_5$ | H | 128.5°-131° C. |
| Ex. Vh | 4-F—$C_6H_4$— | $CH_3$ | 4-$OCH_2C_6H_5$ | H | 162.5°-164° C. |
| Ex. Vi | 4-F—$C_6H_4$— | $CH_3$ | 5-Cl | H | 169.5°-170.5° C. |
| Ex. Vj | $C_6H_5$— | $CH_3$ | H | H | 141.5°-142.5° C. |
| Ex. Vk | 4-F—$C_6H_4$— | $CH_3$ | 7-$OCH_2C_6H_5$ | H | 140°-141° C. |
| Ex. Vl | 4-F—$C_6H_4$— | $CH_3$ | 5-$OCH_2C_6H_5$ | H | 124.5°-125° C. |
| Ex. Vm | 3-$CF_3$—$C_6H_4$— | $CH_3$ | H | H | 124°-124.5° C. |

TABLE V-continued

The following compounds of Formula XX may be obtained by the process set forth above.

| | R | $R_o$ | $R_2$ | $R_3$ | m.p. |
|---|---|---|---|---|---|
| Ex. Vn | 4-F—$C_6H_4$— | $C_2H_5$ | H | H | 103°–105° C. |
| Ex. Vo | 4-F—$C_6H_4$— | i-$C_3H_7$ | 4-$CH_3$ | 6-$CH_3$ | 189°–190° C. |
| Ex. Vp | $C_6H_5$— | i-$C_3H_7$ | H | H | 111°–112° C. |
| Ex. Vq | 3,5-di-$CH_3$-4-F—$C_6H_2$— | i-$C_3H_7$ | H | H | 114.5°–115° C. |
| Ex. Vr | 4-F—$C_6H_4$— | i-$C_3H_7$ | 6-$OCH_2C_6H_5$ | H | 118.5°–120° C. |
| Ex. Vs | 4-F-$C_6H_4$— | i-$C_3H_7$ | 4-i-$C_3H_7$ | 6-i-$C_3H_7$ | 162°–163° C. |
| Ex. Vt | $CH_3$ | $C_6H_5$— | H | H | crude amorphous solid |

TABLE VI

The following compound of Formula XXIV may be obtained by the processes set forth above.

| | R | $R_o$ | $R_2$ | $R_3$ | $Y^\ominus$ | m.p. |
|---|---|---|---|---|---|---|
| Ex. VIa | 4-F—$C_6H_4$— | i-$C_3H_7$ | H | H | $Cl^\ominus$ | 236°–239° C. |

Throughout the examples, the term "reduced pressure" denotes aspirator pressure, and where no solvent is specified in connection with a solution, the solvent is water. All N.M.R. spectra were taken at ambient temperature on a 200 MHz. N.M.R. spectrometer (except where otherwise indicated) and all chemical shifts are given in p.p.m. (δ) relative to tetramethylsilane. Where a single δ value is given for anything other than a sharp singlet, it is its center point. All solvent mixtures are by volume.

What is claimed is:

1. A compound of the formula

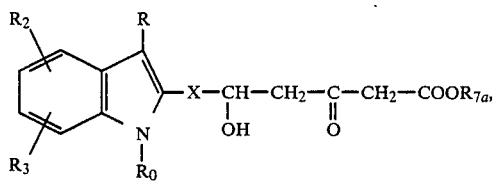

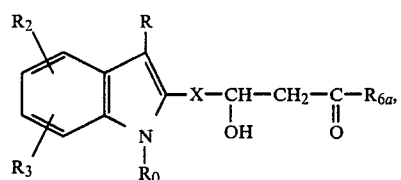

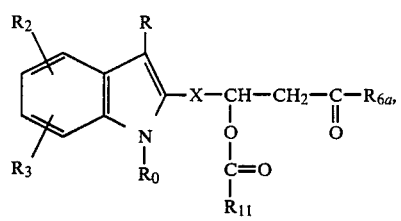

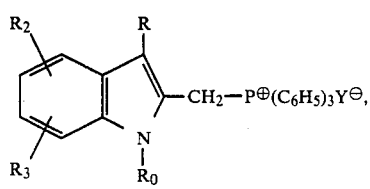

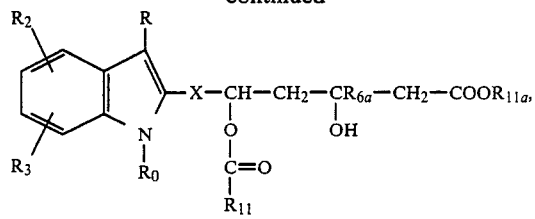

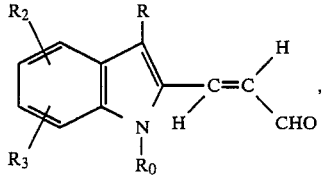

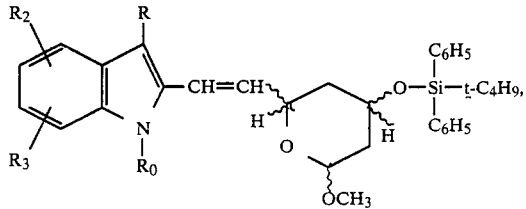

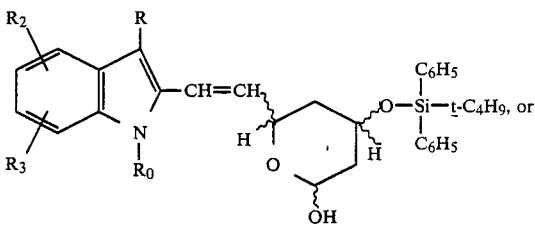

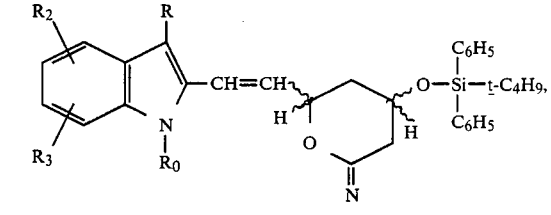

wherein one of R and $R_o$ is

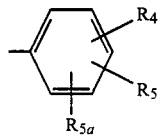

and the other is primary or secondary $C_{1-6}$alkyl not having an asymmetric carbon atom, $C_{3-6}$cycloalkyl or phenyl-$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, and m is 1, 2, or 3, with the provisos that not more than one of $R_4$ and $R_5$ is trifluoromethyl, not more than one of $R_4$ and $R_5$ is phenoxy and not more than one of $R_4$ and $R_5$ is benzyloxy, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ is benzyloxy, $R_{6a}$ is $C_{1-3}$alkyl, $R_{7a}$ is $C_{1-3}$alkyl, n-butyl, i-butyl, t-butyl or benzyl, $R_{11}$ is $C_{1-2}$alkyl, $R_{11a}$ is $C_{1-3}$alkyl, n-butyl or t-butyl, X is —$(CH_2)_n$— or —CH=CH—, wherein n is 0, 1, 2 or 3, and $Y^\ominus$ is chloride or bromide.

2. A compound according to claim 1 having the formula

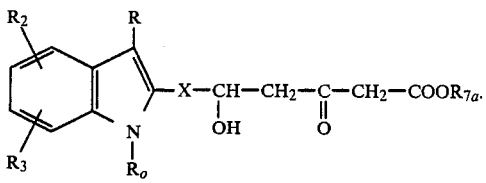

3. The compound according to claim 2 having the formula

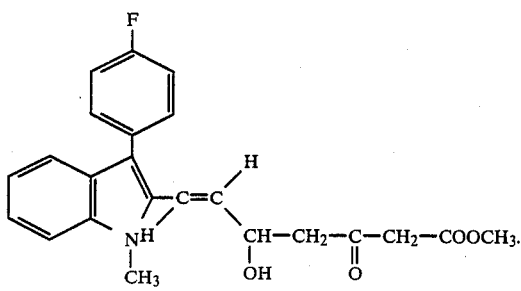

4. The compound according to claim 2 having the formula

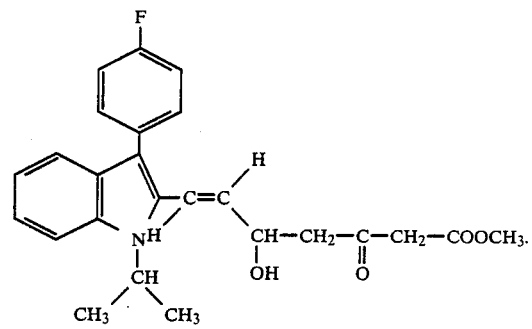

5. A compound according to claim 1 having the formula

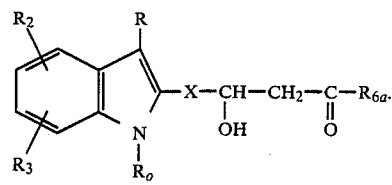

6. A compound according to claim 1 having the formula

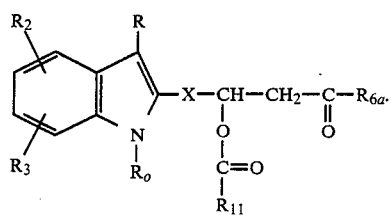

7. A compound according to claim 1 having the formula

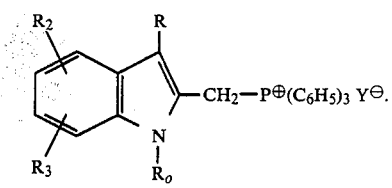

8. The compound according to claim 7 having the formula

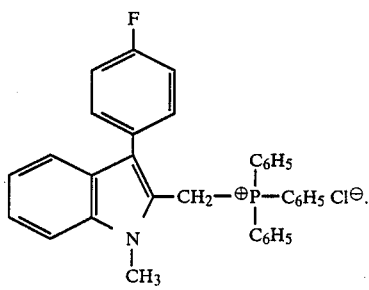

9. A compound according to claim 1 having the formula

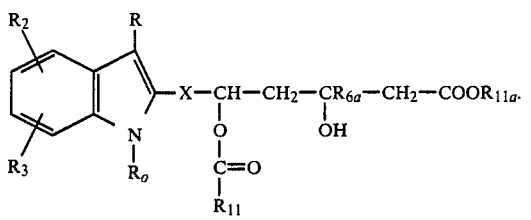

10. A compound according to claim 1 having the formula

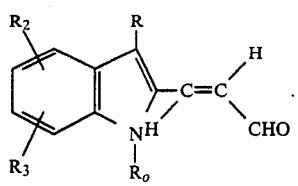

11. A compound according to claim 10 wherein R is

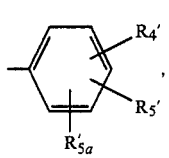

wherein
- $R_4'$ is hydrogen, $C_{1-3}$alkyl, $C_{1-3}$alkoxy, trifluoromethyl, fluoro, chloro, phenoxy or benzyloxy,
- $R_5'$ is hydrogen, $C_{1-2}$alkyl, $C_{1-2}$alkoxy, fluoro or chloro, and
- $R_{5a}'$ is hydrogen or methyl,
- $R_o$ is primary or secondary $C_{1-6}$alkyl not having an asymmetric carbon atom,
- $R_2$ is hydrogen, $C_{1-3}$alkyl, $C_{1-3}$alkoxy, trifluoromethyl, fluoro, chloro, phenoxy or benzyloxy, and
- $R_3$ is hydrogen, $C_{1-3}$alkyl, $C_{1-2}$alkoxy, fluoro or chloro.

12. A compound according to claim 11 wherein
- $R_o$ is $C_{1-3}$alkyl,
- $R_2$ is hydrogen, $C_{1-3}$alkyl, methoxy, fluoro, chloro or 4-, 5- or 6-benzyloxy,
- $R_3$ is hydrogen or $C_{1-3}$alkyl,
- $R_4'$ is hydrogen, methyl, methoxy, fluoro or chloro,
- $R_5'$ is hydrogen, methyl, methoxy, fluoro or chloro, and
- $R_{5a}'$ is hydrogen or methyl.

13. The compound according to claim 12 having the formula

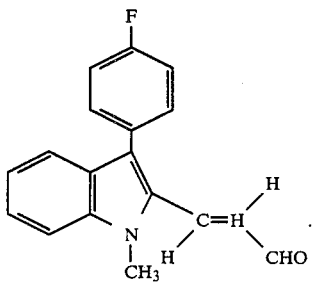

14. The compound according to claim 12 having the formula

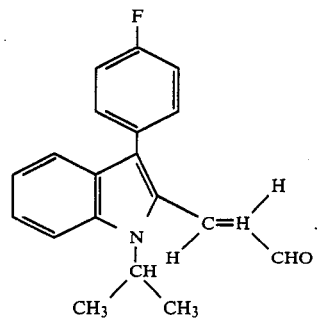

15. A compound according to claim 1 having the formula

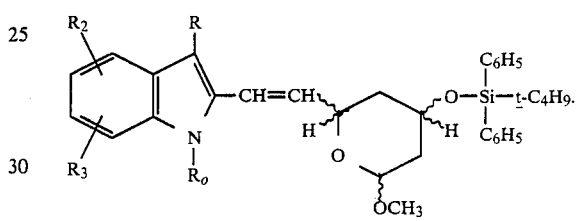

16. The compound according to claim 15 having the formula

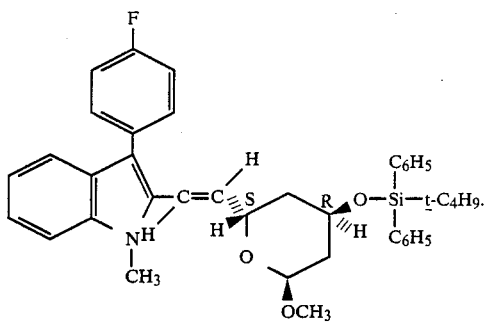

17. A compound according to claim 1 having the formula

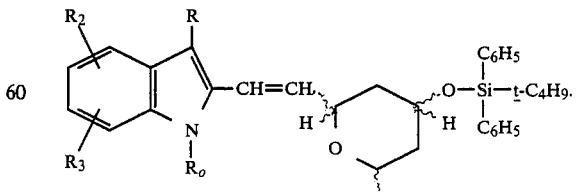

18. A compound according to claim 17 having the formula

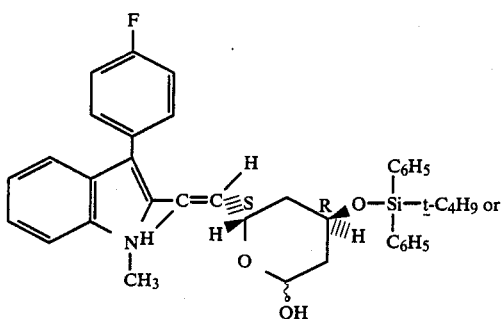
19. A compound according to claim 1 having the formula
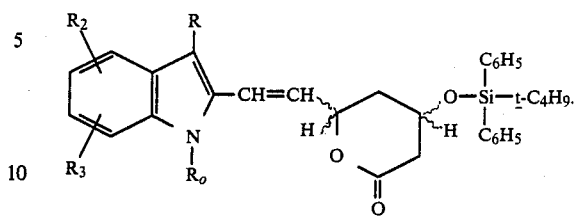
20. The compound according to claim 19 having the formula
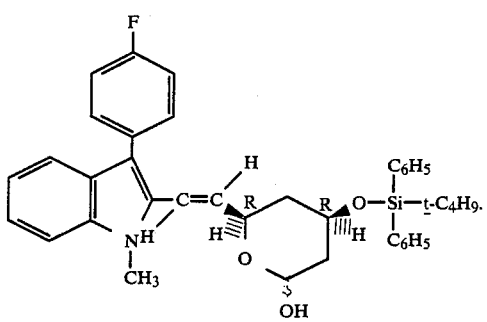
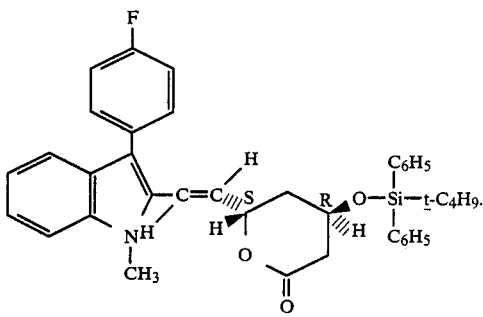
* * * * *